US007547821B2

(12) United States Patent
Moloney et al.

(10) Patent No.: US 7,547,821 B2
(45) Date of Patent: Jun. 16, 2009

(54) METHODS FOR THE PRODUCTION OF INSULIN IN PLANTS

(75) Inventors: Maurice M. Moloney, Calgary (CA); Joseph Boothe, Calgary (CA); Richard Keon, Calgary (CA); Cory Nykiforuk, Calgary (CA); Gijs Van Rooijen, Calgary (CA)

(73) Assignee: SemBioSys Genetics Inc., Calgary, Alberta (CA)

( * ) Notice: Subject to any disclaimer, the term of this patent is extended or adjusted under 35 U.S.C. 154(b) by 0 days.

(21) Appl. No.: 10/869,040

(22) Filed: Jun. 17, 2004

(65) Prior Publication Data

US 2005/0039235 A1 Feb. 17, 2005

Related U.S. Application Data

(60) Provisional application No. 60/549,539, filed on Mar. 4, 2004, provisional application No. 60/478,818, filed on Jun. 17, 2003.

(51) Int. Cl.
*C12N 15/82* (2006.01)
*A01H 5/00* (2006.01)
*C07H 21/04* (2006.01)

(52) U.S. Cl. ....................... 800/288; 800/287; 800/298; 536/23.51; 536/23.4; 536/23.5

(58) Field of Classification Search ....................... None
See application file for complete search history.

(56) References Cited

U.S. PATENT DOCUMENTS

| | | | |
|---|---|---|---|
| 4,956,282 | A | 9/1990 | Goodman et al. |
| 5,202,422 | A | 4/1993 | Hiatt et al. |
| 5,550,038 | A | 8/1996 | Goodman et al. |
| 5,629,175 | A | 5/1997 | Goodman et al. |
| 5,639,947 | A | 6/1997 | Hiatt et al. |
| 5,650,307 | A | 7/1997 | Sijmons et al. |
| 5,677,474 | A | 10/1997 | Rogers |
| 5,716,802 | A | 2/1998 | Sijmons et al. |
| 5,763,748 | A | 6/1998 | Sijmons et al. |
| 5,959,177 | A | 9/1999 | Hein et al. |

FOREIGN PATENT DOCUMENTS

| | | | |
|---|---|---|---|
| EP | 0 437 320 A1 | | 7/1991 |
| WO | WO 91/13993 | * | 9/1991 |
| WO | WO 94/14970 | * | 7/1994 |
| WO | WO 98/27115 | * | 6/1998 |
| WO | WO 99/16890 | | 4/1999 |
| WO | WO 99/55890 | | 11/1999 |
| WO | WO 01/72959 | | 10/2001 |
| WO | WO 03/076595 | | 9/2003 |

OTHER PUBLICATIONS

Arakawa et al. A plant-based cholera toxin B subunit-insulin fusion protein protects against the development of autoimmune diabetes. (1998) Nature Biotehcnology, vol. 16, pp. 934-938.*

Rakousky et al. Hygromycin B- an alternative in flax transformant selection. (1999) Biologia Plantarum, Bol. 42, pp. 361-369.*

Hirsh I.B. Type 1 diabetes mellitus and the use of flexible insulin regimens. (1999) American Family Physician; http://www.aafp.org/afp/991115ap/2343.html, pp. 1-15.*

Whitelam G.C. The Production of recombinant proteins in plants. (1995) J. Sci. Food Agric. , vol. 68, pp. 1-9.*

Le Flem et al. Synthesis, and funtional properties of a modified human isulin A-Chain: Implication in a 'mini-insulin' structure determination. (2002) Bioorganic and Medicinal Chem., vol. 10, pp. 2111-2117.*

Giddings G. Transgenic plants as protein factories (2001) Curr. Opin. in Biotech., vol. 12, pp. 450-454.*

Horvath et al. The production of recombinant proteins in transgenic barley grains. (2000) PNAS, vol. 97, pp. 1914-1919.*

Arakawa, T. et al., *Nature Biotechnology*, Oct. 1998; 16(10):934-8.

Chan, S.J. et al., *Proc. Natl. Acad. Sci. USA*, Sep. 1981, 78(9):5401-5.

Frank, B.H. et al., *Peptides: Proceedings of the 7th American Peptide Chemistry Symposium* (Rich & Gross. Eds.), Pierce Chemical Co., Rockford, Ill, 1981, p. 729-739.

Kjeldsen, T. et al., *Biotechnology & Genetic Engineering Reviews*, 2001, 18:89-121.

Thim, L. et al. *Proc. Natl. Acad. Sci. USA*, Sep. 1986, 83(18):6766-6770.

Wang, Y. et al., *Biotechnology and Bioengineering*, Apr. 2001, 73(1):74-9.

Yanagita, M. et al. *FEBS Letters*, Oct. 1992, 311(1):55-9.

Database WPI, *Section Ch, Week 200148*, Derwent Publications Ltd., London, GB, Class B04, AN 2001-442770, May 16, 2001; abstract.

Moloney, M. M., *Oleosin Partitioning Technology for Production of Recombinant Proteins in Oil Seeds*, Handbook of Industrial Cell Culture: Mammalian, Microbial and Plant Cells, XX, XX, 2002, pp. 279-295.

OTHER PUBLICATIONS

Murphy, Denis J., *Biotechnology and the improvement of oil crops: Genes, Dreams and Realities*, Phytochemistry Reviews, vol. 1, No. 1, 2002, pp. 67-77.

Rishi, A.S. et al., *Molecular Farming in Plants: A current perspective*, Journal of Plant Biochemistry and Biotechnology, vol. 10, No. 1, Jan. 2001, pp. 1-12.

Van Rooijen G.J.H. et al., Plant Seed Oil-Bodies as Carriers for Foreign Proteins, Bio/Technology, vol. 13, No. 1, 1995, pp. 72-77, Nature Publishing Co., New York, US.

* cited by examiner (Continued)

*Primary Examiner*—Cathy Kingdon Worley
(74) *Attorney, Agent, or Firm*—Bereskin & Parr; Micheline Gravelle

(57) ABSTRACT

Commercial production of human insulin can be affected via transgenic expression in plant seeds. Thus, levels of insulin accumulation exceeding 0.1% of total cellular protein can be achieved recombinantly, through expression of the insulin with a single-chain antibody as a fusion partner. Production in seeds offers flexibility in storage and shipment of insulin as a raw material, and insulin retains its activity upon extraction from stored seed. Further, the amount of biomass subjected to extraction is limited, due to the relatively low water content of plant seeds.

29 Claims, 17 Drawing Sheets

FIGURE 1-1

```
1     atgaacttccttaagtctttccctttctacgctttcctttgtttcggtcaatacttcgtt    60
1      M  N  F  L  K  S  F  P  F  Y  A  F  L  C  F  G  Q  Y  F  V     20

61    gctgttacgcatgctgacattgtgatgacacagtctccatcctccctggctatgtcagtg   120
21     A  V  T  H  A  D  I  V  M  T  Q  S  P  S  S  L  A  M  S  V     40

121   ggacagcgggtcactatgcgctgcaagtccagtcagagccttttaaaaagtaccaatcaa   180
41     G  Q  R  V  T  M  R  C  K  S  S  Q  S  L  L  K  S  T  N  Q     60

181   aagaactatttggcctggtaccagcagaaaccaggacagtctcctaaacttctggtatac   240
61     K  N  Y  L  A  W  Y  Q  Q  K  P  G  Q  S  P  K  L  L  V  Y     80

241   tttgcatccactagggaatctggggtccctgatcgcttcataggcagtggatctgggaca   300
81     F  A  S  T  R  E  S  G  V  P  D  R  F  I  G  S  G  S  G  T    100

301   gatttcactcttaccatcagcagtgtgcaggctgaagacctggcagattacttctgtcag   360
101    D  F  T  L  T  I  S  S  V  Q  A  E  D  L  A  D  Y  F  C  Q    120

361   caacattataacactcctcccacgttcggtgctgggaccaagctggagcttaagcggtct   420
121    Q  H  Y  N  T  P  P  T  F  G  A  G  T  K  L  E  L  K  R  S    140

421   ccgaacggtgcttctcatagcggttctgcaccaggcactagctctgcatctggatctcag   480
141    P  N  G  A  S  H  S  G  S  A  P  G  T  S  S  A  S  G  S  Q    160

481   gtgcacctgcagcagtctggagctgagctgatgaagcctggggcctcaatgaagatatcc   540
161    V  H  L  Q  Q  S  G  A  E  L  M  K  P  G  A  S  M  K  I  S    180

541   tgcaaggctactggctacacattcagtagctactggatagagtgggtaaagcagaggcct   600
181    C  K  A  T  G  Y  T  F  S  S  Y  W  I  E  W  V  K  Q  R  P    200

601   ggacatggccttgagtggattggagagatttacctggcagtggtagtactacctacaat   660
201    G  H  G  L  E  W  I  G  E  I  L  P  G  S  G  S  T  T  Y  N    220

661   gagaagttcaagggcaaggccacattcactgcagatacatcctccaacacagcctacatg   720
221    E  K  F  K  G  K  A  T  F  T  A  D  T  S  S  N  T  A  Y  M    240

721   caactcagcagcctgacatctgaggactctgccgtctattactgtgcaagattggatgtt   780
241    Q  L  S  S  L  T  S  E  D  S  A  V  Y  Y  C  A  R  L  D  V    260

781   gactcctggggccaaggcaccactctcacagtctcgagtcaaccaattgatgacactgaa   840
261    D  S  W  G  Q  G  T  T  L  T  V  S  S  Q  P  I  D  D  T  E    280

841   tcccagaccacgtcagtgaacctcatggccgatgatactgagagcgcgtttgctacacaa   900
281    S  Q  T  T  S  V  N  L  M  A  D  D  T  E  S  A  F  A  T  Q    300

901   acaaattcgggaggtcttgacgttgtcggattgatctccatggctaagagagaagaagga   960
301    T  N  S  G  G  L  D  V  V  G  L  I  S  M  A  K  R  E  E  G    320

961   gagcctaagtttgttaatcaacatctttgtggatctcatcttgttgaggctctctacctt  1020
321    E  P  K  F  V  N  Q  H  L  C  G  S  H  L  V  E  A  L  Y  L    340
```

FIGURE 1-2

```
1021 gtgtgtggagaaagaggatttttctacactcctaaggctgctaagggaattgttgaacaa 1080
341   V  C  G  E  R  G  F  F  Y  T  P  K  A  A  K  G  I  V  E  Q  360

1081 tgttgcacttctatttgctcactttaccaattggagaactattgcaacaaggatgaactt 1040
361   C  C  T  S  I  C  S  L  Y  Q  L  E  N  Y  C  N  K  D  E  L  380

1041  tga
```

FIGURE 2

```
1    atggcggatacagctagaggaacccatcacgatatcatcggcagagaccagtacccgatg  60
1     M  A  D  T  A  R  G  T  H  H  D  I  I  G  R  D  Q  Y  P  M    20

61   atgggccgagaccgagaccagtaccagatgtccggacgaggatctgactactccaagtct  120
21    M  G  R  D  R  D  Q  Y  Q  M  S  G  R  G  S  D  Y  S  K  S    40

121  aggcagattgctaaagctgcaactgctgtcacagctggtggttccctccttgttctctcc  180
41    R  Q  I  A  K  A  A  T  A  V  T  A  G  G  S  L  L  V  L  S    60

181  agccttacccttgttggaactgtcatagctttgactgttgcaacacctctgctcgttatc  240
61    S  L  T  L  V  G  T  V  I  A  L  T  V  A  T  P  L  L  V  I    80

241  ttcagcccaatccttgtcccggctctcatcacagttgcactcctcatcaccggttttctt  300
81    F  S  P  I  L  V  P  A  L  I  T  V  A  L  L  I  T  G  F  L    100

301  tcctctggagggtttggcattgccgctataaccgttttctcttggatttacgcaacggga  360
101   S  S  G  G  F  G  I  A  A  I  T  V  F  S  W  I  Y  A  T  G   120

361  gagcacccacagggatcagacaagttggacagtgcaaggatgaagttgggaagcaaagct  420
121   E  H  P  Q  G  S  D  K  L  D  S  A  R  M  K  L  G  S  K  A    140

421  caggatctgaaagacagagctcagtactacggacagcaacatactggtggggaacatgac  480
141   Q  D  L  K  D  R  A  Q  Y  Y  G  Q  Q  H  T  G  G  E  H  D    160

481  cgtgaccgtactcgtggtggccagcacactaccatggctgagatcacccgcattcctctc  540
161   R  D  R  T  R  G  G  Q  H  T  T  M  A  E  I  T  R  I  P  L    180

541  tacaaaggtaagtctctccgtaaggcgctgaaggaacatggacttctagaagacttcttg  600
181   Y  K  G  K  S  L  R  K  A  L  K  E  H  G  L  L  E  D  F  L    200

601  cagaaacaacagtatggcatctcgagcaagttccaaccaattgatgacactgaatcccag  660
201   Q  K  Q  Q  Y  G  I  S  S  K  F  Q  P  I  D  D  T  E  S  Q    220

661  accacgtcagtgaacctcatggccgatgatactgagagcgcgtttgctacacaaacaaat  720
221   T  T  S  V  N  L  M  A  D  D  T  E  S  A  F  A  T  Q  T  N    240

721  tcgggaggtcttgacgttgtcggattgatctccatggctaagagagaagaaggagagcct  780
241   S  G  G  L  D  V  V  G  L  I  S  M  A  K  R  E  E  G  E  P    260

781  aagtttgttaatcaacatctttgtggatctcatcttgttgaggctctctaccttgtgtgt  840
261   K  F  V  N  Q  H  L  C  G  S  H  L  V  E  A  L  Y  L  V  C    280

841  ggagaaagaggatttttctacactcctaaggctgctaagggaattgttgaacaatgttgc  900
281   G  E  R  G  F  F  Y  T  P  K  A  A  K  G  I  V  E  Q  C  C    300

901  acttctatttgctcactttaccaattggagaactattgcaactga
301   T  S  I  C  S  L  Y  Q  L  E  N  Y  C  N  -
```

FIGURE 3

```
1    atgaacttccttaagtctttccctttctacgctttcctttgtttcggtcaatacttcgtt  60
1     M  N  F  L  K  S  F  P  F  Y  A  F  L  C  F  G  Q  Y  F  V   20

61   gctgttacgcatgcctttgttaatcaacatctttgtggatctcatcttgttgaggctctc  120
21    A  V  T  H  A  F  V  N  Q  H  L  C  G  S  H  L  V  E  A  L   40

121  taccttgtgtgtggagaaagaggattttctacactcctaagactagaagaaagagagga  180
41    Y  L  V  C  G  E  R  G  F  F  Y  T  P  K  T  R  R  K  R  G   60

181  attgttgaacaatgttgcacttctatttgctcactttaccaattggagaactattgcaac  240
61    I  V  E  Q  C  C  T  S  I  C  S  L  Y  Q  L  E  N  Y  C  N   80

241  agaagaaagagagacattgtgatgacacagtctccatcctccctggctatgtcagtggga  300
81    R  R  K  R  D  I  V  M  T  Q  S  P  S  S  L  A  M  S  V  G   100

301  cagcgggtcactatgcgctgcaagtccagtcagagccttttaaaaagtaccaatcaaaag  360
101   Q  R  V  T  M  R  C  K  S  S  Q  S  L  L  K  S  T  N  Q  K   120

361  aactatttggcctggtaccagcagaaaccaggacagtctcctaaacttctggtatacttt  420
121   N  Y  L  A  W  Y  Q  Q  K  P  G  Q  S  P  K  L  L  V  Y  F   140

421  gcatccactagggaatctggggtccctgatcgcttcataggcagtggatctgggacagat  480
141   A  S  T  R  E  S  G  V  P  D  R  F  I  G  S  G  S  G  T  D   160

481  ttcactcttaccatcagcagtgtgcaggctgaagacctggcagattacttctgtcagcaa  540
161   F  T  L  T  I  S  S  V  Q  A  E  D  L  A  D  Y  F  C  Q  Q   180

541  cattataacactcctcccacgttcggtgctgggaccaagttggagcttaagcggtctccg  600
181   H  Y  N  T  P  P  T  F  G  A  G  T  K  L  E  L  K  R  S  P   200

601  aacggtgcttctcatagcggttctgcaccaggcactagctctgcatctggatctcaggtg  660
201   N  G  A  S  H  S  G  S  A  P  G  T  S  S  A  S  G  S  Q  V   220

661  cacctgcagcagtctggagctgagctgatgaagcctggggcctcaatgaagatatcctgc  720
221   H  L  Q  Q  S  G  A  E  L  M  K  P  G  A  S  M  K  I  S  C   240

721  aaggctactggctacacattcagtagctactggatagagtgggtaaagcagaggcctgga  780
241   K  A  T  G  Y  T  F  S  S  Y  W  I  E  W  V  K  Q  R  P  G   260

781  catggccttgagtggattggagagatttacctggcagtggtagtactacctacaatgag  840
261   H  G  L  E  W  I  G  E  I  L  P  G  S  G  S  T  T  Y  N  E   280

841  aagttcaagggcaaggccacattcactgcagatacatcctccaacacagcctacatgcaa  900
281   K  F  K  G  K  A  T  F  T  A  D  T  S  S  N  T  A  Y  M  Q   300

901  ctcagcagcctgacatctgaggactctgccgtctattactgtgcaagattggatgttgac  960
301   L  S  S  L  T  S  E  D  S  A  V  Y  Y  C  A  R  L  D  V  D   320

961  tcctggggccaaggcaccactctcacagtgagctcaaaggatgagctttga
321   S  W  G  Q  G  T  T  L  T  V  S  S  K  D  E  L
```

| Construct | Line | Transgene (% total seed protein) | Mini-insulin (% total seed protein) |
|---|---|---|---|
| 4404 | 2 | 1.20 | 0.20 |
| 4404 | 17 | 1.09 | 0.19 |
| 4404 | 20 | 1.39 | 0.24 |
| 4405 | 4 | 0.63 | 0.11 |
| 4405 | 13 | 0.62 | 0.11 |
| 4405 | 19 | 0.75 | 0.13 |
| 4414 | 9 | 6.78 | 1.15 |
| 4414 | 20 | 2.50 | 0.42 |
| Wt | C24 | 0 | 0 |

A)

B)

Insulin Tolerance Tests in C57Bl/6 Male Mice

METHODS FOR THE PRODUCTION OF INSULIN IN PLANTS

This application claims the benefit under 35 USC §119(e) from U.S. Provisional patent applications Ser. No. 60/478,818 filed Jun. 17, 2003 and Ser. No. 60/549,539 filed Mar. 4, 2004, which are incorporated herein by reference in their entirety.

FIELD OF THE INVENTION

The present invention relates to plant genetic engineering methods and to the production of insulin. More specifically, the present invention relates to methods for the production of insulin in the seeds of plants.

BACKGROUND OF THE INVENTION

Insulin is an important peptide hormone required to maintain blood glucose homeostasis in mammals, including humans, and other vertebrates. In healthy individuals an increase in blood glucose level stimulates the β-cells of the pancreas to secrete insulin. The insulin polypeptide then binds to specific receptors in muscle, liver, and adipose tissue leading to an increase in glucose uptake by these targeted tissues, an increase in metabolism, and a decrease in hepatic glucose production. The cumulative effects of these responses serve to keep blood glucose concentrations at a constant level.

In individuals suffering from diabetes mellitus, an abnormally low insulin concentration presents itself as chronic hyperglycemia. The clinical manifestations of chronic hyperglycemia are manifold, and include blindness, kidney failure and, if left untreated, will ultimately result in death. Estimates place diabetes mellitus as the third largest cause of death in industrialized countries, after cardiovascular diseases and cancer (Barfoed, H. C., 1987, Chem. Eng. Prog. 83:49-54). In order to allow efficient uptake and metabolism of blood glucose by the cells, diabetic individuals may be treated by the routine administration of insulin. Approximately 0.7% of the world's population suffers from insulin-dependent diabetes (diabetes mellitus Type I) (Winter, J. et al., 2000, J. of Biotechnol. 84:175-185). In addition, it is estimated that the number of individuals diagnosed with diabetes will double to approximately 300 million, in the next 25 years (Kjeldsen, T. et al., 2001, Biotechnol. Gen. Eng. Rev. 18:89-121). Consequently, the ability to cost effectively manufacture human insulin in quantities to satisfy the anticipated growing world demand for insulin is highly desirable.

In vivo the human insulin polypeptide is produced by the pancreatic β-cells as a single 110 amino acid polypeptide chain precursor, preproinsulin, which includes an N-terminally located 24 amino acid pre-sequence that is cleaved immediately upon completion of the chain's biosynthesis (Steiner, D. F. 2000. J. Ped. Endocrinol. Metab. 13:229-239). Proinsulin consists of a B and A chain, linked by a connecting peptide (C-peptide). During packaging of the hormone for secretion the C-peptide is cleaved and removed by prohormone convertases, PC2 and PC1/PC3 (Steiner, D. F. 2000. J. Ped. Endocrinol. Metab. 13:229-239). What remains is mature human insulin, a 51 amino acid protein consisting of two polypeptide chains, A (21 amino acids in length) and B (30 amino acids in length), linked by two inter-chain disulphide bonds. Additionally, the A chain comprises one intra-chain disulphide bond.

Human insulin has been prepared using a variety of different methodologies. Microorganisms such as *Escherichia coli*

(Frank et al., 1981, in Peptides: Proceedings of the $7^{th}$ American Peptide Chemistry Symposium (Rich & Gross, eds.), Pierce Chemical Co., Rockford. Ill. pp 729-739; Chan et al., 1981, Proc Natl. Acad. Sci. USA 78: 5401-5404), *Saccharomyces cerevisiae* (Thim et al., 1986, Proc. Natl. Acad. Sci. USA 83: 6766-6770) are routinely employed to recombinantly produce insulin. Wang et al. (Biotechnol. Bioeng., 2001, 73:74-79) have shown that fungi, such as Pichia pastoris, are also suitable for insulin production. Alternative manufacturing options include production in non-human mammalian cell lines (Yanagita, M., et al., 1992, FEBS Lett 311:55-59), isolation from human pancreas, peptide synthesis, or the semisynthetic conversion to human insulin from porcine and bovine insulin. However, all of these methods suffer from lower yields and higher costs than desired.

The use of plants as bioreactors for the large scale production of recombinant proteins is well known, and numerous proteins, including human therapeutic proteins, have been produced. For example, U.S. Pat. Nos. 4,956,282, 5,550,038 and 5,629,175 disclose the production of γ-interferon in plants; U.S. Pat. Nos. 5,650,307, 5,716,802 and 5,763,748 detail the production of human serum albumin in plants and U.S. Pat. Nos. 5,202,422, 5,639,947 and 5,959,177 relate to the production of antibodies in plants. One of the significant advantages offered by plant-based recombinant protein production systems is that by increasing the acreage of plants grown, protein production can be inexpensively scaled up to provide for large quantities of protein. By contrast, fermentation and cell culture systems have large space, equipment and energy requirements, rendering scale-up of production costly. However, despite the fact that the use of plants as bioreactors is amply documented, and despite the above mentioned anticipated prodigious increase in need for large volumes of insulin, the prior art provides only a limited number of methods which demonstrably result in the production of insulin in plants (see: Arakawa et al. Nature Biotech., 1998, 16: 934-938; PCT 01/72959).

Arakawa et al. disclose the production of a fusion protein comprising insulin in the tubers of transgenic potato plants. However insulin represents only up to 0.05% of the total soluble protein content present in the transgenic tubers. At a level of 0.05% of total soluble protein, large amounts of biomass must be subjected to protein extraction rendering the production economics associated with the use of potato tubers unfavorable. Furthermore, Arakawa et al. are not concerned with the isolation of insulin from the potato tuber tissue, but instead suggest an approach prevent the onset of Type I diabetes by inducing immunotolerance which involves oral administration of insulin through the feeding of transgenic potato tubers.

PCT Patent Application WO 01/72959 discloses the production of a fusion protein comprising insulin in chloroplasts of transgenic tobacco. However, while purportedly addressing shortcomings with respect to the accumulation levels of human proteins in plant tissue, the invention to which WO 01/72959 pertains is limited in that production in chloroplasts results in the accumulation of insulin in green tissue, primarily the tobacco leaves. Due to the relatively high water content of green tissue, a large amount of biomass must be processed. Furthermore production of insulin would require immediate extraction from the biomass upon harvesting, as leaf material will rapidly deteriorate when stored.

Thus in view of the shortcomings associated with the methods for the recombinant production of insulin in plants provided by the prior art, it is presently unclear whether and how the synthetic capacity of plants may be harnessed to achieve the commercial production of insulin in plants. There is a need in the art to improve methods for the commercial production of insulin in plants.

SUMMARY OF THE INVENTION

The present invention relates to improved methods for the production of insulin in plants. In particular the present invention relates to methods for the production of insulin in seeds.

Accordingly, the present invention provides a method for the expression of insulin in plants comprising:

(a) providing a chimeric nucleic acid construct comprising in the 5' to 3' direction of transcription as operably linked components:
  (i) a nucleic acid sequence capable of controlling expression in plant seed cells; and
  (ii) a nucleic acid sequence encoding an insulin polypeptide;
(b) introducing the chimeric nucleic acid construct into a plant cell; and
(c) growing the plant cell into a mature plant capable of setting seed wherein the seed expresses insulin.

In a preferred embodiment of the present invention the nucleic sequence capable of controlling expression in plant seed cells is a seed-preferred promoter, such as a phaseolin promoter.

In a preferred embodiment of the present invention insulin is expressed a manner that permits accumulation of the insulin polypeptide in a membrane enclosed intracellular compartment within the seed cells. Accordingly the present invention provides a method for the expression of insulin in plants which comprises:

(a) providing a chimeric nucleic acid construct comprising in the 5' to 3' direction of transcription as operably linked components:
  (i) a nucleic acid sequence capable of controlling expression in plant seed cells; and
  (ii) a nucleic acid sequence encoding an insulin polypeptide; and
  (iii) a nucleic acid sequence encoding a polypeptide capable of retaining the insulin polypeptide in a membrane enclosed intracellular compartment
(b) introducing the chimeric nucleic acid construct into a plant cell; and
(c) growing the plant cell into a mature plant capable of setting seed wherein the seed expresses insulin.

In a further preferred embodiment of the present invention, the membrane enclosed intracellular compartment is the endoplasmic reticulum (ER) or an ER-derived storage vesicle. Accordingly, the present invention provides a method for the expression of insulin in plants which comprises:

(a) providing a chimeric nucleic acid construct comprising in the 5' to 3' direction of transcription as operably linked components:
  (i) a nucleic acid sequence capable of controlling expression in plant seed cells; and
  (ii) a nucleic acid sequence encoding an insulin polypeptide;
  (iii) a nucleic acid sequence encoding a polypeptide capable of retaining the insulin polypeptide in the ER or in an ER derived storage vesicle
(b) introducing the chimeric nucleic acid construct into a plant cell; and
(c) growing the plant cell into a mature plant capable of setting seed wherein the seed expresses insulin.

In a further preferred embodiment the chimeric nucleic acid construct is introduced into the plant cell under nuclear genomic integration conditions. Under such conditions the chimeric nucleic acid sequence is stably integrated in the plant's genome.

In a yet further preferred embodiment the nucleic acid sequence encoding insulin is optimized for plant codon usage and the nucleic acid sequence encoding the connecting peptide (C-peptide) is shortened. Preferred nucleic acid sequences used in accordance with the present invention encode human, bovine or porcine insulin. In accordance with the present invention a nucleic acid sequence encoding a proinsulin sequence is used wherein the proinsulin is modified in that the C-peptide is shortened in length.

In another aspect, the present invention provides a method of recovering plant seeds comprising insulin. Accordingly, pursuant to the present invention a method is provided for obtaining plant seeds comprising insulin comprising:

(a) providing a chimeric nucleic acid construct comprising in the 5' to 3' direction of transcription as operably linked components:
  (i) a nucleic acid sequence capable of controlling expression in plant seed cells; and
  (ii) a nucleic acid sequence encoding an insulin polypeptide;
(b) introducing the chimeric nucleic acid construct into a plant cell;
(c) growing the plant cell into a mature plant capable of setting seed; and
(d) obtaining seeds from said plant wherein the seed comprises insulin.

Preferably, at least 0.1% of the total seed protein present in the seed is insulin.

The seeds may be used to obtain a population of progeny plants each comprising a plurality of seeds expressing insulin.

The present invention also provides plants capable of setting seed expressing insulin. In a preferred embodiment of the invention, the plants capable of setting seed comprise a chimeric nucleic acid sequence comprising in the 5' to 3' direction of transcription:

(a) a first nucleic acid sequence capable of controlling expression in a plant seed cell operatively linked to;
(b) a second nucleic acid sequence encoding an insulin polypeptide, wherein the seed contains insulin.

Preferably, at least 0.1% of the total seed protein present in the seed is insulin.

In a preferred embodiment the chimeric nucleic acid sequence is integrated in the plant's nuclear genome.

In a further preferred embodiment of the present invention the plant that is used is a safflower, a flax plant or an *Arabidopsis* plant.

In yet another aspect, the present invention provides plant seeds expressing insulin. In a preferred embodiment of the present invention, the plant seeds comprise a chimeric nucleic acid sequence comprising in the 5' to 3' direction of transcription:

(a) a first nucleic acid sequence capable of controlling expression in a plant seed cell operatively linked to;
(b) a second nucleic acid sequence encoding an insulin polypeptide.

Preferably, at least 0.1% of the total seed protein present in the seed is insulin. The seeds are a source whence the desired insulin polypeptide, which is synthesized by the seed cells, may be extracted and the insulin may be used to treat diabetic patients.

Other features and advantages of the present invention will become readily apparent from the following detailed description. It should be understood, however, that the detailed description and the specific examples while indicating preferred embodiments of the invention, are given by way of illustration only, since various changes and modifications within the spirit and scope of the invention will become readily apparent to those skilled in the art from this detailed description.

BRIEF DESCRIPTION OF THE DRAWINGS

The invention will now be described in relation to the drawings in which:

FIG. 1 depicts the nucleotide sequence (SEQ ID NO. 1) and deduced amino acid sequence (SEQ ID NO. 2) of the insulin fusion protein (PRS-D9scFv-Klip27-MI-KDEL) of pSBS4404. The predicted amino acid sequence is shown in single letter code. The deduced amino acid sequence of the PRS signal peptide is in italics, the deduced amino acid sequence of the D9 scFv is in bold, the deduced amino acid sequence of the KLIP 27 sequence is underlined, the deduced amino acid sequence of the mini-insulin sequence is in italics and bold and finally the KDEL sequence is bolded and underlined.

FIGS. 4A (Coomassie-stained gel) and 4B (corresponding Western Blot probed with anti-insulin E2E3) depicts total seed protein from wild type (wt) and transgenic seed lines expressing the 4404 and 4405 constructs. FIGS. 4C (Coomassie-stained gel) and 4D (corresponding Western Blot probed with anti-insulin E2E3) depicts oil body protein prepared from wild type and transgenic seed expressing the same 4404 and 4405 constructs. FIGS. 4E and 4F depicts the recombinant expression of insulin fusion proteins in transformed *Arabidopsis thaliana* lines (4419-9 and 4414-20) on the basis of Coomassie-stained SDS-PAGE (4E) and Western Blot analysis (4F). The molecular weight markers (M) are 10, 15, 25, 37, 50, 75, 100, 150 kDa. Controls include, hIN (recombinant human insulin standard) and hProIN (recombinant human proinsulin standard), separated under non-reducing conditions.

FIG. 5 depicts determined expression levels in the available T3 seed lines (4404-2, -17, -20, 4405-4, -13, -19) and T2 seed lines (4414-9 and -20). The levels of transgene and % molar MI expression were determined on the basis of densitometry.

DETAILED DESCRIPTION OF THE INVENTION

Figure 4:
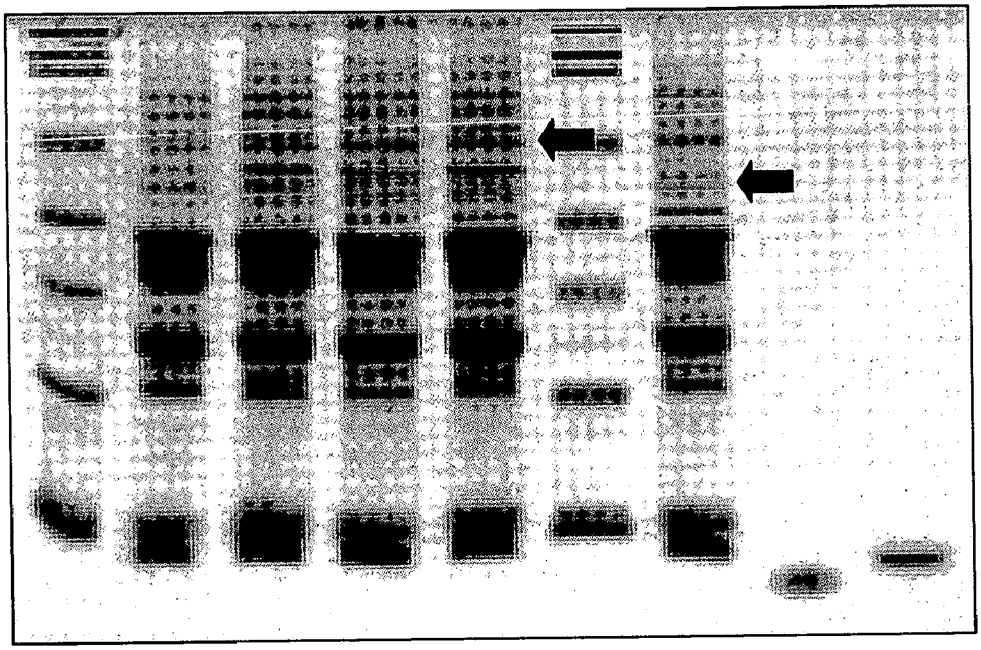
FIGS. 4(A-D) depicts recombinant expression of insulin fusion proteins in transformed *Arabidopsis thaliana* lines (4404-2, -17, -20, and 4405-4) on the basis of Coomassie-stained SDS-PAGE and Western Blot analysis. The arrows denote the position of the migrating 38.5 kDa and 34.2 kDa fusion polypeptides, PRS-D9(scfv)-KLIP27-MIw/KDEL and OLEO-KLIP8-KLIP27-MI respectively, under reducing conditions.
Figure 4:
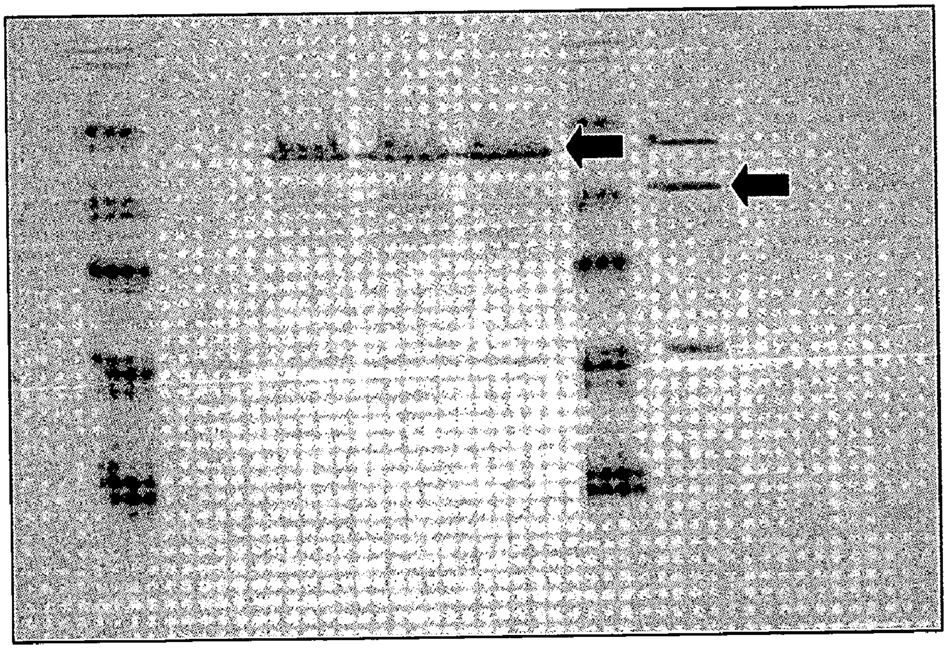
Figure 4:
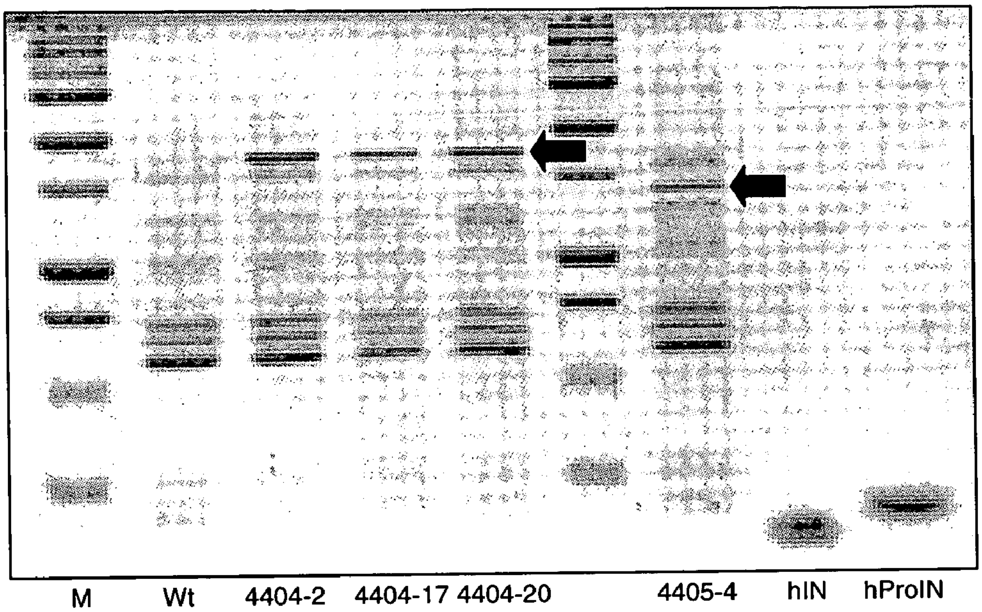

As hereinbefore mentioned, the present invention relates to improved methods for the production of insulin in transgenic plants. The present inventors have surprisingly found that levels of insulin accumulation exceeding 0.1% of total cellular protein may be achieved in plants by recombinantly producing insulin in the seeds of plants. These expression levels, which are at least ten times higher as those heretofore achieved, render commercial production of insulin in plants viable. Production in seeds offers flexibility in storage and shipment of insulin as a raw material, since insulin retains its activity upon extraction from stored seed. Furthermore, the amount of biomass that needs to be subjected to extraction is limited due to the relatively low water content present in plant seeds.

Accordingly, pursuant to the present invention a method for the expression insulin in plants is provided in which the method comprises:

(a) providing a chimeric nucleic acid construct comprising in the 5' to 3' direction of transcription as operably linked components:

(i) a nucleic acid sequence capable of controlling expression in plant seed cells; and (ii) a nucleic acid sequence encoding an insulin polypeptide;

(b) introducing the chimeric nucleic acid construct into a plant cell; and (c) growing the plant cell into a mature plant capable of setting seed wherein the seed expresses insulin.

In accordance with the present invention it has surprisingly been found that insulin accumulates to levels in plant seeds heretofore not achieved if insulin is expressed in seed in a manner that permits sequestration of the insulin polypeptide within the seed cells in a membrane enclosed intracellular compartment. Accordingly, pursuant to the present invention a preferred method for the expression of insulin in plants is provided in which the method comprises:

(a) providing a chimeric nucleic acid construct comprising in the 5' to 3' direction of transcription as operably linked components:

(i) a nucleic acid sequence capable of controlling expression in plant seed cells; and (ii) a nucleic acid sequence encoding an insulin polypeptide;

(iii) a nucleic acid sequence encoding a polypeptide capable of retaining the insulin polypeptide in a membrane enclosed intracellular compartment (b) introducing the chimeric nucleic acid construct into a plant cell; and (c) growing the plant cell into a mature plant capable of setting seed wherein the seed expresses insulin.

Terms and Definitions

Unless defined otherwise, all technical and scientific terms used herein shall have the same meaning as is commonly understood by one skilled in the art to which the present invention belongs. Where permitted, all patents, applications, published applications, and other publications, including nucleic acid and polypeptide sequences from GenBank, SwissPro and other databases referred to in the disclosure are incorporated by reference in their entirety.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The terms "nucleic acid sequence encoding insulin" and "nucleic acid sequence encoding an insulin polypeptide", which may be used interchangeably herein, refer to any and all nucleic acid sequences encoding an insulin polypeptide, including the insulin polypeptides listed in Table 1 (SEQ ID NO: 7 to 145) as well as any mammalian insulin polypeptide and any nucleic acid sequences that encode proinsulin and preproinsulin. As used herein "proinsulin" refers to an insulin polypeptide which includes the connecting peptide or "C-peptide" linking the B and A insulin polypeptide chains. In native human insulin the C-peptide is the 31 amino acid residue polypeptide chain connecting residue B30 to residue A1. The term "preproinsulin" refers to a proinsulin molecule additionally comprising an N-terminal signal sequence which directs translation to occur on the ER ribosomes. Nucleic acid sequences encoding an insulin polypeptide further include any and all nucleic acid sequences which (i) encode polypeptides that are substantially identical to the insulin polypeptide sequences set forth herein; or (ii) hybridize to any nucleic acid sequences set forth herein under at least moderately stringent hybridization conditions or which would hybridize thereto under at least moderately stringent conditions but for the use of synonymous codons.

By the term "substantially identical" it is meant that two polypeptide sequences preferably are at least 75% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, preferably using the Clustal W algorithm (Thompson, J D, Higgins D G, Gibson T J, 1994, Nucleic Acids Res. 22 (22): 4673-4680, together with BLOSUM 62 scoring matrix (Henikoff S. and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403).

By "At least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the $T_m$, which in sodium containing buffers is a function of the sodium ion concentration and temperature ($T_m$=81.5° C.−16.6($Log_{10}$[$Na^+$])+0.41(%(G+C)−600/1), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in $T_m$, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at $T_m$−5° C. based on the above equation , followed by a wash of 0.2×SSC/0.1% SDS at 60° C . Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

As used herein the terms "insulin" and "insulin polypeptide", which may be used interchangeable herein, refer to any and all insulin polypeptides including the insulin polypeptides listed in Table 1 (SEQ ID NO: 7 to 145) as well as a polypeptide molecule comprising a sequence of amino acid residues which is (i) substantially identical to the amino acid sequences constituting any insulin polypeptides set forth herein or (ii) encoded by a nucleic acid sequence capable of hybridizing under at least moderately stringent conditions to any nucleic acid sequence encoding insulin set forth herein or capable of hybridizing under at least moderately stringent conditions to any nucleic acid sequence encoding insulin set forth herein but for the use of synonymous codons. The terms insulin and insulin polypeptide include pro-insulin polypeptides and mini-insulin polypeptides. The insulin polypeptide is preferably of human, porcine or bovine origin.

The term "polypeptide capable of retaining the insulin polypeptide within a membrane enclosed intracellular compartment" as used herein refers to any polypeptide, which when linked to an insulin polypeptide, is capable of sequestering the insulin polypeptide in a subcellular structure surrounded by a membrane and located within the intracellular space of the plant cell as defined by the plant cell's plasma membrane.

The term "a polypeptide capable of retaining the insulin polypeptide in the ER or in an ER derived storage vesicle" as used herein refers to any polypeptide, which when linked to an insulin polypeptide is capable of sequestering the insulin polypeptide either in the endoplasmic reticulum or in a storage compartment which is derived from an endoplasmic reticulum, such as for example an oil body, within a plant cell.

The term "oil body" or "oil bodies" as used herein refers to any oil or fat storage organelle in a plant seed cell (described in for example: Huang (1992) Ann. Rev. Plant Mol. Biol. 43: 177-200).

The term "chimeric" as used herein in the context of nucleic acid sequences refers to at least two linked nucleic acid sequences which are not naturally linked. Chimeric nucleic acid sequences include linked nucleic acid sequences of different natural origins. For example a nucleic acid sequence constituting a plant promoter linked to a nucleic acid sequence encoding human insulin is considered chimeric. Chimeric nucleic acid sequences also may comprise nucleic acid sequences of the same natural origin, provided they are not naturally linked. For example a nucleic acid sequence constituting a promoter obtained from a particular cell-type may be linked to a nucleic acid sequence encoding a polypeptide obtained from that same cell-type, but not normally linked to the nucleic acid sequence constituting the promoter. Chimeric nucleic acid sequences also include nucleic acid sequences comprising any naturally occurring nucleic acid sequence linked to any non-naturally occurring nucleic acid sequence.

Preparation of Recombinant Expression Vectors Comprising Chimeric Nucleic Acid Sequences Encoding Insulin and a Promoter Capable of Controlling Expression in a Plant Seed Cell The nucleic acid sequences encoding insulin that may be used in accordance with the methods and compositions provided herein may be any nucleic acid sequence encoding an insulin polypeptide, including any proinsulin and preproinsulin.

Exemplary nucleic acid sequences encoding insulin are well known to the art and are generally readily available from a diverse variety of mammalian sources including human (Bell, G. I. et al., 1980, Nature 284:26-32), porcine (Chance, R. E. et al., 1968, Science 161:165-167), bovine (D'Agostino, J. et al., 1987, Mol. Endocrinol. 1:327-331), ovine (Peterson, J. D. et al., 1972, Biol. Chem. 247:4866-4871) and the like, as well as from plant sources (Oliveira, A. E. A. et al., 1999, Protein Pept. Lett. 6:15-21). Insulin encoding sequences that may used include those encoding polypeptide chains set forth as SEQ ID NO:7 to SEQ ID NO:145. The respective corresponding nucleic acid sequences encoding the insulin polypeptide chains can be readily identified via the Swiss Protein identifier numbers provided in Table 1. Using these nucleic acid sequences, additional novel insulin encoding nucleic acid sequences may be readily identified using techniques known to those of skill in the art. For example libraries, such as expression libraries, cDNA and genomic libraries, may be screened, and databases containing sequence information from sequencing projects may be searched for similar sequences. Alternative methods to isolate additional nucleic acid sequences encoding insulin polypeptides may be used, and novel sequences may be discovered and used in accordance with the present invention. In preferred embodiments nucleic acid sequences encoding insulin are human, porcine and bovine insulin.

Numerous insulin analogs are known to the prior art (see for example U.S. Pat. Nos. 5,461,031; 5,474,978; 5,164,366 and 5,008,241) and may be used in accordance with the present invention. Analogs that may be used herein include human insulin molecules in which amino acid residue 28 of the B-chain (B28) has been changed from its natural proline residue into aspartate, lysine or isoleucine. In another embodiment the lysine residue at B29 is modified to a proline. Furthermore, the aspargine at A21 may be changed to alanine, glutamine, glutamate, glycine, histidine, isoleucine, leucine, methionine, serine, threonine, tryptophan, tyrosine or valine. Also, aspargine at B3 may be modified to lysine. Further examples of insulin analogs that may used herein include: human insulin lacking the B30 residue, also frequently referred to as "desB30" or "B(1-29)"; those lacking the last 3 amino acid residues insulin "B(1-27)"; insulin molecules lacking the phenylalanine residue at B1; and analogs wherein the A-chain or the B-chain have an N-terminal or C-terminal extension, for example the B-chain may be N-terminally extended by the addition of two arginine residues.

In preferred embodiments, the nucleic acid sequence encoding insulin that is used is proinsulin. In further preferred embodiments nucleic acid sequence molecules encoding insulin are used in which the C-peptide has been modified relative to its native form. Amino acid residues in the C-peptide may be substituted and the C-peptide may be lengthened or shortened. In this regard, as used herein the term "mini-insulin" refers to an insulin polypeptide which has been modified so that the C-peptide has been shortened in length relative to its native form. In preferred embodiments a mini-insulin is used. Preferably the C-peptide of a mini-insulin molecule will be shorter than 20 amino acid residues, more preferably shorter than 15 amino acid residues and most preferably shorter than 9 amino acid residues, for example 7, 5, or 3 residues. Preferably, as is the case with natural insulin molecules, the mini-insulin C-peptide will comprise a cleavage site at its C- and N-termini. Such cleavage sites may be any convenient sites known to the art, for example methionine, cleavable by cyanogen bromide, a single basic residue or a pair of basic residues, cleavable by trypsin or trypsin like proteases or by a carboxy-peptidase. For example, the C-peptide may comprise a C-terminal lysine, for example Ala-Ala-Lys (SEQ ID NO:146), or a dibasic processing site immediately prior to the GlyA1 residue, for example Asn-Lys-Arg (SEQ ID NO:147), or Arg-Arg-Lys-Gln-Lys-Arg. (SEQ ID NO:148) or a tetrabasic processing site immediately prior to the Gly A1 residue, for example Arg-Arg-Lys-Arg (SEQ ID NO:149). Accordingly, mini-insulin molecules that may be used in accordance with the present invention include:

$$B(1\text{-}29/30)\text{-}X_1\text{-}X_2\text{-}X_3\text{-}Y_1\text{-}A(1\text{-}21)$$

wherein $X_1$ is any amino acid;

$X_2$ is any amino acid;

$X_3$ is Lys or Arg;

$Y_1$ is peptide bond or 1-17 amino acid residues;

B(1-29/30) is the B chain of the human insulin B-chain containing amino acid residues 1-29 or 1-30; and A(1-21) is the A chain of the human insulin A-chain containing amino acid residues 1-21.

In a preferred embodiment, $X_1$ is a basic amino acid residue (Lys or Arg) and $Y_1$ is either a peptide bond or 1-17 amino acid residues where the C-terminal residue is a basic amino acid residue (Lys or Arg).

Further, mini-insulin molecules that may be used herein comprise those that may be represented by the formula:

$$B(1\text{-}27)\text{-}X_2\text{-}X_3\text{-}X_1\text{-}Y\text{-}A(1\text{-}21)$$

wherein $X_1$ is a peptide of 1-8 amino acid residues comprising at least one aromatic amino acid residue;

$X_2$ is one of Pro, Asp, Lys or Ile at position 28 of the B-chain;

$X_3$ is one of Pro, Lys, Ala, Arg or Pro-Thr at position 29 of the B-chain;

Y is Lys or Arg;

B(1-27) is the B chain of the human insulin B-chain containing amino acid residues 1-27; and A(1-21) is the A chain of the human insulin A-chain containing amino acid residues 1-21.

Additional examples of nucleic acid molecules encoding a mini-insulin polypeptides that may be used in accordance with the present invention include those described in: Markussen et al., Walter de Gruyter & Co. 1987, in: Peptides pp 189-194; Thim et al., 1989, in: Genetics and molecular biology of industrial microorganisms, American Society for Microbiology pp 322-328; and those set forth in U.S. Pat. Nos. 4,916,212; 5,324,641 and 6,521,738. Alterations to the nucleic acid sequence encoding insulin to prepare insulin analogs may be made using a variety of nucleic acid modification techniques known to those skilled in the art, including for example site directed mutagenesis, targeted mutagenesis, random mutagenesis, the addition of organic solvents, gene shuffling or a combination of these and other techniques known to those of skill in the art (Shraishi et al., 1988, Arch. Biochem. Biophys, 358: 104-115; Galkin et al., 1997, Protein Eng. 10: 687-690; Carugo et al., 1997, Proteins 28: 10-28; Hurley et al., 1996, Biochem, 35: 5670-5678; Holmberg et al., 1999, Protein Eng. 12: 851-856).

In accordance with the present invention it has surprisingly been found that insulin accumulates to levels in plant seeds heretofore not achieved if the insulin is expressed in seed, preferably in such a manner that the insulin polypeptide within the seed cells is sequestered in a membrane enclosed intracellular compartment. In preferred embodiments of the present invention the insulin polypeptide is sequestered in the ER or in an ER derived storage vesicle. In order to achieve such sequestration of insulin in the ER or an ER derived storage vesicle, in accordance with the present invention, the polypeptide encoding insulin is linked to a polypeptide which causes the insulin polypeptide to be retained in the ER or in an ER-derived storage vesicle rather than being transported out of the ER to, for example, the apoplast. Polypeptides that may be used in accordance with the present invention to retain the insulin polypeptide in the ER include any polypeptide capable of sequestering the insulin in the ER. Such polypeptides may be synthesized or obtained from any biological source. In a preferred embodiment of the present invention, the polypeptide that is capable of retaining the insulin is a polypeptide comprising a C-terminal ER retention motif. Examples of such C-terminal ER retention motifs include KDEL, HDEL, DDEL, ADEL and SDEL sequences (SEQ ID NO:150 to 154 respectively). Other examples include HDEF (SEQ ID NO:155) (Lehmann et al., 2001. Plant Physiol 127 (2): 436-49.), or two arginine residues close to the N-terminus located at positions 2 and 3, 3 and 4, or 4 and 5 (Abstract from Plant Biology 2001 Program, ASPB, July 2001, Providence, R.I., USA). Nucleic acid sequences encoding a C-terminal ER retention motif are preferably linked to the nucleic acid sequence encoding the insulin polypeptide in such a manner that the polypeptide capable of retaining the insulin in the ER is linked to the C-terminal end of the insulin polypeptide.

In order to achieve sequestration of the insulin polypeptide in an ER derived storage vesicle, the insulin polypeptide is linked to a polypeptide that is capable of retaining the insulin polypeptide in an ER derived storage vesicle. The polypeptide capable of retaining the insulin polypeptide in an ER-derived storage vesicle that may be used in accordance with the methods herein may be any polypeptide capable of sequestering the insulin polypeptide in an ER-derived storage vesicle. Polypeptides capable of retaining insulin in an ER derived storage vesicle may be synthesized or obtained from any biological source. In a preferred embodiment the ER-derived storage vesicle is an oil body and the insulin polypeptide is linked to an oil body protein or a sufficient portion thereof capable of retaining the insulin polypeptide in the ER-derived storage vesicle. Oil body proteins that may be used in this regard include any protein that naturally associates with an oil body. Oil body proteins that are particularly preferred are oleosins, for example an *Arabidopsis* oleosin (van Rooijen et al. (1991) Plant Mol Biol. 18: 1177-1179) corn oleosin (Bowman-Vance et al., 1987, J. Biol. Chem. 262: 11275-11279; Qu et al., 1990, J. Biol. Chem. 265: 2238-

2243), carrot oleosin (Hatzopoulos et al. (1990) Plant Cell 2: 457-457) or *Brassica* oleosin (Lee et al., 1991, Plant Physiol. 96: 1395-1397), caleosins, see for example Genbank accession number AF067857) and steroleosins (Lin et al., 2002 Plant Physiol. 128(4):1200-11). In a further preferred embodiment, the oil body protein is a plant oleosin and shares sequence similarity with other plant oleosins such as the oleosin isolated from *Arabidopsis thaliana* (SEQ ID NO:156) or *Brassica napus* (SEQ ID NO:157). In another embodiment, the oil body protein is a caleosin or calcium binding protein from plant, fungal or other sources and shares sequence homology with plant caleosins such as the caleosin isolated from *Arabidopsis thaliana* (SEQ ID NO:158 and -SEQ ID NO:159) In another embodiment the oil body protein is a steroleosin (SEQ ID NO:160), a sterol binding dehydrogenase (Lin L-J et al, (2002) Plant Physiol 128: 1200-1211). The polypeptide encoding insulin may be linked to the oil body protein to the N-terminus as well as to the C-terminus and to fragments of an oil body protein, such as for example the central domain of an oleosin. New oil body proteins may be discovered for example by preparing oil bodies (for methodologies to prepare oil bodies see for example U.S. Pat. No. 6,650,554) and identifying proteins in oil body preparations through for example SDS gel electrophoresis. Polyclonal antibodies may be raised against these proteins and used to screen cDNA libraries in order to identify nucleic acid sequences encoding oil body proteins. New oil body proteins further may be discovered using known nucleic acid sequences encoding oil body proteins, using for example the hereinbefore mentioned oil body protein sequences encoding oil body proteins, to probe for example cDNA or genomic libraries for the presence of oil body proteins.

Polypeptides capable of retaining the insulin in the ER or an ER derived storage organelle are typically not cleaved and the insulin may accumulate in the form of a fusion protein, which is, for example, typically the case when a KDEL retention signal is used to retain the polypeptide in the ER or when an oil body protein is used to retain the polypeptide in an ER derived storage organelle.

The chimeric nucleic acid sequence additionally may contain a nucleic sequence which targets the nucleic acid sequence to the endomembrane system ("signal peptide"). In embodiments of the present invention in which the insulin polypeptide is retained in the ER using a sequence capable of retaining the polypeptide in the ER, such as KDEL, HDEL or SDEL polypeptide, it is particularly desirable to include a nucleic acid sequence encoding a signal peptide. Exemplary signal peptides that may be used herein include the tobacco pathogenesis related protein (PR-S) signal sequence (SE-Q.ID.NO:161) (Sijmons et al., 1990, Bio/technology, 8:217-221), lectin signal sequence (Boehn et al., 2000, Transgenic Res, 9(6):477-86), signal sequence from the hydroxyproline-rich glycoprotein from *Phaseolus vulgaris* (Yan et al., 1997, Plant Phyiol. 115(3):915-24 and Corbin et al., 1987, Mol Cell Biol 7(12):4337-44), potato patatin signal sequence (Iturriaga, G et al., 1989, Plant Cell 1:381-390 and Bevan et al., 1986, Nuc. Acids Res. 41:4625-4638.) and the barley alpha amylase signal sequence (Rasmussen and Johansson, 1992, Plant Mol. Biol. 18(2):423-7). Such targeting signals may in vivo be cleaved off from the insulin sequence, which for example is typically the case when an apoplast targeting signal, such as the tobacco pathogenesis related protein-S (PR-S) signal sequence (Sijmons et al., 1990, Bio/technology, 8:217-221) is used. Other signal peptides can be predicted using the SignalP World Wide Web server (http://www.cbs.dtu.dk/services/SignalIP/) which predicts the presence and location of signal peptide cleavage sites in amino acid sequences-from different organisms. In general there is little conservation of the primary amino acid sequence, although general physiochemical properties are conserved to some extent. The generic structure of signal peptides has 3 regions, the short amino-terminal "n-region" contains positively charged residues, the central hydrophobic "h-region" ranges in size from 7 to 15 amino acids and the carboxy-terminal "c-region" contains polar amino acids and a cleavage site that is recognized by membrane bound signal peptidase enzymes (Nakai K., 2000, Advances in Protein Chem 54:277-344). A targeting signal that also may be used in accordance herewith includes the native insulin signal sequence (24 amino acids in length in case of the human sequence). In preferred embodiments hereof an N-terminally located apoplast targeting sequence, such as the hereinbefore mentioned tobacco PR-S sequence is used combined with a C-terminally located ER retention sequence such as the KDEL sequence.

In a further preferred embodiment, a nucleic acid sequence encoding a yeast α-factor leader sequence is linked to the N-terminal end of the nucleic acid sequence encoding insulin. Yeast leader sequences or sequences derived from yeast leader sequences that may be used in accordance herewith include those listed in SEQ ID NO:162 to SEQ ID NO:171 (Kjeldsen et al., 2001, Biotechnology and Genetic Engineering Reviews 18: 89-121). Such leader sequences may further comprise a spacer peptide located C-terminally of the nucleic acid encoding the leader sequence and N-terminally of the sequence encoding insulin. In accordance herewith such spacer sequences typically are between 2 and 20 amino acids in length. Thus, for example, spacer sequences SEQ ID NO:172 and SEQ ID NO:173 (Kjeldsen et al., 2001, Biotechnology and Genetic Engineering Reviews 18: 89-121) may be used. In embodiments of the present invention in which a yeast leader sequence is used, the nucleic acid sequence encoding the insulin polypeptide is preferably a mini-insulin polypeptide. In accordance herewith, in a particularly preferred embodiment a nucleic acid sequence encoding a single-chain antibody linked to a nucleic acid sequence encoding a yeast secretion leader peptide is used, as further described in Example 1 hereof.

The chimeric nucleic acid sequence may also comprise polypeptides resulting in N-and/or C-terminal stabilizing protein extensions. Such extensions may be used to stabilize and/or assist in folding of the insulin polypeptide chain and additionally may be used to facilitate purification of insulin. Polypeptide extensions that may be used in this regard include for example a nucleic acid sequence encoding a single chain antibody, a nucleic acid encoding an Affibody® molecule (Affibody AB), a nucleic acid sequence encoding the non-toxic B subunit of cholera toxin (CTB) (Arakawa, T. et al., 1998, Nat. Biotechnol. 16:938) or combinations of such polypeptides. In a particularly preferred embodiment, the insulin polypeptide is retained in a membrane enclosed compartment, such as the ER, using for example a KDEL sequence as hereinbefore described, combined with a stabilizing polypeptide that permits the association of the insulin polypeptide with an oil body upon breakage of the integrity of the plant cell such as will occur when the insulin polypeptide is recovered from the plant cell. An example of such a stabilizing polypeptide is a single chain antibody with specificity for an oil body. Nucleic acid sequences encoding single chain antibodies with specificity for an oil body may be prepared from hybridoma cell lines expressing monoclonal antibodies raised against an oil body protein. In one embodiment, the single chain antibody specifically binds an oleosin, as described by Alting-Mees et al. (2000) IBC's International Conference on Antibody Engineering, Poster #1. This embodiment of the present invention is further detailed in Example 1 hereof.

In a further embodiment, a cleavage site may be located upstream of the N-terminus and downstream the C-terminus of the insulin allowing for the insulin polypeptide to be cleaved from the fusion partner, thereby obtaining isolated insulin. Examples of such cleavage sites can be found in WO 98/49326 (Method for the cleavage of fusion proteins) and related applications and LaVallie et al. (1994) Enzymatic and chemical cleavage of fusion proteins In Current Protocols in Molecular Biology pp 16.4.5-16.4.17, John Wiley and Sons, Inc., New York N.Y. In a preferred embodiment, the cleavage site is a tetrabasic linker (for example Arg-Arg-Lys-Arg-SEQ ID NO:149) which is cleavable by trypsin. In a further preferred embodiment, the cleavage site is KLIP 8 (SEQ ID NO:174) which is cleavable by aspartic proteases including chymosin.

The invention further provides methods for the separation of heterologous proteins from host cell components by partitioning of the oil body fraction and subsequent release of the heterologous protein via specific cleavage of the heterologous protein—oil body protein fusion. Optionally a cleavage site may be located upstream of the N-terminus and downstream of the C-terminus of the heterologous polypeptide allowing the fusion polypeptide to be cleaved and separated by phase separation into its component peptides.

The nucleic acid sequence encoding insulin may be altered, to further improve expression levels for example, by optimizing the nucleic acid sequence in accordance with the preferred codon usage for a particular plant cell type which is selected for the expression of the insulin polypeptide, or by altering motifs known to destabilize mRNAs (see for example: PCT Patent Application 97/02352). Comparison of the codon usage of the nucleic acid sequence encoding the insulin polypeptide with the codon usage of the plant cell type will enable the identification of codons that may be changed. Construction of synthetic genes by altering the codon usage is described in for example PCT Patent Application 93/07278.

In a preferred embodiment, the nucleic acid sequence encoding insulin that is used is represented by SEQ ID NO:1, SEQ ID NO:3, SEQ ID NO:5, or SEQ ID NO:195.

In accordance herewith the nucleic acid sequence encoding insulin is linked to a promoter capable of controlling expression of the insulin polypeptide in a plant seed cell. Accordingly, the present invention also provides a nucleic acid sequence encoding insulin linked to a promoter capable of controlling expression in a plant seed cell. Promoters that may be used herein will be generally art recognized and include any plant derived promoter capable of controlling expression of polypeptides in plants. Generally, promoters obtained from dicotyledonous plant species will be used when a dicotyledonous plant is selected in accordance herewith, while a monocotyledonous plant promoter will be used when a monocotyledonous plant species is selected. Constitutive promoters that may be used include, for example, the 35S cauliflower mosaic virus (CaMV) promoter (Rothstein et al., 1987, Gene 53: 153-161), the rice actin promoter (McElroy et al., 1990, Plant Cell 2: 163-171; U.S. Pat. No. 6,429,357), a ubiquitin promoter, such as the corn ubiquitin promoter (U.S. Pat. Nos. 5,879,903; 5,273,894), and the parsley ubiquitin promoter (Kawalleck, P. et al., 1993, Plant Mol. Biol. 21:673-684).

In preferred embodiments, the promoter that is used is a promoter which results in preferential expression of the insulin polypeptide in seed tissue. “Seed-preferred promoters” in this regard are promoters which control expression of a recombinant protein (i.e. insulin) so that preferably at least 80% of the total amount of recombinant protein present in the mature plant is present in the seed. More preferably at least 90% of the total amount of recombinant protein present in the mature plant is present in the seed. Most preferably at least 95% of the total amount of recombinant protein present in the mature plant is present in the seed. Seed-preferred promoters that may be used in this regard include, for example, the bean phaseolin promoter (Sengupta-Gopalan et al., 1985, Proc. Natl. Acad. Sci. USA 82: 3320-3324); the *Arabidopsis* 18 kDa oleosin promoter (U.S. Pat. No. 5,792,922) or the flax oleosin promoter (WO 01/16340); the flax legumin like seed storage protein (linin) promoter (WO 01/16340); the flax 2S storage protein promoter (WO 01/16340); an endosperm preferred promoter such as the Amy32b promoter (Rogers and Milliman, J. Biol. Chem., 1984, 259: 12234-12240, the Amy6-4 promoter (Kursheed and Rogers, J. Biol. Chem., 1988, 263: 18953-18960 or the Aleurain promoter (Whittier et al., 1987, Nucleic Acids Res., 15: 2515-2535) or the bean arcelin promoter (Jaeger G D, et al., 2002, Nat. Biotechnol. Dec; 20:1265-8). New promoters useful in various plants are constantly discovered. Numerous examples of plant promoters may be found in Ohamuro et al. (Biochem. of Plnts., 1989, 15: 1-82).

Certain genetic elements capable of enhancing expression of the insulin polypeptide may be used herein. These elements include the untranslated leader sequences from certain viruses, such as the AMV leader sequence (Jobling and Gehrke, 1987, Nature, 325: 622-625) and the intron associated with the maize ubiquitin promoter (U.S. Pat. No. 5,504,200). Generally the chimeric nucleic acid sequence will be prepared so that genetic elements capable of enhancing expression will be located 5' to the nucleic acid sequence encoding the insulin polypeptide.

In accordance with the present invention the chimeric nucleic acid sequences comprising a promoter capable of controlling expression in plant seeds linked to a nucleic acid sequence encoding an insulin polypeptide can be integrated into a recombinant expression vector which ensures good expression in the seed cell. Accordingly, the present invention includes a recombinant expression vector comprising in the 5' to 3' direction of transcription as operably linked components:

(i) a nucleic acid sequence capable of controlling expression in plant seed cells; and (ii) a nucleic acid sequence encoding an insulin polypeptide;

wherein the expression vector is suitable for expression in a seed cell. The term “suitable for expression in a seed cell” means that the recombinant expression vector comprises the chimeric nucleic acid sequence of the present invention linked to genetic elements required to achieve expression in a seed cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the plant cell's nuclear genome, for example the T-DNA left and right border sequences which facilitate the integration into the plant's nuclear genome in embodiments of the invention in which plant cells are transformed using *Agrobacterium*.

As hereinbefore mentioned, the recombinant expression vector generally comprises a transcriptional terminator which besides serving as a signal for transcription termination further may serve as a protective element capable of extending the mRNA half life (Guarneros et al., 1982, Proc. Natl. Acad. Sci. USA, 79: 238-242). The transcriptional terminator is generally from about 200 nucleotides to about 1000 nucleotides and the expression vector is prepared so that the transcriptional terminator is located 3' of the nucleic acid sequence encoding insulin. Termination sequences that may be used herein include, for example, the nopaline termination region (Bevan et al., 1983, Nucl. Acids. Res., 11: 369-385), the phaseolin terminator (van der Geest et al., 1994, Plant J. 6: 413-423), the arcelin terminator ((Jaeger G D, et al., 2002, Nat. Biotechnol.Dec; 20:1265-8)), the terminator for the octopine synthase genes of *Agrobacterium tumefaciens* or other similarly functioning elements. Transcriptional terminators may be obtained as described by An (An, 1987, Methods in Enzym. 153: 292).

Pursuant to the present invention the expression vector may further contain a marker gene. Marker genes that may be used in accordance with the present invention include all genes that allow the distinction of transformed cells from non-transformed cells, including all selectable and screenable marker genes. A marker gene may be a resistance marker such as an antibiotic resistance marker against, for example, kanamycin (U.S. Pat. No. 6,174,724), ampicillin, G418, bleomycin, hygromycin which allows selection of a trait by chemical means or a tolerance marker against a chemical agent, such as the normally phytotoxic sugar mannose (Negrotto et al., 2000, Plant Cell Rep. 19: 798-803). Other convenient markers that may be used herein include markers capable of conveying resistance against herbicides such as glyphosate (U.S. Pat. Nos. 4,940,935; 5,188,642), phosphinothricin (U.S. Pat. No. 5,879,903) or sulphonyl ureas (U.S. Pat. No. 5,633,437). Resistance markers, when linked in close proximity to nucleic acid sequence encoding the insulin polypeptide, may be used to maintain selection pressure on a population of plant cells or plants that have not lost the nucleic acid sequence encoding the insulin polypeptide. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

Recombinant vectors suitable for the introduction of nucleic acid sequences into plants include *Agrobacterium* and *Rhizobium* based vectors, such as the Ti and Ri plasmids, including for example pBIN19 (Bevan, Nucl. Acid. Res., 1984, 22: 8711-8721), pGKB5 (Bouchez et al., 1993, C R Acad. Sci. Paris, Life Sciences, 316:1188-1193), the pCGN series of binary vectors (McBride and Summerfelt, 1990, Plant Mol. Biol., 14:269-276) and other binary vectors (e.g. U.S. Pat. No. 4,940,838).

The recombinant expression vectors, nucleic acid sequences and chimeric nucleic acid sequences of the present invention may be prepared in accordance with methodologies well known to those skilled in the art of molecular biology. Such preparation will typically involve the bacterial species *Escherichia coli* as an intermediary cloning host. The preparation of the *E. coli* vectors as well as the plant transformation vectors may be accomplished using commonly known techniques such as restriction digestion, ligation, gel ectrophoresis, DNA sequencing, the Polymerase Chain Reaction (PCR) and other methodologies. These methodologies permit the linking of nucleic acid sequences and polypeptides to which the present invention pertains. A wide variety of cloning vectors is available to perform the necessary steps required to prepare a recombinant expression vector. Among the vectors with a replication system functional in *E. coli,* are vectors such as pBR322, the pUC series of vectors, the M13mp series of vectors, pBluescript etc. Typically, these cloning vectors contain a marker allowing selection of transformed cells. Nucleic acid sequences may be introduced in these vectors, and the vectors may be introduced in *E. coli* grown in an appropriate medium. Recombinant expression vectors may readily be recovered from cells upon harvesting and lysing of the cells. Further, general guidance with respect to the preparation of recombinant vectors may be found in, for example: Sambrook et al., Molecular Cloning, a Laboratory Manual, Cold Spring Harbor Laboratory Press, 1989, Vol. 3.

Preparation of Plants Comprising Seeds Capable of Expressing Insulin

In accordance with the present invention the chimeric nucleic acid sequence is introduced into a plant cell and the cells are grown into mature plants capable of setting seed, wherein the seed expresses the insulin polypeptide.

In accordance herewith any plant species or plant cell may be selected. Particular cells used herein include cells obtainable from *Arabidopsis thaliana,* Brazil nut (*Betholettia excelsa*); castor bean (*Riccinus communis*); coconut (*Cocus nucifera*); coriander (*Coriandrum sativum*); cotton (*Gossypium* spp.); groundnut (*Arachis Hypogaea*); jojoba (*Simmondsia chinensis*); linseed/flax (*Linum usitatissimum*); maize (*Zea mays*); mustard (*Brassica* spp. and *Sinapis alba*); oil palm (*Elaeis guineeis*); olive (*Olea eurpaea*); rapeseed (*Brassica* spp.); rice (*Oryza sativa*); safflower (*Carthamus tinctorius*); soybean (*Glycine max*); squash (*Cucurbita maxima*); barley (*Hordeum vulgare*); wheat (*Traeticum aestivum*); and sunflower (*Helianthus annuus*).

In accordance herewith in a preferred embodiment plant species or plant cells from oil seed plants are used. Oil seed plants that may be used herein include peanut (*Arachis hypogaea*); mustard (*Brassica* spp. and *Sinapis alba*); rapeseed (*Brassica* spp.); chickpea (*Cicer arietinum*); soybean (*Glycine max*); cotton (*Gossypium hirsutum*); sunflower (*Helianthus annuus*); (*Lentil Lens culinaris*); linseed/flax (*Linum usitatissimum*); white clover (*Trifolium repens*); olive (*Olea eurpaea*); oil palm (*Elaeis guineeis*); safflower (*Carthamus tinctorius*) and narbon bean (*Vicia narbonensis*).

In accordance herewith in a particularly preferred embodiment safflower, *Arabidopsis* or flax is used.

Methodologies to introduce plant recombinant expression vectors into a plant cell, also referred to herein as "transformation", are well known to the art and typically vary depending on the plant cell that is selected. General techniques to introduce recombinant expression vectors in cells include, electroporation; chemically mediated techniques, for example $CaCl_2$ mediated nucleic acid uptake; particle bombardment (biolistics); the use of naturally infective nucleic acid sequences, for example virally derived nucleic acid sequences, or *Agrobacterium* or *Rhizobium* derived sequences, polyethylene glycol (PEG) mediated nucleic acid uptake, microinjection and the use of silicone carbide whiskers.

In preferred embodiments, a transformation methodology is selected which will allow the integration of the chimeric nucleic acid sequence in the plant cell's genome, and preferably the plant cell's nuclear genome. In accordance herewith this is considered particularly desirable as the use of such a methodology will result in the transfer of the chimeric nucleic acid sequence to progeny plants upon sexual reproduction. Transformation methods that may be used in this regard include biolistics and *Agrobacterium* mediated methods.

Transformation methodologies for dicotyledenous plant species are well known. Generally, *Agrobacterium* mediated transformation is used because of its high efficiency, as well as the general susceptibility by many, if not all, dicotyledenous plant species. *Agrobacterium* transformation generally involves the transfer of a binary vector, such as one of the hereinbefore mentioned binary vectors, comprising the chimeric nucleic acid sequence of the present invention from *E. coli* to a suitable *Agrobacterium* strain (e.g. EHA101 and LBA4404) by, for example, tri-parental mating with an *E. coli* strain carrying the recombinant binary vector and an *E. coli* strain carrying a helper plasmid capable of mobilizing the binary vector to the target *Agrobacterium* strain, or by DNA transformation of the *Agrobacterium* strain (Hofgen et al., Nucl. Acids Res., 1988, 16:9877). Other techniques that may be used to transform dicotyledenous plant cells include biolistics (Sanford, 1988, Trends in Biotechn. 6:299-302); electroporation (Fromm et al., 1985, Proc. Natl. Acad. Sci. USA., 82:5824-5828); PEG mediated DNA uptake (Potrykus et al., 1985, Mol. Gen. Genetics, 199:169-177); microinjection (Reich et al., Bio/Techn., 1986, 4:1001-1004); and silicone carbide whiskers (Kaeppler et al., 1990, Plant Cell Rep., 9:415-418) or in planta transformation using, for example, a flower dipping methodology (Clough and Bent, 1998, Plant J., 16:735-743).

Monocotyledonous plant species may be transformed using a variety of methodologies including particle bombardment (Christou et al., 1991, Biotechn. 9:957-962; Weeks et al., Plant Physiol., 1993, 102:1077-1084; Gordon-Kamm et al., Plant Cell, 1990, 2:5603-618); PEG mediated DNA uptake (European Patents 0292 435; 0392 225) or *Agrobacterium* mediated transformation (Goto-Fumiyuki et al., 1999, Nature-Biotech. 17:282-286).

The exact plant transformation methodology may vary somewhat depending on the plant species and the plant cell type (e.g. seedling derived cell types such as hypocotyls and cotyledons or embryonic tissue) that is selected as the cell target for transformation. As hereinbefore mentioned in a particularly preferred embodiment safflower, *Arabidopsis* or flax is used. A methodology to obtain safflower transformants is available in Baker and Dyer (Plant Cell Rep., 1996, 16:106-110). Additional plant species specific transformation protocols may be found in: Biotechnology in Agriculture and Forestry 46: Transgenic Crops I (Y. P. S. Bajaj ed.), Springer-Verlag, New York (1999), and Biotechnology in Agriculture and Forestry 47: Transgenic Crops II (Y. P. S. Bajaj ed.), Springer-Verlag, New York (2001).

Following transformation, the plant cells are grown and upon the emergence of differentiating tissue, such as shoots and roots, mature plants are regenerated. Typically a plurality of plants is regenerated. Methodologies to regenerate plants are generally plant species and cell type dependent and will be known to those skilled in the art. Further guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

In one aspect, the present invention provides a method of recovering plant seeds comprising insulin. Accordingly, the present invention provides a method for obtaining plant seeds comprising insulin comprising:

(a) providing a chimeric nucleic acid construct comprising in the 5' to 3' direction of transcription as operably linked components:
   (i) a nucleic acid sequence capable of controlling expression in plant seed cells; and
   (ii) a nucleic acid sequence encoding an insulin polypeptide;
(b) introducing the chimeric nucleic acid construct into a plant cell;
(c) growing the plant cell into a mature plant capable of setting seed; and
(d) obtaining seeds from said plant wherein the seed comprises insulin.

In preferred embodiments, a plurality of transformed plants is obtained, grown, and screened for the presence of the desired chimeric nucleic acid sequence, the presence of which in putative transformants may be tested by, for example, growth on a selective medium, where herbicide resistance markers are used, by direct application of the herbicide to the plant, or by Southern blotting. If the presence of the chimeric nucleic acid sequence is detected, transformed plants may be selected to generate progeny and ultimately mature plants comprising a plurality of seeds comprising the desired chimeric nucleic acid sequence. Such seeds may be used to isolate insulin or they may be planted to generate two or more subsequent generations. It will generally be desirable to plant a plurality of transgenic seeds to obtain a population of transgenic plants, each comprising seeds comprising a chimeric nucleic acid sequence encoding insulin. Furthermore, it will generally be desirable to ensure homozygosity in the plants to ensure continued inheritance of the recombinant polypeptide. Methods for selecting homozygous plants are well known to those skilled in the art. Methods for obtaining homozygous plants that may be used include the preparation and transformation of haploid cells or tissues followed by the regeneration of haploid plantlets and subsequent conversion to diploid plants for example by the treatment with colchine or other microtubule disrupting agents. Plants may be grown in accordance with otherwise conventional agricultural practices.

In another aspect, the present invention also provides plants capable of setting seed expressing insulin. In a preferred embodiment of the invention, the plants capable of setting seed comprise a chimeric nucleic acid sequence comprising in the 5' to 3' direction of transcription:

(a) a first nucleic acid sequence capable of controlling expression in a plant seed cell operatively linked to;
(b) a second nucleic acid sequence encoding an insulin polypeptide, wherein the seed contains insulin.

In a preferred embodiment the chimeric nucleic acid sequence is stably integrated in the plant's nuclear genome.

In yet another aspect, the present invention provides plant seeds expressing insulin. In a preferred embodiment of the present invention, the plant seeds comprise a chimeric nucleic acid sequence comprising in the 5' to 3' direction of transcription:

(a) a first nucleic acid sequence capable of controlling expression in a plant seed cell operatively linked to;
(b) a second nucleic acid sequence encoding an insulin polypeptide.

In accordance with the present invention, seed is obtained which in which preferably at least 0.1% of the total soluble protein present in the seed is insulin. In further preferred embodiments of the present invention, seed is obtained in which at least 0.2%, 0.3%, 0.5%, or 1.0% of the total soluble protein present in the seed is insulin. The insulin polypeptide may be present in a variety of different types of seed cells including, for example, the hypocotyls and the embryonic axis, including in the embryonic roots and embryonic leafs, and where monocotyledonous plant species, including cereals and corn, are used in the endosperm tissue.

Preparation of Insulin from Plant Seeds

Once the plant seeds have been obtained the insulin protein may be purified from the seed using any protein purification methodologies known to the art. Accordingly, pursuant to the present invention a method of purifying insulin from plant seeds is provided in which the method comprises:

(a) providing a chimeric nucleic acid construct comprising in the 5' to 3' direction of transcription as operably linked components:
   (i) a nucleic acid sequence capable of controlling expression in plant seed cells; and
   (ii) a nucleic acid sequence encoding an insulin polypeptide;
(b) introducing the chimeric nucleic acid construct into a plant cell;
(c) growing the plant cell into a mature plant capable of setting seed wherein the seed expresses insulin;
(d) obtaining seed expressing insulin; and
(e) purifying said insulin from the seed.

The plant seeds may be ground using any comminuting process resulting in a substantial disruption of the seed cell membrane and cell walls. Both dry and wet milling conditions (U.S. Pat. No. 3,971,856; Lawhon et al., 1977, J. Am. Oil Chem. Soc., 63:533-534) may be used. Suitable milling equipment in this regard include colloid mills, disc mills, IKA mills, industrial scale homogenizers and the like. The selection of the milling equipment will depend on the seed type and throughput requirements. Solid seed contaminant such as seed hulls, fibrous materials, undissolved carbohydrates, proteins and other water insoluble contaminants may be removed from the seed fraction using for example size-exclusion based methodologies, such as filtering or gravitational based processes such as centrifugation. In preferred embodiments, the use of organic solvents commonly used in oil extraction, such as hexane, is avoided because such solvents may damage the insulin polypeptide. Substantially pure insulin may be recovered from the seed using a variety of additional purification methodologies such as centrifugation based techniques; size exclusion based methodologies, including for example membrane ultrafiltration and crossflow ultrafiltration; and chromatographic techniques, including for example ion-exchange chromatography, size exclusion chromatography, affinity chromatography, high performance liquid chromatography (HPLC), fast protein liquid chromatography (FPLC), hydrophobic interaction chromatography and the like. Generally, a combination of such techniques will be used to obtain substantially pure insulin.

In a particularly preferred embodiment of the present invention the insulin polypeptide is isolated from the seed contaminants by contacting the insulin polypeptide with oil bodies. This method is considered to be particularly advantageous as it permits the removal seed contaminants including seed proteins in a particularly efficacious and inexpensive manner. As hereinbefore mentioned such contacting of the insulin polypeptide with the oil bodies may be achieved by linking the insulin polypeptide to an oil body protein or by linking the insulin polypeptide to a polypeptide with affinity for an oil body, such as a single chain antibody with affinity for an oil body. In the former embodiment, insulin polypeptide will be sequestered within the cell on the oil bodies and hence co-purify with the oil bodies. In the latter embodiment, upon being expressed in a membrane enclosed intracellular compartment such as the ER, the insulin polypeptide will associate with the oil body upon breakage of the seed cells during the comminuting process. A process for isolating oil bodies is described in U.S. Pat. No. 5,650,554.

Pharmaceutical insulin formulations may be prepared from the purified insulin and such formulations may be used to treat diabetes. Generally the purified insulin will be admixed with a pharmaceutically acceptable carrier or diluent in amounts sufficient to exert a therapeutically useful effect in the absence of undesirable side effects on the patient treated. To formulate an insulin composition, the weight fraction of insulin is dissolved, suspended, dispersed or otherwise mixed in a selected carrier or diluent at an effective concentration such that the treated condition is ameliorated. The pharmaceutical insulin formulations are preferably formulated for single dosage administration. Therapeutically effective doses for the parenteral delivery of human insulin are well known to the art. Where insulin analogs are used or other modes of delivery are used therapeutically effective doses may be readily empirically determined by those of skill in the art using known testing protocols or by extrapolation of in-vivo or in-vitro test data. It is understood however that concentrations and dosages may vary in accordance with the severity of the condition alleviated. It is further understood that for any particular subject, specific dosage regimens may be adjusted over time according to individual judgement of the person administering or supervising administration of the formulations.

Pharmaceutical solutions or suspensions may include for example a sterile diluent such as, for example, water, lactose, sucrose, dicalcium phosphate, or carboxymethyl cellulose. Carriers that may be used include water, saline solution, aqueous dextrose, glycerol, glycols, ethanol and the like, to thereby form a solution or suspension. If desired the pharmaceutical compositions may also contain non-toxic auxiliary substances such a wetting agents; emulsifying agents; solubilizing agents; antimicrobial agents, such as benzyl alcohol and methyl parabens; antioxidants, such as ascorbic acid and sodium bisulfite; chelating agents such as ethylenediaminetetraacetic acid (EDTA); pH buffering agents such as actetate, citrate or phosphate buffers; and combinations thereof.

The final formulation of the insulin preparation will generally depend on the mode of insulin delivery. The insulin prepared in accordance with the present invention may be delivered in any desired manner; however parenteral, oral, pulmonary, buccal and nasal forms of delivery are considered the most likely used modes of delivery. Parenteral preparations can be enclosed in ampoules, disposable syringes or single or multiple dose vials made of glass, plastic or other such suitable materials.

EXAMPLES

The following examples are offered by way of illustration and not by limitation.

Example 1

Preparation of an Insulin Protein Expressed as a Mini-insulin (MI) Fusion Protein with a Trypsin Cleavable Pro-peptide Construction of pSBS4404: PRS-D9scFv-Klip27-MI-KDEL Fusion Protein One of the fusion proteins studied began with the tobacco pathogen related sequence (PRS) (Sijmons et al., 1990, Bio/technology, 8:217-221) which served as the signal peptide to target expression to the ER in a co-translational manner. Immediately downstream was a sequence encoding for a single-chain Fv antibody (scFv) with species-specific affinity against the 18 kDa oleosin from *Arabidopsis thaliana* denoted D9scFv, followed by a trypsin cleavable pro-peptide (KLIP27) derived from the TA57 pro-peptide of yeast (Kjeldsen et al., 2001, Biotechnology and Genetic Engineering Reviews 18:89-121). This was followed by mini-insulin (MI) described by Kjeldsen et al. (2001) with the addition of a KDEL ER-retention signal at the C-terminal end of the polypeptide.

The backbone of this plasmid, pSBS4055, was based on the plant binary vector, pPZP200, described by Hajdukiewicz et al. (Plant Molecular Biology, 1994, 25:989-994). In place of the described multiple cloning site, a pat gene conferring host plant phosphinothricine resistance (Wohlleben et al., 1988, Gene 70:25-37)) driven by the ubiquitin promoter/terminator from *Petroselinum crispum* (Kawalleck et al., 1993, Plant. Mol. Bio., 21:673-684), was inserted between the left and right border sequences. In addition to this cassette, the β-phaseolin promoter/terminator from *Phaseolus vulgaris* (Slightom et al., 1983, Proc. Natl. Acad. Sc. USA 80:1897-1901) driving PRS was sub-cloned. Standard PCR (Horton et al., 1989, Gene 77:61-68) was used to fuse the synthetic PRS-encoding sequence with attached SphI/HindIII restriction endonuclease sites to the 3' end of the phaseolin promoter to yield pSBS4011. A SphI-D9scFv-XhoI, SwaI, HindIII insert sequence was generated by PCR amplification of a D9scFv cDNA clone (Sean Hemmingsen lab, unpublished) with primers 1325 (GCATGCTGACATTG TGATGACACAGTC)—SEQ ID NO :175 and 1326 (AAGCTTGCATTTAAATACTCGAGACTGT-GAGAGTGGTGCCTTG)—SEQ ID NO:176. Subsequent ligation of this fragment at the SphI/HindIII sites of pSBS4011 resulted in plasmid pSBS4055.

The Klip27-MI sequence was synthesized from four partially overlapping oligonucleotides which incorporated *Arabidopsis thaliana* codon usage to increase the success of efficient translation in a plant-based expression system. Oligonucleotides 1324 (GAAGAAGGAGAGCCfAAGTTTGT-TAATCAACATCTTTGTGGATCTCATCT-TGTTGAGGCTCTCTACCTTG)—SEQ ID NO:177 and 1323 (CCTTAGGAGTGTAGAAAAATC-CTCTTTCTCCACACACAAGGTAGAGAGC-CTCAACA)—SEQ ID NO:178 were annealed at their complimentary 20 nucleotide overlap and extended to form the 5' end of the Klip27-MI fusion while the same was done with oligonucleotides 1322 (CTAAGGCTGCTAAGG-GAATTG)—SEQ ID NO:179 and 1321 (AAGCTTCAGT-TGCAATAGTTCTCCAATTGGTAAAGTGAGCAAA TA GAAGTGCAACATTGTTCAACAATTCCCTTAGCAGC CTT)—SEQ ID NO:180 to form the 3' end. The two halves were ligated following restriction digestion with Bsu36I, to yield the full Klip27-MI coding sequence. PCR of this gene fusion using primers 1364 (CTCGAGTCAACCAATTGAT-GACACTGAATC)—SEQ ID NO:181 and 1334 (AAGCT-TCAAAGTTCATCCTTGTTGCAATAGT-TCTCCAATTG)—SEQ ID NO:182 attached a 5' XhoI restriction endonuclease cleavage site and the 3' KDEL DNA sequence plus HindIII cleavage site for subsequent ligation into XhoI/HindIII-cut pSBS4055. The result was plasmid pSBS4404: a DNA sequence encoding the PRS-D9scFv-Klip27-MI-KDEL fusion protein being placed in a binary vector under expression control of the phaseolin promoter/terminator. The phaseolin promoter controls the specific-temporal and tissue-specific expression of the transgene during seed development. The complete nucleic acid sequence (SEQ ID NO:1) and amino acid sequence (SEQ ID NO:2) of the 4404 insulin fusion protein (PRS-D9ScFv-Klip27-MI-KDEL) is shown in FIG. 1.

Construction of pSBS4405:OLEO-Klip8-Klip27-MI Fusion Protein

The second fusion protein studied began with the 18 kDa oleosin from *Arabidopsis thaliana* followed in-frame by a chymosin cleavable pro-peptide (Klip8)—SEQ ID NO:175. Immediately downstream was a sequence encoding for the trypsin cleavable pro-peptide (Klip27) derived from the TA57 pro-peptide of yeast as described above (Kjeldsen et al., 2001, Biotechnology and Genetic Engineering Reviews 18:89-121). This was fused to mini-insulin (MI) described above (Kjeldsen et al., 2001). The expression of this fusion protein was targeted to the nascent oil bodies formed during the development of the embryo.

The backbone of this plasmid, pSBS4055, was based on the plant binary vector, pPZP200, described by Hajdukiewicz et al. (Plant Molecular Biology, 1994, 25:989-994). In place of the described multiple cloning site, a pat gene conferring host plant phosphinothricine resistance (Wohlleben et al., 1988, Gene 70:25-37)) driven by the ubiquitin promoter/terminator from *Petroselinum crispum* (Kawalleck et al., 1993, Plant. Mol. Bio., 21:673-684), was inserted between the left and right border sequences. In addition to this cassette, the β-phaseolin promoter/terminator from *Phaseolus vulgaris* (Slightom et al., 1983, Proc. Natl. Acad. Sc. USA 80:1897-1901) driving the *Arabidopsis* 18 kDa oleosin genomic sequence-Klip8 fusion was sub-cloned. Standard PCR (Horton et al., 1989, Gene 77:61-68) was used to fuse the oleosin gene-Klip8 sequence with attached XhoI/HindIII restriction endonuclease sites to the 3' end of the phaseolin promoter to yield pSBS4010.

Figure 2:
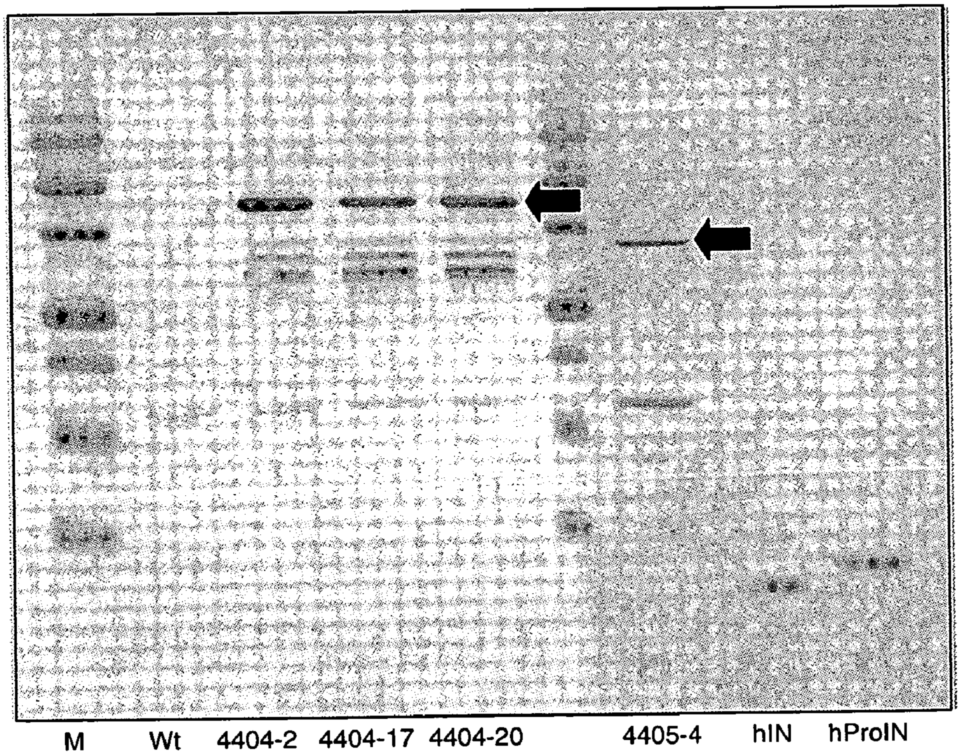
FIG. 2 depicts the nucleotide sequence (SEQ ID NO. 3) and deduced amino acid sequence (SEQ ID NO. 4) of the insulin fusion protein (OLEO-KLIP8-KLIP27-MI) of pSBS4405. The predicted amino acid sequences are shown in single letter code. The deduced amino acid sequence of the *Arabidopsis thaliana* 18 kDa oleosin is in italics, the deduced amino acid sequence of the KLIP 8 sequence is in bold, the deduced amino acid sequence of the KLIP27 sequence is underlined and the deduced amino acid sequence of the mini-insulin is in italics and bold.
Figure 4:
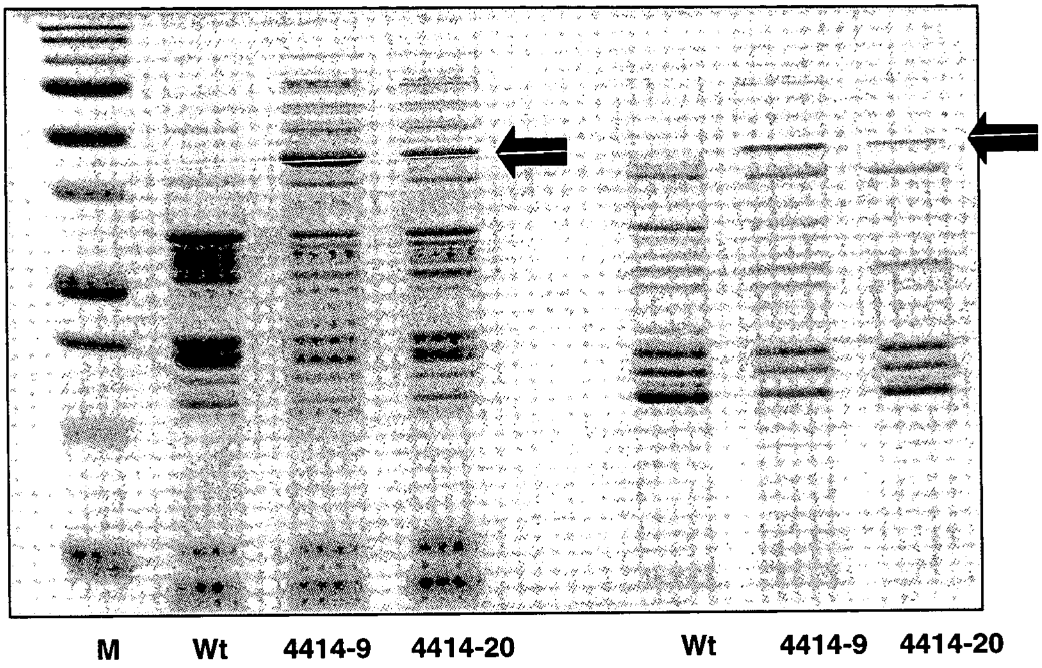

The Klip27-MI sequence was synthesized from four partially overlapping oligonucleotides which incorporated *Arabidopsis thaliana* codon usage to increase the success of efficient translation in a plant-based expression system. Oligonucleotides 1324 (GAAGAAGGAGAGC-CTAAGTTTGTTAATCAACATCTTTGTG-GATCTCATCTTGTTGAGGCTCTCTACCTTG)—SEQ ID NO:177 and 1323 (CCTTAGGAGTGTAGAAAAATC-CTCTTTCTCCACACACAAGGTAGAGAGC-CTCAACA)—SEQ ID NO:178 were annealed at their complimentary 20 nucleotide overlap and extended to form the 5' end of the Klip27-MI fusion while the same was done with oligonucleotides 1322 (CTAAGGCTGCTAAGG-GAATTG)—SEQ ID NO:179 and 1321 (AAGCTTCAGT-TGCAATAGTTCTCCAATTGGTAAAGTGAGCAAATA GAAGTGCAACATTGTTCAACAATTCCCTTAGCAGC CTT)—SEQ ID NO:180 to form the 3' end. The two halves were ligated following restriction digestion with Bsu36I, to yield the full Klip27-MI coding sequence. PCR of this gene fusion using primers 1364 (CTCGAGTCAACCAATTGAT-GACACTGAATC)—SEQ ID NO:181 and 1329 (AAGCT-TCAGTTGCAATAGTTC)—SEQ ID NO:183 attached a 5' XhoI restriction endonuclease cleavage site and a 3' HindIII cleavage site, respectively, for subsequent ligation into XhoI/HindIII-cut pSBS4010. The result was plasmid pSBS4405: a DNA sequence encoding the Oleosin-Klip8-Klip27-MI fusion protein being placed in a binary vector under expression control of the phaseolin promoter/terminator. The phaseolin promoter controls the specific-temporal and tissue-specific expression of the transgene during seed development. The complete nucleic acid sequence SEQ ID NO:3 and amino acid sequence SEQ ID NO:4 of the 4405 insulin fusion protein (OLEO-Klip8-Klip27-MI) is shown in FIG. 2.

Construction of pSBS4414: PRS-MI-tetrabasic Linker-D9Scfv-KDEL Fusion Protein

Another fusion protein studied began with the tobacco pathogen related sequence (PRS) (Sijmons et al., 1990, Bio/technology, 8:217-221) which served as the signal peptide to target expression to the ER in a co-translational manner. Immediately downstream was the sequence encoding mini-insulin (MI) described by Kjeldsen et al. (2001) with the exception that the mini-C propeptide region (AAK—SEQ ID NO:146) was replaced with an intervening $B_{30}$ Threonine-tetrabasic site ($B_{30}$T-RRKR) (SEQ ID NO:149) sequence between the $B_{(1-29)}$- and $A_{(1-21)}$-chains of human insulin. This was immediately followed by a sequence encoding for a second tetrabasic linker followed by a single-chain Fv antibody (scFv) with species-specific affinity against the 18 kDa oleosin from *Arabidopsis thaliana* denoted D9scFv. At the C-terminal end of the polypeptide was the addition of a KDEL ER-retention signal.

The plasmid backbone, pSBS4055, was based on the plant binary vector, pPZP200, described by Hajdukiewicz et al. (Plant Molecular Biology, 1994, 25:989-994). In place of the described multiple cloning site, a pat gene conferring host plant phosphinothricine resistance (Wohlleben et al., 1988, Gene 70:25-37)) driven by the ubiquitin promoter/terminator from *Petroselinum crispum* (Kawalleck et al., 1993, Plant. Mol. Bio., 21:673-684), was inserted between the left and right border sequences. In addition to this cassette, the β-phaseolin promoter/terminator from *Phaseolus vulgaris* (Slightom et al., 1983, Proc. Natl. Acad. Sc. USA 80:1897-1901) driving PRS was sub-cloned. Standard PCR (Horton et al., 1989, Gene 77:61-68) was used to fuse the synthetic PRS-encoding sequence with attached SphI/HindIII restriction endonuclease sites to the 3' end of the phaseolin promoter to yield pSBS4011.

The Klip27-MI sequence was synthesized from four partially overlapping oligonucleotides which incorporated *Arabidopsis thaliana* codon usage to increase the success of efficient translation in a plant-based expression system. Oligonucleotides 1324 (GAAGAAGGAGAGC-CTAAGTTTGTTAATCAACATCTTTGTG-GATCTCATCTTGTTGAGGCTCTCTACCTTG) SEQ ID NO:177 and 1323 (CCTTAGGAGTGTAGAAAAATC-CTCTTTCTCCACACACAAGGTAGAGAGCCTCAACA) SEQ ID NO:178 were annealed at their complimentary 20 nucleotide overlap and extended to form the 5' end of the Klip27-MI fusion while the same was done with oligonucleotides 1322 (CTAAGGCTGCTAAGGGAATTG) SEQ ID NO:179 and 1321 (AAGCTTCAGTTGCAATAGTTCTC-CAATTGGTAAAGTGAGCAAATAGAAGTG-CAACATTGTTCAACAATTCCCTTAGCAGCCTT) SEQ ID NO:180 to form the 3' end. The two halves were ligated following restriction digestion with Bsu36I, to yield the full Klip27-MI coding sequence. PCR of this gene fusion using primers 1363 (GCATGCCCAACCAATTGATGACACTG) SEQ ID NO:184 and 1334 (AAGCTTCAAAGTTCATCCT-TGTTGCAATAGTTCTCCAATTG) SEQ ID NO:182 attached a 5' SphI restriction endonuclease cleavage site and the 3' KDEL DNA sequence plus HindIII cleavage site for subsequent ligation into SphI/HindIII-cut pSBS4011. The result was plasmid pSBS4402: a DNA sequence encoding the PRS-Klip27-MI-KDEL fusion protein being placed in a binary vector under expression control of the phaseolin promoter/terminator. The phaseolin promoter controls the specific-temporal and tissue-specific expression of the transgene during seed development. The plant expression vector, pSBS4402, served as the template to introduce tetrabasic sites between the B and A chains of insulin and between MI and D9 Scfv.

Figure 3:
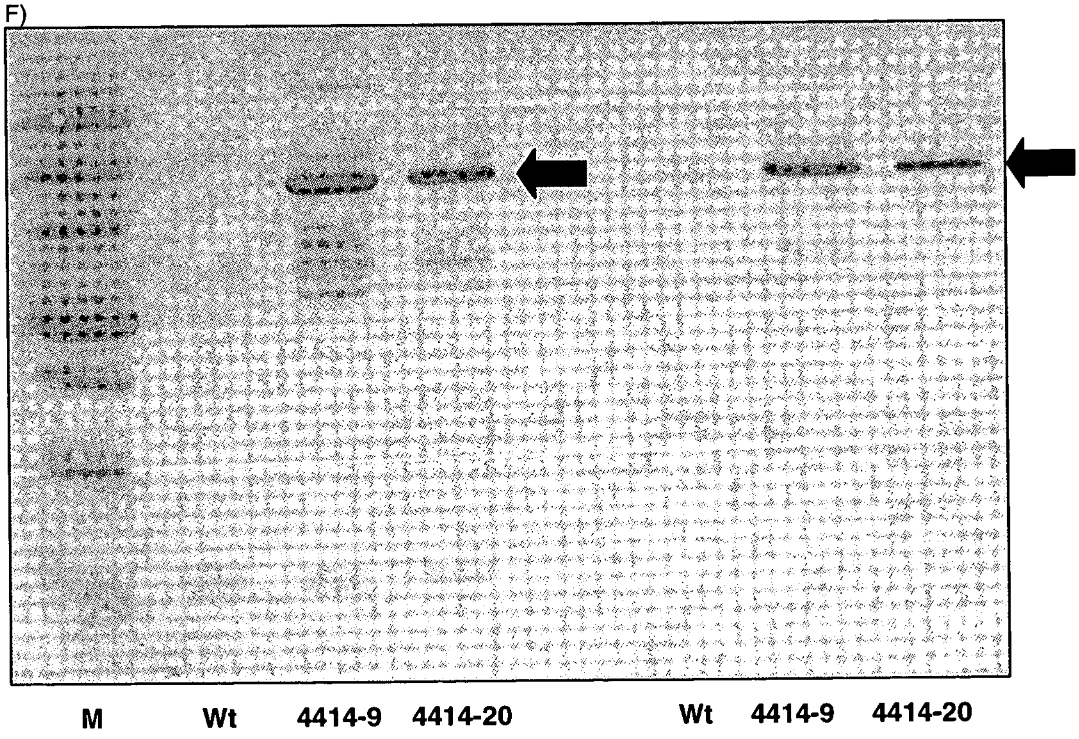
FIG. 3 depicts the complete nucleic acid sequence (SEQ ID NO:5) and amino acid sequence (SEQ ID NO:6) of the 4414 insulin fusion protein (PRS-MI-tetrabasic linker-D9Scfv-KDEL). The predicted amino acid sequences are shown in single letter code. The deduced amino acid sequence of the PRS signal peptide is in italics, the deduced amino acid sequence of the mini-insulin (B30 tetrabasic) is in bold, the deduced amino acid sequence of the tetra-basic linker sequence is underlined, the deduced amino acid sequence of the D9 scFv is in italics and bold and finally the KDEL sequence is bolded and underlined.

An intravening tetrabasic ($B_{30}$T-RRKR) site was placed between the authentic $B_{(1-29)}$- and $A_{(1-21)}$-chains of human insulin by PCR using primers 1515 (GCATGCATGC-CTTTGTTAATCAACATCTTTGTGG) SEQ ID NO:185 and 1518 (ACATTGTTCAACAATTCCTCTCTTTCT-TCTAGTCTTAGGAGTGTAGAAAAATCC) SEQ ID NO:186 using pSBS4402 as the template. The resulting 124 bp fragment was used in combination with primer 1517 (GCATAAGCTTCAAAGCTCATCCTTTGAGC) SEQ ID NO:187 using pSBS3400 as a template. Note that pSBS3400 is a plasmid that contains the D9 scFv-KDEL fragment with a HindIII restriction site. This PCR reaction produced a 955 bp product which introduced a tetrabasic (RRKR)-D9 Scfv-KDEL-HindIII onto the 124 bp SphI-MI fragment. The 955 bp fragment was then ligated and subcloned in pGEM-T (Promega) to result in pSBS3403. The entire SphI-MI (with $B_{30}$T-RRKR modified C propeptide)-RRKR-D9 Scfv-KDEL-HindIII fragment was inserted into precut (SphI/HindIII) pSBS4402 to generate pSBS4414. The complete nucleic acid sequence SEQ ID NO:5 and amino acid sequence SEQ ID NO:6 of the 4414 insulin fusion protein (PRS-MI-tetrabasic linker-D9Scfv-KDEL) is shown in FIG. 3.

Transformation and Growth of Recombinant *E. coli* and *Agrobacterium* with pSBS4404, pSBS4405 or pSBS4414.

After confirming the integrity of the cDNA encoding for the fusion protein by sequence analysis, the plasmids pSBS4404, pSBS4405 and pSBS4414 were transformed into *E. coli* strain DH5α to allow for high level of expression. Isolated plasmid DNA (100 ng) was mixed on ice with 100 μd of DH5α competent cells for 20 min. The cells were then heat shocked at 42° C. for 45 seconds and returned to ice for 2 min. Then 1 ml of SOC media was added and the cells were incubated at 37° C. on an enviro-shaker at 225 rpm for 1 hr before plating transformed cells on LB-spectinomycin plates (10 g/L tryptone, 5 g/L yeast extract, 5 g/L NaCl, 15 g/L agar) and incubating overnight at 37° C. A single colony was used to inoculate 5 ml LB-spectinomycin broth. These cultures were grown overnight at 37° C. The recombinant plasmid was isolated from 1 ml of the overnight culture according to QIAPREP®Spin Miniprep Kit (Qiagen). The isolated plasmid was then used to transform competent *Agrobacterium* strain EH101 (Hood et al., 1986; J. Bacteriol. 144: 732-743) by electroporation (25 μF, 2.5 kV, 200Ω). Recombinant *Agrobacterium* were plated on AB-spectinomycin/kanamycin (20×AB salts, 2 M glucose, 0.25 mg/ml $FeSo_4 7H_2O$, 1 M $MgSo_4$, 1 M $CaCl_2$) and a single colony was used to inoculate 5 ml of AB-spectinomycin/kanamycin broth. These cultures were grown overnight at 28° C. The recombinant *Agrobacterium* were then used to transform *Arabidopsis thaliana* plants by the flower dipping method (Clough et al., 1998, Plant J., 16:735-743). *Arabidopsis* thaliana cv. (C24) is used for all the experiments. Seeds are planted on the surface of a soil mixture (two-thirds REDI–EARTH® professional growing mix and one-third perlite with a pH=6.7) or an *Arabidopsis* soil mixture supplied by Lehle Seeds (perlite, vermiculite, peat, terra-green, with a pH=5.5) in 4 inch pots. The seedlings are allowed to grow to a rosette stage of 6-8 leaves to a diameter of approximately 2.5 cm. The pots are placed inside a dome at 4° C. for four days for a cold treatment and subsequently moved to 24° C. growth room with constant light at about 150 μE and 60-70% relative humidity. The plants are irrigated at 2-3 day interval and fertilized weekly with 1% of Peters 20-19-18. Each pot contains five to six plants. When plants reach about 2 cm in height, the primary bolts are cut to encourage the growth of secondary and tertiary bolts. 4 to 5 days after cutting the primary bolts, the plants are ready to be infected with *Agrobacterium*. The pots with *Arabidopsis* plants are inverted to allow the *Arabidopsis* plants being infected with 500 ml of a re-suspension an overnight *Agrobacterium* culture containing the plant transformation vector of interest for 20 seconds. It is important that the *Agrobacterium* culture contains 5% sucrose and 0.05% of the surfactant SILWET L-77® surfactant (Lehle Seeds). The pots are subsequently covered with a transparent plastic dome for 24 hours to maintain higher humidity. The plants are allowed to grow to maturity and a mixture of seeds, untransformed and transformed, are harvested. For selection of transgenic lines, the putative transformed seeds are sterilized in a quick wash of 70% ethanol, then a 20% commercial bleach for 15 min and then rinsed at least four times with $ddH_2O$. About 1000 sterilized seeds are mixed with 0.6% melted top agar and evenly spread on a half strength MS plate (Murashige and Skoog, 1962, Physiologia Plantarum 15: 473-497) containing 0.3% sucrose and 80 μM of the herbicide phosphinothricin (PPT) DL. The plates are then placed in a growth room with light regime 8 hr dark and 16 hr light at 24° C. After 7 to 10 days, putative transgenic seedlings are green and growing whereas untransformed seedlings are bleached. After the establishment of roots the putative transgenic seedlings are individually transferred to pots (the individually plants are irrigated in 3 day interval and fertilized with 1% Peters 20-19-18 in 7 day interval) and allowed to grow to maturity. The pots are covered with a transparent plastic dome for three days to protect the sensitive seedlings. After 7 days the seedlings are covered with a seed collector system from Lehie Seeds to prevent seed loss due to scattering. Seeds from these transgenic plants are harvested individually and ready for analysis.

Example 2

Expression Levels of Insulin in *Arabidopsis thaliana*

In the second example, expression levels of the fusion protein D9scfv-KLIP27-MI-KDEL (4404), OLEO-KLIP8-KLIP27-MI (4405) and PRS-MI-RRKR-D9Scfv-KDEL (4414) were determined in transgenic *Arabidopsis thaliana* mature seed. The transgene product was shown to be present in the cellular extracts of mature seed. Approximately 40 transgenic *Arabidopsis thaliana* seeds were ground with a mortar and pestle in 50 μl of 50 mM Tris-HCl pH 8.0. Then, a reducing SDS-PAGE sample buffer (6×SDS sample buffer, 0.35 M Tris-HCl pH 6.8, 30% glycerol, 10% SDS, 0.012% bromophenol blue, 5% β-mercaptoethanol) was added to the slurry and mixed by briefly vortexing. The sample was then briefly centrifuged and placed at 99° C. for 10 minutes. After cooling on ice for 2 minutes the sample was centrifuged briefly. Samples were loaded (10 μl—equivalent to approximately 7 seeds) under reducing conditions.

For oil body prepared samples the transgenic and wild type seed (20 mg) were ground in 250 μl oil body extraction buffer (0.4 M sucrose, 0.5 M NaCl, 50 mM Tris-HCl pH 8.0). Samples were microfuged at 10 000 g for 10 min. The soluble aqueous fraction was removed with a 26 G ⅝ 1 ml syringe and the fat pad was re-suspended in 100 μl phosphate buffer supplemented with salt (20 mM $Na_2HPO_4$ pH 8.0, 0.5 M NaCl). The re-suspended fat pad was transferred to a clean microfuge tube and centrifuged again at 10 000 g for 10 min. The procedure was repeated 3 more times with a final re-suspension of the fat pad in 100 μl phosphate buffer without salt (20 mM $Na_2HPO_4$ pH 8.0). An additional two more washes in phosphate buffer without salt were performed with intermittent centrifugation steps as outlined above. The final fat pellet was re-suspended in 10 μl phosphate buffer (20 mM $NA_2HPO_4$ pH 8.0). A 5 μl aliquot was taken and the oil body protein solubilized by boiling in 1/10 (v/v) 50 mM Tris-HCl pH 8.0 with 2% SDS. The sample was cooled on ice for 2 min and centrifuged at 10 000 g for 5 min. The protein content of the undernatant was determined by BCA protein assay (Pierce, Rockford, Ill.). For coomassie-stained gels and Western blot analysis, 20 μg of total protein was separated on 15% SDS-PAGE gels under reducing conditions using the SDS-PAGE sample buffer.

The sample(s) were then loaded on discontinuous 15% SDS-PAGE gels and separated at 150 volts for approximately 1.5 hours. Gels were then either Coomassie-stained or blotted onto PVDF membrane IMMOBILON-P® transfer membrane, Millipore Corporation, Bedford, Mass.) for Western blot analysis. Blotted samples were probed with monoclonal antibody directed against insulin (Clone E2–E3; Roth et al., 1992) purchased from Abcam (Cambridge, UK). Insulin bands were detected using a secondary Sheep X mouse IgG F(ab')2 AP-conjugate (Chemicon International, Temecula, Calif.) and developed using NBT-BCIP in GARAP buffer (Tris-HCl pH 9.5, 100 mM NaCl, 5 mM Mg $Cl_2$). The immunoreactive band corresponded to a polypeptide band, migrating at the predicted molecular weight of the fusion protein, as shown in FIGS. 4A-4F. FIGS. 4(A-F) show recombinant expression of insulin fusion proteins in transformed *Arabidopsis thaliana* lines (4404-2, -17, -20, 4405-4, 4414-19 and 4414-20) on the basis of Coomassie-stained SDS-PAGE and Western Blot analysis. The arrows denote the position of the migrating 38.5 kDa, 34.2 kDa and 34.2 kDa fusion polypeptides, PRS-D9(scfv)-KLIP27-MIw/KDEL (4404), OLEO-KLIP8-KLIP27-MI (4405) and PRS-MI-RRKR-D9Scfv-KDEL (4414) respectively, under reducing conditions. It should be noted 4414 fusion protein has an expected molecular weight of 34.2 kDa but has a higher apparent molecular weight on a SDS-PAGE gel). FIGS. 4A (Coomassie-stained gel) and 4B (corresponding Western blot probed with anti-insulin E2E3) show total seed protein from wild type (wt) and transgenic seed lines expressing the 4404 and 4405 constructs. FIGS. 4C (Coomassie-stained gel) and 4D (corresponding Western blot probed with anti-insulin E2E3) show oil body protein prepared from wild type and transgenic seed expressing the same 4404 and 4405 constructs. FIGS. 4D (Coomassie-stained gel) and 4E (corresponding Western Blot probed with anti-insulin E2E3) show oil body protein prepared from wild type and transgenic seed expressing the same 4414 constructs. The molecular weight markers (M) are 10, 15, 20, 25, 37, 50, 75, 100, 150, 250 kDa. Controls include, hIN (recombinant human insulin standard) and hProIN (recombinant human proinsulin standard), separated under non-reducing conditions. Differences in expression levels are the result of clonal variation amongst transformants. The approximate protein levels of transgene and MI expression are shown in FIG. 5. Levels of expression were determined using the 18 kDa oleosin band as an internal standard (equivalent to 1.5% total seed protein) by densitometry of the transgene band. The average level of expression for the PRS-D9 (scfv)-KLIP27-MIw/KDEL (4404), OLEO-KLIP8-KLIP27-MI (4405) and PRS-MI-RRKR-D9Scfv-KDEL (4414)

constructs were 0.21% total seed protein, 0.12% total seed protein and 0.79% total seed protein respectively.

Example 3

Cleavage of pSBS4404 and HPLC Purification

Elution from Oil Body

Figure 6:
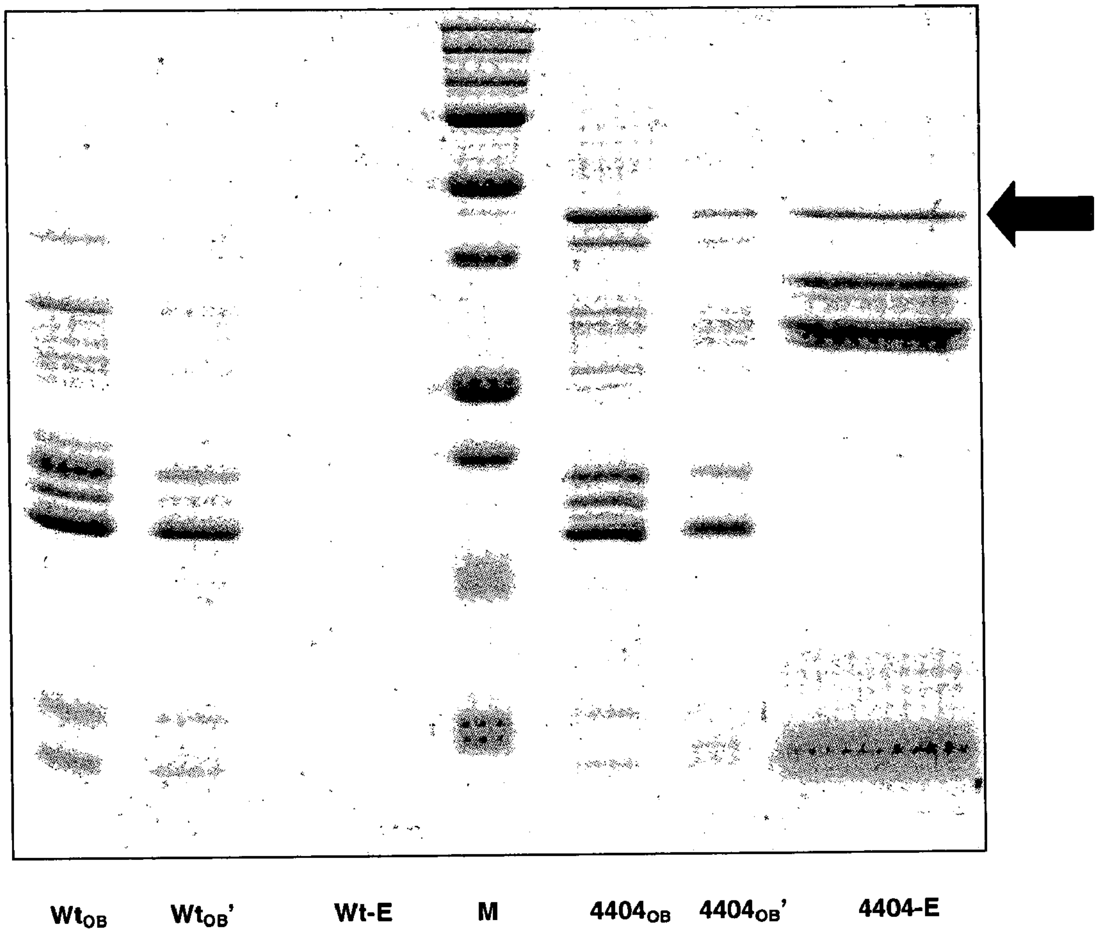
FIG. 6 depicts Coomassie-stained SDS-PAGE (15%) analysis of oil body preps prior to elution (–OB), OB prep after elution with formic acid (–OB'), and the concentrated eluted material (–E). The arrow denotes the position of the migrating fusion polypeptide. The wild type control is essentially free of any major proteins following elution whereas the concentrated 4404 material contains the fusion protein, some truncated products (possible hydrolyzed fusion protein) and possibly some albumins that co-eluted.

In the third example, 1 g of transgenic seed was homogenized in 12 ml extraction buffer (0.4 M sucrose, 0.5 M NaCl, 50 mM Tris-HCl pH 8.0) and centrifuged at 10 000 g for 10 min, the fat pads were removed and placed in 1 ml of 20 mM $Na_2HPO_4$, 0.5 M NaCl and re-centrifuged as above. This was repeated twice, before washing and centrifuging the fat pad twice in 750 μl 20 mM $Na_2HPO_4$. The 4404 fusion protein was eluted from the oil body into the undernatant by washing the final fat pad 5 times in 750 μl 20 mM formic acid pH 4.1, with 10 000 g centrifugation steps in between each wash. The collected elution fractions (undernatants) were pooled and neutralized with 2 N NaOH to pH 8.0. The entire solution was then placed at −80° C. to freeze, and lyophilized overnight to concentrate the fusion protein. The lyophilized sample was re-suspended in 500 μl 50 mM Tris-HCl pH 8.0. The resuspended 4404 fusion protein was then desalted on a NAP-5 column (Amersham Pharmacia Biotech Ab, Uppsala, Sweden) and re-exchanged with buffer (50 mM Tris-HCl pH 8.0). The desalted fraction was then frozen again and lyophilized overnight to concentrate. The final concentrated sample was re-suspended in a final volume of 105 μl double distilled $H_2O$. The elution results are presented in FIG. 6. FIG. 6 is a Coomassie-stained SDS-PAGE (15%) analysis of oil body preps prior to elution (−OB), OB prep after elution with formic acid (−OB'), and the concentrated eluted material (−E). The arrow denotes the position of the migrating fusion polypeptide. The wild type control is essentially free of any major proteins following elution whereas the concentrated 4404 material contains the fusion protein, some truncated products (possible hydrolyzed fusion protein) and possibly some albumins that co-eluted.

Cleavage and HPLC Analysis of 4404 Expressing *Arabidopsis* Seed

Figure 7:
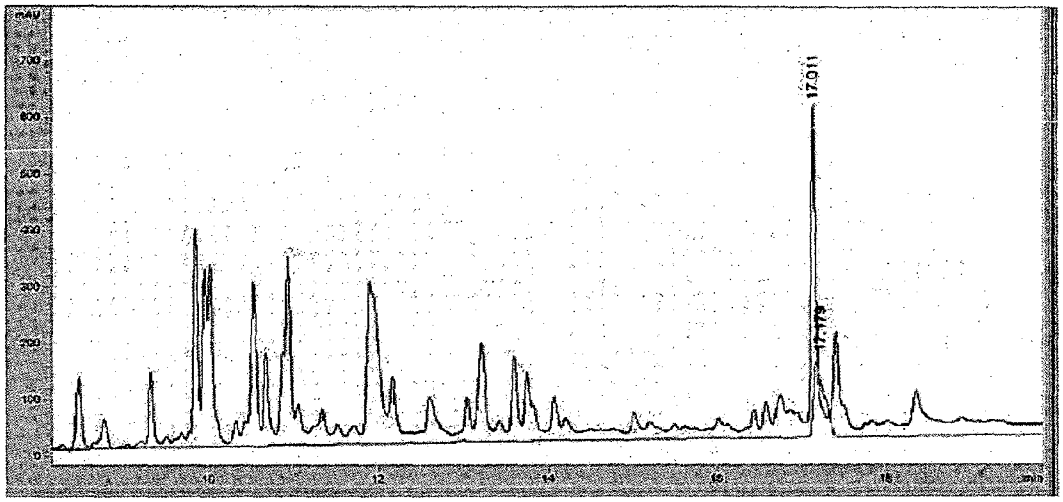
FIG. 7 depicts the chromatograms depicting the characteristic retention times of the human insulin standard (retention time 17.179 min) in comparison to the trypsin cleaved eluted 4404 fusion protein (retention time 17.011 min) on the C18 column. The hIN standard is recombinant human insulin standard (0.5 μg).
Figure 8:
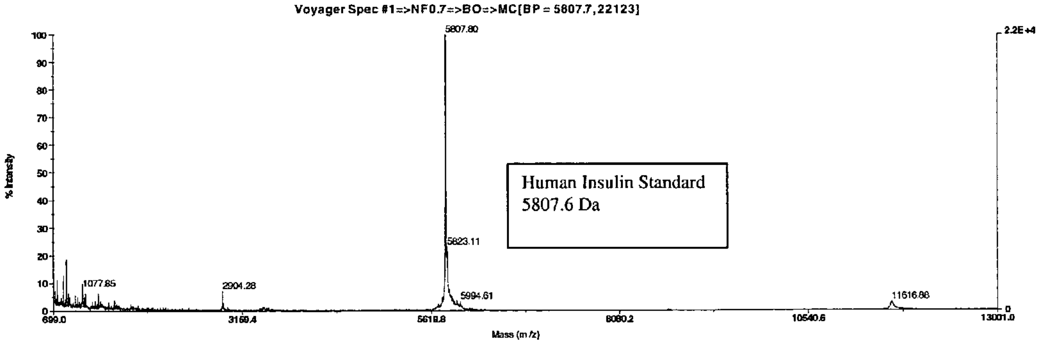
FIG. 8 depicts the mass spectral analysis of human insulin standard (A) in comparison to trypsin cleaved and HPLC purified 4404 (B) fractions collected from 17.0-17.5 minutes.
Figure 8:
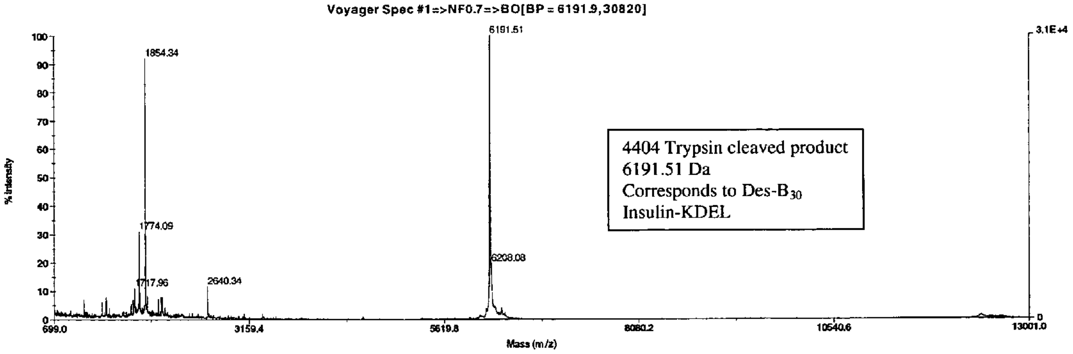

The concentrated sample was resuspended in 105 μl of double distilled water and protein content was assessed by BCA protein assay according to the manufacture (Pierce, Rockford, Ill., USA). Samples were then cleaved with trypsin (1:300 trypsin:total protein ratio, in 50 mM Tris-HCl pH 8.0, on ice for 90 min). The reactions were stopped with a 10 fold molar excess of TLCK (N-p-tosyl-L-lysine chloromethyl ketone). The entire reactions were then filtered through 0.2 μm filters (AERODISC® 13 mm Syringe filter with 0.2 μm SUPOF® membrane, Pall Corporation, Ann Arbor, Mich., USA) and analyzed by reversed phase (RP)-HPLC using a C18 column (ZORBAX® HPLC column 300SB-C18, Agilent Technologies, Waldbronn, Germany). Samples were loaded onto the column and eluted off at 1.0 ml/min using a 19-min linear gradient of 5-50% (v/v) acetonitrile in 0.1% (vlv) TFA. The chromatograph resulting from this analysis is seen in FIG. 7. The trace reveals a trypsin cleaved product from 4404 fusion protein, with nearly identical properties on the column as the human insulin standard (retention times of 17.011 min and 17.179 min, respectively). The HPLC fraction was collected from 17.0-17.5 min and analyzed by PSD MALDI/TOF mass spectrometry using a Voyager-DE STR mass spectrometer (Applied Biosystems). MS analysis was performed by the BioAnalytical Spectroscopy service provided through NRC-Plant Biotechnology Institute, Saskatoon, Saskatchewan, Canada. Resolution of the cleaved 4404 product purified by HPLC as described above is shown in FIG. 8B in comparison to human insulin standard shown in FIG. 8A. The observed mass of cleaved 4404 fusion protein with trypsin was 6191.51 Da. The discrepancy between human insulin standard (FIG. 8A) and the cleaved 4404 product (FIG. 8B) corresponds to a Des-$B_{30}$ Insulin with the KDEL signal retained on the A-chain of the cleaved product (Des-$B_{30}$ Insulin-KDEL).

Example 4

Cleavage of pSBS4405 and HPLC Purification

Oil Body Preparation

Fusion protein (OLEO-KLIP8-KLIP27-MI) can be partially purified by performing oil body preparations as described below. Approximately, 1 g of transgenic seed was homogenized in 12 ml extraction buffer (0.4 M sucrose, 0.5 M NaCl, 50 mM Tris-HCl pH 8.0) and centrifuged at 10 000 g for 10 min, the fat pads were removed and placed in 1 ml of 50 mM Tris-HCl pH 8.0, 0.5 M NaCl and re-centrifuged as above. This was repeated twice, before washing and centrifuging the fat pad twice in 750 μl 50 mM Tris-HCl pH 8.0. The oil body preparation results in the removal of the majority of background proteins. The typical protein profile of an oil body preparation from transgenic *Arabidopsis* seed expressing the 4405 construct is demonstrated in FIG. 9.

Cleavage and HPLC *Analysis* of 4405 Expressing *Arabidopsis* Seed

Figure 9:
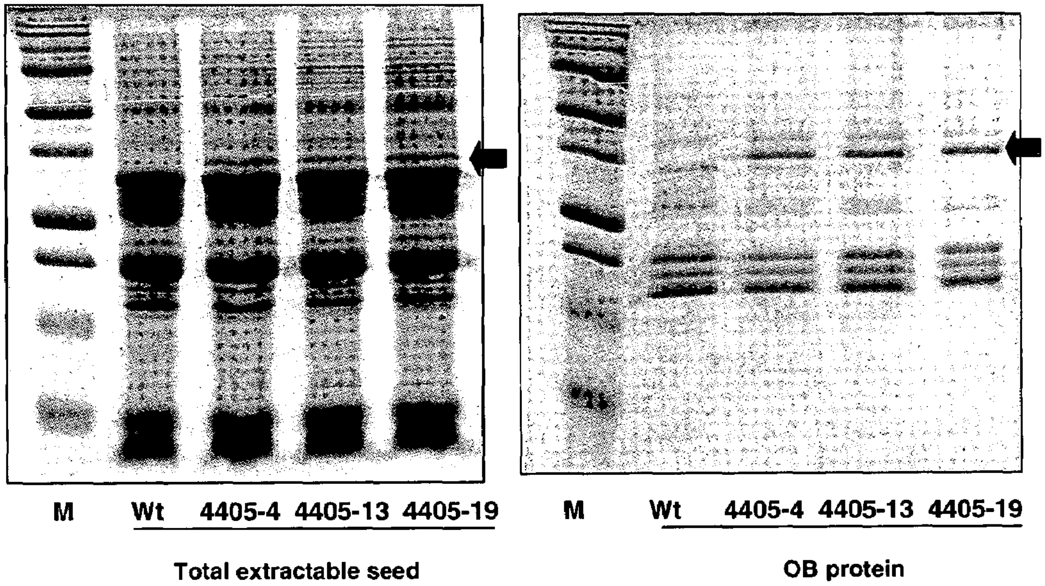
FIG. 9 depicts the Coomassie-stained SDS-PAGE (15%) analysis of total extractable seed protein and oil body (OB) prepared protein from lines expressing 4405 in comparison to wild type (nonrecombinant) seed. The arrow denotes the position of the migrating fusion polypeptide.
Figure 10:
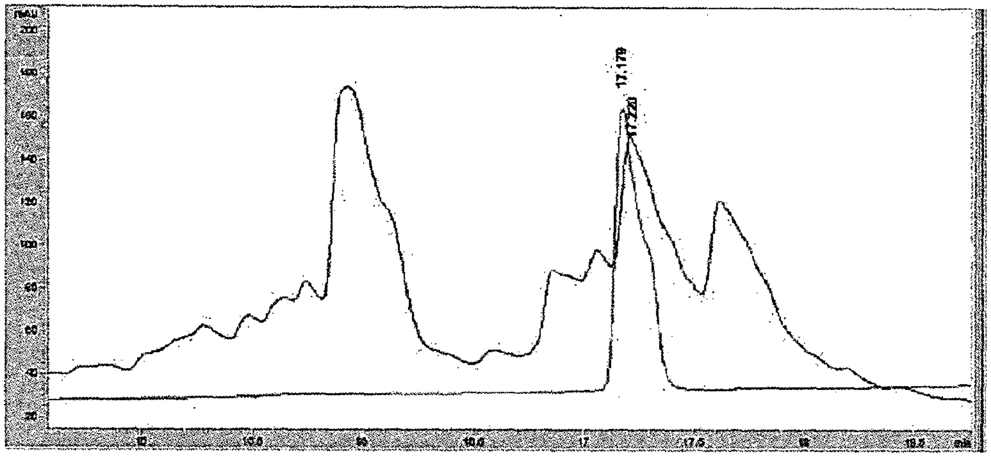
FIG. 10 depicts the chromatograms depicting the characteristic retention times of the human insulin standard (retention time 17.179 min) in comparison to the trypsin cleaved 4405 OB preparations (retention time 17.220 min) by RP-HPLC on the C18 column. The hIN standard is recombinant human insulin standard (0.5 μg).
Figure 11:
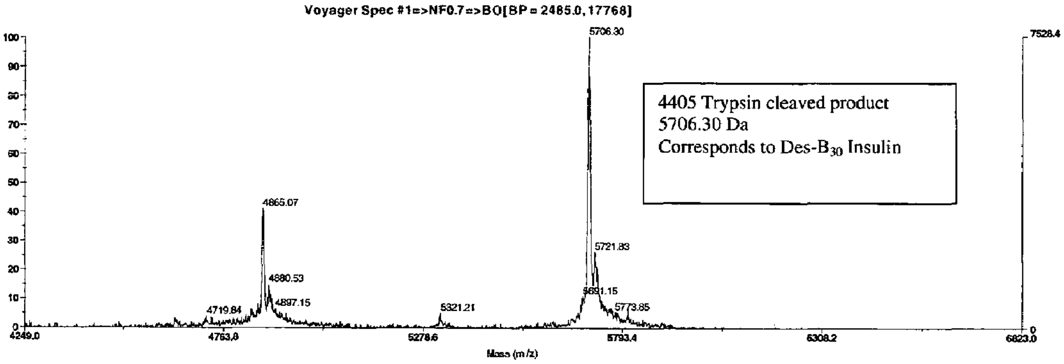
FIG. 11 depicts the mass spectral analysis of human insulin standard (A) in comparison to trypsin cleaved and HPLC purified 4405 (B) fractions collected from 17.0-17.5 minutes.

The total protein content from resuspended oil bodies was assessed by solubilizing a fraction of the preparation (5 μl) diluted 10 times in 2% SDS, 50 mM Tris-HCl pH 8.0, boiled for 5 minutes and centrifuged for 3 min at 10 000 g. Thereafter, the protein content was determined by BCA protein assay according to the manufacture (Pierce, Rockford, Ill., USA). Samples were then cleaved with trypsin (1:300 trypsin:total protein ratio, in 50 mM Tris-HCl pH 8.0, on ice for 90 min) to release the Klip27-MI fragment from the fusion protein. The reactions were stopped with a 10 fold molar excess of TLCK (N-p-tosyl-L-lysine chloromethyl ketone). Samples were centrifuged at 10 000 g for 10 min and the undernatants of the entire reactions were then filtered through 0.2 μm filters (AERODISC® 13 mm Syringe filter with 0.2 μm SUPOF® membrane, Pall Corporation, Ann Arbor, Mich., USA). FIG. 9 depicts the Coomassie-stained SDS-PAGE (15%) analysis of total extractable seed protein and oil body (OB) prepared protein from lines expressing 4405 in comparison to wild type (nonrecombinant) seed. The arrow denotes the position of the migrating fusion polypeptide. The undernatants were further analyzed by reversed phase (RP)-HPLC using a C18 column (ZORBAX® HPLC column 300SB-C18, Agilent Technologies, Waldbronn, Germany). Samples were loaded onto the column and eluted off at 1.0 ml/min using a 19-min linear gradient of 5-50% (v/v) acetonitrile in 0.1% (v/v) TFA. The chromatograph resulting from this analysis is seen in FIG. 10. The trace reveals a trypsin cleaved product from 4405 fusion protein, with nearly identical properties on the column as the human insulin standard (retention times of 17.220 min and 17.179 min, respectively). The HPLC fraction was collected from 17.0-17.5 min and analyzed by PSD MALDI/TOF mass spectrometry using a Voyager-DE STR mass spectrometer (Applied Biosystems). MS analysis was performed by the BioAnalytical Spectroscopy service provided through NRC-Plant Biotechnolgoy Institute, Saskatoon, Saskatchewan, Canada. As shown in FIG. 11, the observed mass of cleaved 4405 fusion protein with trypsin was 5706.30 Da. The discrepancy between human insulin standard (FIG. 8A) and the cleaved 4405 product (FIG. 11) correspond to a Des-$B_{30}$ Insulin product (Des-$B_{30}$ Insulin). The Des-$B_{30}$ Insulin is the product expected from correct trypsin maturation of the 4405 fusion.

Example 5

Purification of Trypsin Cleaved MI using AKTA Explorer (FPLC)

Figure 12:
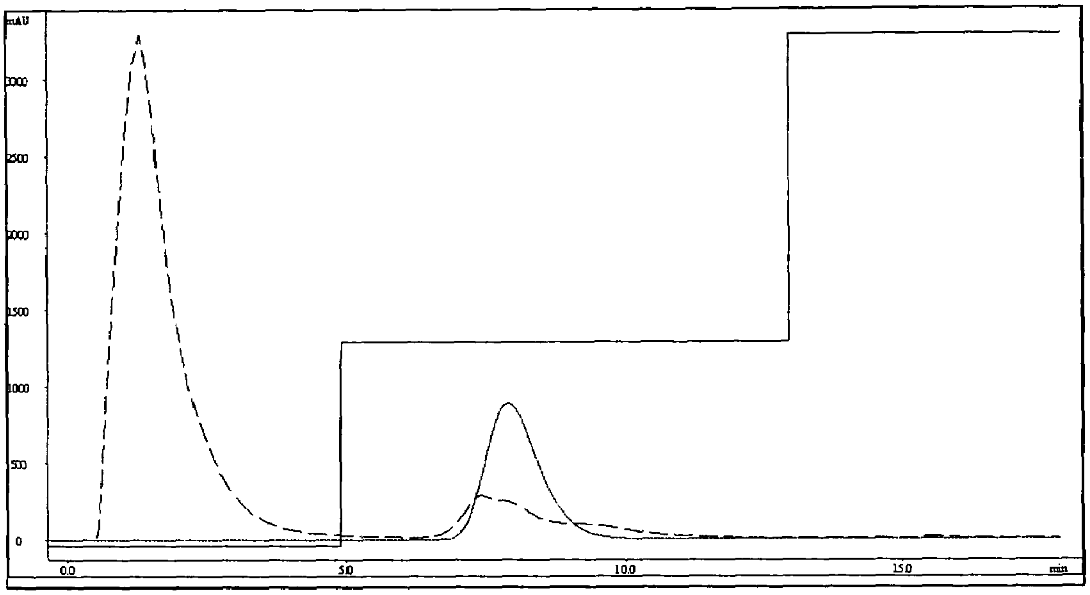
FIG. 12 depicts the chromatogram of trypsin cleaved 4405 oil body preparations (dashed line) in comparison to human insulin standard (solid line). Fractions of the eluted cleaved insulin was collected between 7-35 mS/cm and concentrated by lyophilization for insulin bioassay.

Purification of cleaved MI from 4405 was also partially purified from upscaled cleavage reactions by anion exchange (Mono Q FF 1 mL, Amersham Pharmacia) on an AKTA explorer (Amersham Pharmacia). Cleavage reactions were performed on 4405 oil body as described above prepared from up to 30 g transgenic seed. The undernatant from cleavage reactions were either filtered through 0.2 μm filters or concentrated by lyophilization on a Savant SPEEDVAC® concentrator. Sample reactions filtered could be applied to the column directly, but concentrated samples required the removal of salts to effectively bind the column. Concentrated samples could be desalted by passing cleaved material through a PD-10 column (Amersham Pharmacia), by dialysis, or dilution to a salt concentration equivalent or less than 5 mS/cm. Desalted samples were equilibrated with 20 mM Tris-HCl pH 6.5. Samples were separated using a step gradient with NaCl of 0-40% NaCl with a 1 ml/min flow rate. Detection was performed at 214 nm (detection at 280 nm is relatively poor because of the low content of aromatic amino acids in insulin). Solvent A was 20 mM Tris-HCl pH 6.5 while solvent B was 20 mM Tris-HCl pH 6.5, 1.0 M NaCl. Fractions (1 ml) eluting at the same conductivity as Roche insulin standard, between 7-35 mS/cm, were collected (refer to FIG. 12). FIG. 12 shows the chromatogram of trypsin cleaved 4405 oil body preparations (dashed line) in comparison to human insulin standard (solid line). The presence of Insulin was verified in the collected fractions by HPLC, ELISA, or Western analysis (data not shown). Samples collected were then concentrated by lyophilization and used in the insulin bioassay described in example 6.

Example 6

Insulin Tolerance Test: Bioassay in C57BI/6 (B6) Male Mice

This bioassay was performed to determine the in vivo effect of recombinant plant-derived (Des$B_{30}$ IN) from trypsin cleaved 4405 in comparison to human insulin. Glucose plasma levels in B6 mice were determined prior to and following the intraperitoneal injection of insulin standards, negative controls, and SBS insulin. Fifteen male C57BI/6 (B6) mice approximately 2 months of age were purchased from Jackson Laboratories (Bar Harbor, Me.). Plasma glucose levels were determined with an automatic glucometer (ONETOUCH ULTRA® blood glucose monitor, Lifescan, Johnson and Johnson). Positive controls included HUMULIN® insulin (Eli Lilly) and yeast recombinant human insulin standard from Roche. A saline solution served as the placebo. A negative control was included which represented trypsin cleaved oil bodies purified from wild type (non-recombinant) *Arabdiopsis* seed that was processed identically to recombinant 4405 trypsin cleaved oil body preparations.

Figure 13:
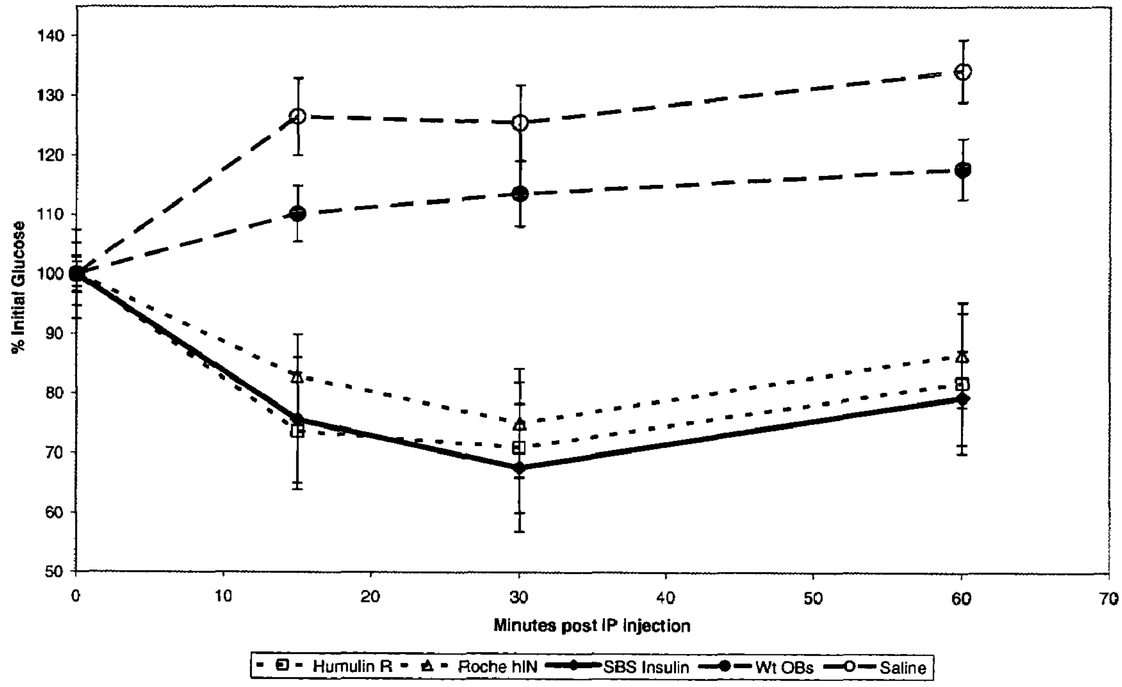
FIG. 13 depicts the changes in serum glucose levels in male B6 mice following injection of negative controls (open circles=saline placebo, closed circles=trypsin cleaved wild type oil bodies), positive controls (open squares=Humulin R, open triangles=Roche hIN) in comparison to plant derived insulin prepared from 4405 oil bodies (closed diamonds=SBS hIN DesB$_{30}$).

B6 mice were housed and fed ad libitum on a 12-hour dark-light cycle. For insulin tolerance tests mice were injected intraperitoneally (IP) with insulin (1 U/kg body weight) and glucose levels determined at 0, 15, 30, and 60 minutes using the automatic glucometer. All insulin tolerance tests were performed at the same interval each day (9:00 am). Insulin tolerance tests were performed with at least 2 days interevening between administering the next test. The results for the insulin tolerance tests are depicted in FIG. 13. The SBS Des$B_{30}$ Insulin derived from 4405 seed (closed diamonds) behaved almost identically (was statistically not different, $p<0.05$) to Humulin R® (open squares) and Roche Insulin (open triangles standards following injection over the course of the study. All insulin(s) tested significantly reduced plasma glucose levels ($p<0.05$) in comparison to saline placebo (open circles) and typsin cleaved wild type *Arabidopsis* oil bodies (closed circles) (negative control).

Example 7

Construction of pSBS4401: PRS-Klip27-MI-fusion Protein

One of the fusion proteins studied began with the tobacco pathogen related sequence (PRS) (Sijmons et al., 1990, Bio/technology, 8:217-221) which served as the signal peptide to target expression to the ER in a co-translational manner. Immediately downstream was a trypsin cleavable pro-peptide (KLIP27) derived from the TA57 pro-peptide of yeast (Kjeldsen et al., 2001, Biotechnology and Genetic Engineering Reviews 18:89-121). This was followed by mini-insulin (MI) described by Kjeldsen et al. (2001).

The backbone of this plasmid, pSBS4055, was based on the plant binary vector, pPZP200, described by Hajdukiewicz et al. (Plant Molecular Biology, 1994, 25:989-994). In place of the described multiple cloning site, a pat gene conferring host plant phosphinothricine resistance (Wohlleben et al., 1988, Gene 70:25-37)) driven by the ubiquitin promoter/terminator from *Petroselinum crispum* (Kawalleck et al., 1993, Plant. Mol. Bio., 21:673-684), was inserted between the left and right border sequences. In addition to this cassette, the β-phaseolin promoter/terminator from *Phaseolus vulgaris* (Slightom et al., 1983, Proc. Natl. Acad. Sc. USA 80:1897-1901) driving PRS was sub-cloned. Standard PCR (Horton et al., 1989, Gene 77:61-68) was used to fuse the synthetic PRS-encoding sequence with attached SphI/HindIII restriction endonuclease sites to the 3' end of the phaseolin promoter to yield pSBS4011.

The Klip27-MI sequence was synthesized from four partially overlapping oligonucleotides which incorporated *Arabidopsis thaliana* codon usage to increase the success of efficient translation in a plant-based expression system. Oligonucleotides 1324 (GAAGAAGGAGAGCCTAAGTTTGTTAATCAACATCTTTGTGGATCTCATC TTGTTGAGGCTCTCTACCTTG)—SEQ ID NO:177 and 1323 (CCTTAGGAGTGTAGAAAAATCCTCTTTCTCC ACACACAAGGTAGAGAGCCTCAACA)—SEQ ID NO:178 were annealed at their complimentary 20 nucleotide overlap and extended to form the 5' end of the Klip27-MI fusion while the same was done with oligonucleotides 1322 (CTAAGGCTGCTAAGGGAATTG)—SEQ ID NO:179 and 1321 (AAGCTTCAGTTGCAATAGTTCTCCAATTGG TAAAGTGAGCAAATAGAAGTGCAACATTGTTCAAC AATTCCCTTAGCAGCCTT)—SEQ ID NO:180 to form the 3' end. The two halves were ligated following restriction digestion with Bsu36I, to yield the full Klip27-MI coding sequence. PCR of this gene fusion using primers 1363 (GCATGCCCAACCAATTGATGACACTG)—SEQ ID NO:184 and primer 1329 (AAGCTTCAGTTGCAATAGTTC)—SEQ ID NO:183 attached a 5' SphI and 3' HindIII restriction endonuclease cleavage site for subsequent ligation into SphI/HindIII-cut pSBS4011 (as mentioned above). The result was plasmid pSBS4401: a DNA sequence (SEQ ID NO:188) encoding the PRS-Klip27-MI fusion protein (SEQ ID NO:189) being placed in a binary vector under expression control of the phaseolin promoter/terminator. The phaseolin promoter controls the specific-temporal and tissue-specific expression of the transgene during seed development.

Transformation and Growth of Recombinant *E. coli* and *Agrobacterium* with pSBS4401.

After confirming the integrity of the cDNA encoding for the fusion protein by sequence analysis, the plasmids pSBS4401 was transformed into *E. coli* strain DH5α to allow for high level of expression. Isolated plasmid DNA (100 ng) was mixed on ice with 100 μl of DH5α competent cells for 20 min. The cells were then heat shocked at 42° C. for 45 seconds and returned to ice for 2 min. Then 1 ml of SOC media was added and the cells were incubated at 37° C. on an enviro-shaker at 225 rpm for 1 hr before plating transformed cells on LB-spectinomycin plates (10 g/L tryptone, 5 g/L yeast extract, 5 g/L NaCl, 15 g/L agar) and incubating overnight at 37° C. A single colony was used to inoculate 5 ml LB-spectinomycin broth. These cultures were grown overnight at 37° C. The recombinant plasmid was isolated from 1 ml of the overnight culture according to Qiagen mini prep. The isolated plasmid was then used to transform competent *Agrobacterium* strain EH101 (Hood et al., 1986; J. Bacteriol. 144: 732-743) by electroporation (25 μF, 2.5 kV, 200Ω). Recombinant *Agrobacterium* were plated on AB-spectinomycin/kanamycin (20× AB salts, 2 M glucose, 0.25 mg/ml $FeSo_4 7H_2O$, 1 M $MgSo_4$, 1 M $CaCl_2$) and a single colony was used to inoculate 5 ml of AB-spectinomycin/kanamycin broth. These cultures were grown overnight at 28° C. The recombinant *Agrobacterium* were then used to transform *Arabidopsis thaliana* plants by the flower dipping method (Clough et al., 1998, Plant J., 16:735-743) as described in Example 1.

Expression Levels of Insulin in *Arabidopsis thaliana*

Expression levels of the fusion protein KLIP27-MI (4401) was determined in transgenic *Arabidopsis thaliana* mature seed using the procedure outlined in Example 2 above. The transgene product was not found to be present in the cellular extracts of mature seed.

Example 8

Construction of pSBS4409:OLEO-human Proinsulin (OLEO-hPIN) Fusion Protein

This fusion protein began with the 18 kDa oleosin from *Arabidopsis thaliana* followed in-frame by the gene encoding for human proinsulin (hPIN). The expression of this fusion protein was targeted to the nascent oil bodies formed during the development of the embryo.

The backbone of this plasmid, pSBS4008, was based on the plant binary vector, pPZP200, described by Hajdukiewicz et al. (Plant Molecular Biology, 1994, 25:989-994). In place of the described multiple cloning site, a pat gene conferring host plant phosphinothricine resistance (Wohlleben et al., 1988, Gene 70:25-37)) driven by the ubiquitin promoter/terminator from *Petroselinum crispum* (Kawalleck et al., 1993, Plant. Mol. Bio., 21:673-684), was inserted between the left and right border sequences. In addition to this cassette, the β-phaseolin promoter/terminator from *Phaseolus vulgaris* (Slightom et al., 1983, Proc. Natl. Acad. Sc. USA 80:1897-1901) driving the *Arabidopsis* 18 kDa oleosin genomic sequence was sub-cloned. Standard PCR (Horton et al., 1989, Gene 77:61-68) was used to fuse the oleosin gene sequence (minus stop codon) with attached NcoI and HindIII restriction endonuclease sites to the 3' end of the phaseolin promoter to yield pSBS4008.

An NcoI-human pre-proinsulin gene-HindIII was synthesized as a single 335 bp piece by Aptagen using preferred plant codon usage. Subsequent ligation into NcoI/HindIII-cut pSBS4008 resulted in the plasmid pSBS4400: a DNA sequence encoding the Oleosin-human pre-proinsulin fusion protein being placed in a binary vector under expression control of the phaseolin promoter/terminator. The pSBS4400 plasmid served as the template to generate human proinsulin (hPIN) by standard PCR using pfu DNA polymerase with primers directed against the 5' end (1457 oligo TTCGTGAACCAACACTTG—SEQ ID NO:190) and 3' end (1458 oligo AAGCTTTCAGTTACAGTAGT—SEQ ID NO:191) including the HindIII site of the existing proinsulin region of the vector. A second fragment was amplified using pfu DNA polymerase with a primer directed against the available SphI site (oligo 1455 GCATGCATGTGTTGAGC—SEQ ID NO:192) to the 3' end of the *Arabidopsis* oleosin gene (oligo 1456 GGTAGTGTGCTGGCCA—SEQ ID NO:193) within the pSBS4400 vector. Following PCR, products were separated on an agarose gel and bands corresponding to a 267 bp (hPIN-HindIII) and 360 bp (SphI-OLEO(3' end)) fragment were gel purified using a gel extraction kit (Qiagen). The two fragments were fused by a second round of PCR amplification using Taq DNA polymerase with primers 1455 (SEQ ID NO:192) and 1458 (SEQ ID NO:193) in combination with 0.001 μM of an overlapping bridging PCR primer (oligo 1459 GGTGGCCAGCACACTACCTTCGTGAACCAACACTTGTG—SEQ ID NO:194) for two cylces with an annealing temperature of 58° C. followed by 31 cycles at 52° C. in order to amplify a 627 bp SphI-OLEO(3' end)-hPIN-HindIII fragment. The 627 bp SphI-OLEO(3' end)-hPIN-HindIII fragment was then ligated into the T/A overhang of pGEMT Easy Vector System™ (Promega) and used to transform DH5α bacteria to result in pSBS3409 (pGEMT-SphI-OLEO(3' end)-hPIN-HindIII).

The SphI/HindIII fragment from pSBS3409 was exchanged with the SphI/HindIII fragment from pSBS4400. Standard restriction digests on both pSBS3409 and pBSB4404 were performed using SphI/HindIII (New England Biolabs). Fragments were separated on 1.5% agarose gels and purified using a gel extraction kit (Qiagen). The 617 bp SphI/HindIII fragment liberated from pSBS3409 was then ligated into the SphI/HindIII acceptor site in pre-cut pSBS4400 (internal SphI/HindIII fragment removed) vector backbone using T4 DNA ligase (NEB) overnight at 15° C.

The result was plasmid pSBS4409: a DNA sequence (SEQ ID NO:195) encoding the OLEOSIN-hPIN fusion protein (SEQ ID NO:196 being placed in a binary vector under the expression control of the phaseolin promoter/terminator. The phaseolin promoter controls the specific-temporal and tissue-specific expression of the transgene during seed development.

Transformation and Growth of Recombinant *E. coli* and *Agrobacterium* with pSBS4409.

After confirming the integrity of the cDNA encoding for the fusion protein by sequence analysis, the plasmids pSBS4409 was transformed into *E. coli* strain DH5α to allow for high level of expression. Isolated plasmid DNA (100 ng) was mixed on ice with 100 μl of DH5α competent cells for 20 min. The cells were then heat shocked at 42° C. for 45 seconds and returned to ice for 2 min. Then 1 ml of SOC media was added and the cells were incubated at 37° C. on an enviro-shaker at 225 rpm for 1 hr before plating transformed cells on LB-spectinomycin plates (10 g/L tryptone, 5 g/L yeast extract, 5 g/L NaCl, 15 g/L agar) and incubating overnight at 37° C. A single colony was used to inoculate 5 ml LB-spectinomycin broth. These cultures were grown overnight at 37° C. The recombinant plasmid was isolated from 1 ml of the overnight culture according to Qiagen mini prep. The isolated plasmid was then used to transform competent *Agrobacterium* strain EH101 (Hood et al., 1986; J. Bacteriol. 144: 732-743) by electroporation (25 µF, 2.5 kV, 200Ω). Recombinant *Agrobacterium* were plated on AB-spectinomycin/kanamycin (20×AB salts, 2 M glucose, 0.25 mg/ml $FeSo_47H_2O$, 1 M $MgSo_4$, 1 M $CaCl_2$) and a single colony was used to inoculate 5 ml of AB-spectinomycin/kanamycin broth. These cultures were grown overnight at 28° C. The recombinant *Agrobacterium* were then used to transform *Arabidopsis thaliana* plants by the flower dipping method (Clough et al., 1998, Plant J., 16:735-743) as described in Example 1.

Expression Levels of Insulin in *Arabidopsis thaliana*

Figure 14:
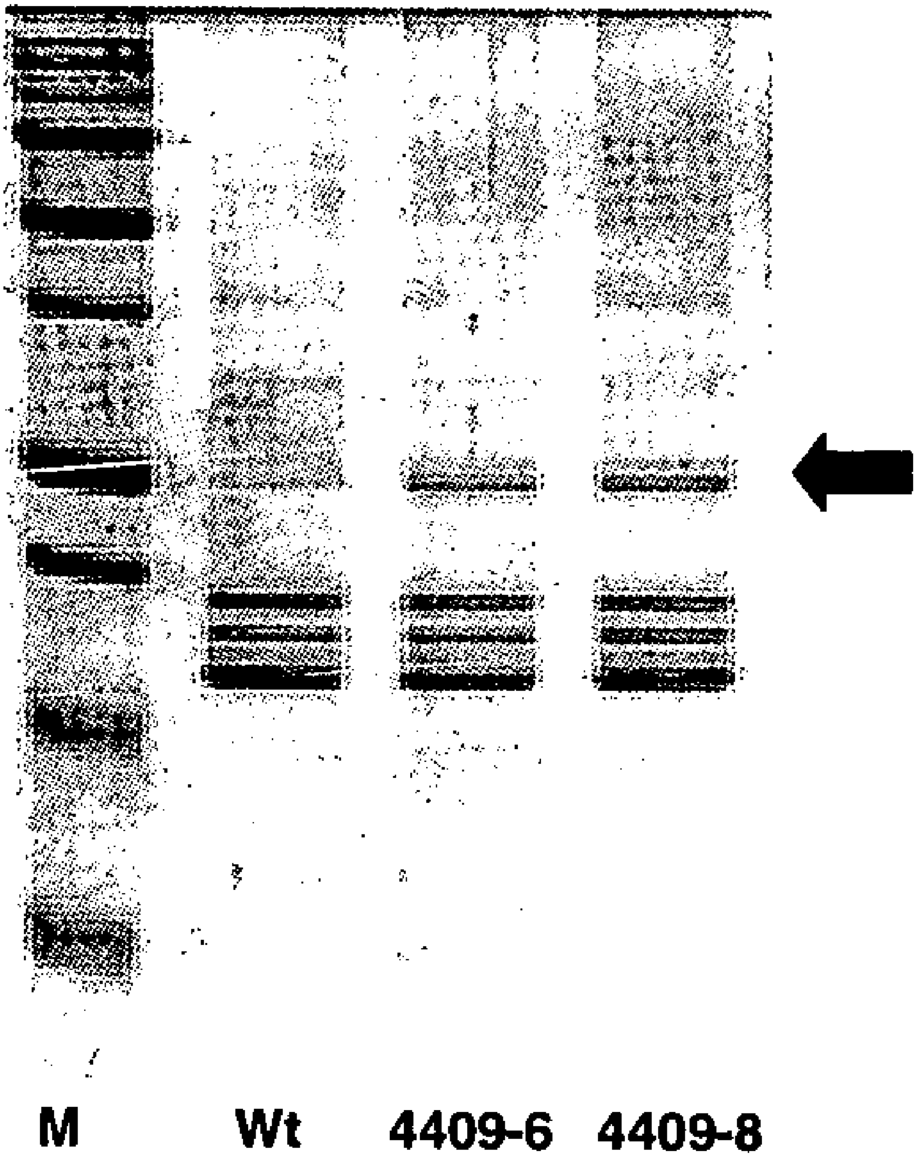
FIG. 14 depicts a Coomassie-stained gel of oil body proteins from two representative lines (4409-6 and 4409-8) comparing the migration of Oleosin-hPIN fusion protein (as denoted by the black arrow) to non-transformed (wt) *Arabidopsis*. The level of expression was determined by densitometry to measure on average about 0.10% of total seed protein. This level was calculated above and beyond the co-migration of an endogenous protein of the same molecular weight in the non-transformed seed (wt) which constituted approximately 0.04% of the total seed protein.

Expression levels of the fusion protein OLEO-hPIN (4409) was determined in transgenic *Arabidopsis thaliana* mature seed using the procedure outlined in Example 2 above. Coomassie-stained gel of oil body proteins from two representative lines (4409-6 and 4409-8) comparing the migration of Oleosin-hPIN fusion protein (as denoted by the black arrow) to non-transformed (wt) *Arabidopsis* (FIG. 14). The level of expression was determined by densitometry to measure on average about 0.10% of total seed protein. This level was calculated above and beyond the co-migration of an endogenous protein of the same molecular weight in the non-transformed seed (wt) which constituted approximately 0.04% of the total seed protein.

Example 9

Transformation of Safflower

This transformation protocol is similar to that outlined by Orlilcowska T. K. et al. ((1995) Plant Cell, Tissue and Organ Culture 40: 85-91), but with modifications and improvements both for transforming S-317 and for using phosphinothricin as the selectable marker. Decontaminate seeds from S-317 California variety of safflower, which are not damaged, cracked or diseased, in 0.1% $HCl_2$ for 12 minutes followed by 4-5 rinses with sterile distilled water. Germinate sterile seeds in the dark on MS medium (Murashige T. & Skoog F (1962) Physiol. Plant. 15: 473-497) with 1% sucrose and 0.25% GELRITE® agar substitute. Initiate *Agrobacterium* cultures from frozen glycerol stocks in 5 ml AB minimal liquid media with antibiotic selection, and grow for 48 hours at 28° C. Grow an aliquot of this culture grown overnight in 5 ml of Luria broth with selection for transformation. Wash 6-8 ml of bacterial cells twice with AB media, and make up to a final cell density of 0.4 -0.5 (0D600).

Remove two-day-old cotyledons from germinated seedlings, dip in the prepared *Agrobacterium* cells, and plate on MS medium with 3% sucrose, 4 µM N6-benzyladenine (BA) and 0.8 µM naphthaleneacetic acid (NAA). Incubate plates at 21° C. under dark conditions. After 3 days, transfer to the same medium with 300 mg/L timentin. After an additional 4 days, move all cultures to the light. After 3 days, place explants on selection medium with phosphinothricin added at 0.5 mg/L. For continued bud elongation, transfer explants weekly onto MS medium without phytohormones but with twice the basal amount of $KNO_3$. Excise shoots that had elongated to greater than 10 mm from the initial explant and individually grow on selection. For rooting, place green shoots, representing putative transgenic tissue, on MS medium with 2% sucrose, 10 µM indolebutyric acid and 0.5 µM NAA. Transfer rooted shoots to a well drained soil-less mix and grow under high humidity and 12 hours of light.

Example 10

Flax Transformation Protocol

This transformation procedure is similar to that outlined by Dong J. and McHughen A. (Plant Cell Reports (1991) 10:555-560), Dong J. and McHughen A. (Plant Sciences (1993) 88:61-71) and Mlynarova et al. (Plant Cell Reports (1994) 13: 282-285). Decontaminate flax seeds, which are not damaged, cracked or diseased, in a 70% ethanol solution for 5 to 7 minutes, followed by 25 minutes in a 50% bleach solution with Tween 20 (3-4 drops per 100 ml) with continuous stirring. Rinse seeds 5 to 7 times with sterile distilled water. Germinate decontaminated seeds in the light on MS medium (Murashige T. & Skoog F (1962) Physiol. Plant. 15: 473-497) with 2% sucrose and 0.3% GELRITE® agar substitute in Magenta jars. For transformation, grow *Agrobacterium* cultures overnight in AB broth plus the appropriate antibiotic for selection. Wash 6 to 8 ml of overnight cells twice, and re-suspended in 5 ml of AB broth; add 2 ml of this stock to 98 ml of induction medium (MS basal medium with 3% sucrose, 5 µM 6-benzylaminopurine (BA) and 0.25 µM alpha-naphthalene acetic acid (NAA) and adjust for a final $0D_{600}$ of 1.0.

Section hypocotyl explants, and inoculate in the prepared *Agrobacterium* cell solution for about 4 h (stir plates gently 1-2 times during this period). After the infection period, remove explants from the liquid inoculation medium and blot on sterile filter paper. Plate 15-20 explants on 0.7% agar-solidified induction medium in tissue culture plates. Seal the plates with plastic wrap, and co-cultivate explants for 48 h under light conditions (23-24° C.). After 2 days, transfer the green, meristematic explants to the same medium containing 300 mg/L TIMENTIN® (ticarcillin sodium/potassium clavulanate) (pre-selection media) and wrap with plastic wrap. After 3 days, transfer the cultures to the above medium containing 10 mg/L DL PPT (Selection 1). Wrap the plates with PARAFILM® sheet and incubate at 24° C. under light conditions. Transfer cultures every two weeks and keep on this media for one month. For shoot elongation, transfer the cultures every two weeks on selection medium II (MS basal medium containing 2% sucrose, 500 mg/L MES buffer, 300 mg/L TIMENTIN® (ticarcillin sodium/potassium clavulanate) and 10 mg/L DL PPT) in Magenta jars. Putative transformed shoots, which survived selection, are dark green and form vigorous roots in 7-10 days when planted individually on selection II media. Transfer rooted shoots to sterilized greenhouse soil mix in small pots and cover plantlets with clear plastic cups for acclimatization. For maturation, transfer actively growing plants to one-gallon pots with a well-drained soil mix and grow under greenhouse conditions.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Examples of Known Insulin Sequences

| SEQ. ID NO. | Insulin Motif (Amino Acid Sequence Identifier) {Nucleic Acid Sequence Identifier} |
|---|---|
| | Human Native Insulin |
| 7 | (P01308) Human preproinsulin {Comprises genes V00565, M10039, J00265, X70508, L15440, BC005255 and AJ009655} |
| | Nonhuman Native Insulin Mammals |
| 8 | (AAB25818) Proinsulin C-peptide *Equus przewalskii* (horses, zebra, rhino, and tapir (Perissodactyla)) |
| 9 | (P01310) Preproinsulin *Equus caballus* (horse) |
| 10 | (P01311) Preproinsulin {Encompasses genes U03610, and M61153} *Oryctolagus cuniculus* (domestic rabbit) |
| 11 | (P01312) insulin *Balaenoptera physalus* (finback whale) |
| 12 | (P01314) Insulin *Balaenoptera borealis* (sei whale) |
| 13 | (P01315) Preproinsulin {Comprises genes AF064555 and AY044828} *Sus scrofa* (pig) swine |
| 14 | (P01316) Insulin *Elephas maximus* (Asiatic elephant) |
| 15 | (P01317) Preproinsulin {Gene M54979} *Bos taurus* (cow) |
| 16 | (P01318) Preproinsulin {Gene U00659}*Ovis aries* (sheep) |
| 17 | (P01320) Insulin *Camelus dromedarius* (Arabian camel) |
| 18 | (P01321) Preproinsulin {Gene V00179} *Canis* sp. (canine) |
| 19 | (P01328) Insulin *Hystrix cristata* (crested porcupine) |
| 20 | (P10604) Preproinsulin {Gene J02989} *Aotus trivirgatus* (douroucouli) owl monkey |
| 21 | (P30406) Preproinsulin {Gene J00336} *Macaca fascicularis* (crab-eating macaque) |
| 22 | (P30407) Preproinsulin {Gene X61092} *Cercopithecus aethiops* (Africa green monkey) |
| 23 | (P30410) Preproinsulin {Gene X61089} *Pan troglodytes* (chimpanzee) |
| 24 | (Q9TQY7) Insulin *Ornithorhynchus anatinus* (platypus) |
| 25 | (AAM76641) Insulin {Gene AY092024} *Pongo pygmaeus* (orangutan) |
| 26 | (AAN06935) preproinsulin {Genes: AH011815 (containing AY137498, AY137499, and AY137500)} *Gorilla gorilla* (*gorilla*) |
| 27 | (INMKSQ) Insulin *Saimiri sciureus* (common squirrel monkey) |
| 28 | (P01313) Preproinsulin {Gene M26328} *Cricetulus longicaudatus* (long-tailed hamster) |
| 29 | (P01322) Insulin 1 precursor {Encompasses genes V01242, V01242, and M25584} *Rattus norvegicus* (Norway rat) |
| 30 | (P01323) Insulin 2 precursor {Encompasses genes V01243, J00748, M25583, and M25585} *Rattus norvegicus* (Norway rat) |
| 31 | (P01324) Insulin *Acomys cahirinus* (Egyptian spiny mouse) |
| 32 | (P01325) Insulin 1 precursor {Encompasses genes X04725, and AK007482} *Mus musculus* (house mouse) |
| 33 | (P01326) Insulin 2 precursor {Gene X04724} *Mus musculus* (house mouse) |
| 34 | (P01327) Insulin *Chinchilla brevicaudata* (*chinchilla*) |
| 35 | (P01329) Preproinsulin {Encompasses genes K02233, and M11713} *Cavia porcellus* (domestic guinea pig) |
| 36 | (P17715) Preproinsulin {Gene M57671} *Octodon degus* (degu) |
| 37 | (P18109) Insulin *Didelphis virginiana* (North American opossum) |
| 38 | (P21563) Preproinsulin [*Rodentia* sp.] |
| 39 | (Q62587) Preproinsulin {Gene X98241} *Psammomys obesus* (fat sand rat) |
| 40 | (Q91XI3) Preproinsulin {Gene AY038604} *Spermophilus tridecemlineat* (thirteen-lined ground squirrel) |
| 41 | (740063A) Insulin C peptide *Cavia porcellus* (domestic guinea pig) |
| | Birds |
| 42 | (P01332) Preproinsulin {Encompasses genes AH002454 (containing, J00872, J00873, and J00874), V00416, V00418, and X58993}*Gallus gallus* (chicken) |
| 43 | (P01333) Preproinsulin *Anas platyrhynchos* (mallard duck) |
| 44 | (P07454) Insulin *Anser anser anser* (western graylag goose) |
| 45 | (P51463) Preproinsulin {Genes: AH006925 (containing S66611, and S66612)} *Selasphorus rufus* (rufous hummingbird) |
| | Fish |
| 46 | (O73727) Preproinsulin {Gene: AF036326} *Danio rerio* (zebrafish) |
| 47 | (P01335) Preproinsulin {Gene: X00989} *Cyprinus carpio* (common carp) |
| 48 | (P01337) Insulin *Batrachoididae* gen. sp. (toadfish) |
| 49 | (P01339) Insulin *Thunnus thynnus* (bluefin tuna) |
| 50 | (P01340) Insulin *Katsuwonus pelamis* (skipjack tuna) |
| 51 | (P01341) Preproinsulin {Gene: V00634} *Lophius piscatorius* (angler/goose fish) |

TABLE 1-continued

Examples of Known Insulin Sequences

| SEQ. ID NO. | Insulin Motif (Amino Acid Sequence Identifier) {Nucleic Acid Sequence Identifier} |
|---|---|
| 52 | (P01342) Preproinsulin {Gene: V00649} *Myxine glutinosa* (Atlantic hagfish) |
| 53 | (P04667) Preproinsulin {Encompasses genes: X00148, J00936, K01655, and X13559} *Oncorhynchus keta* (chum salmon) |
| 54 | (P07453) *Myoxocephalus scorpius* (daddy sculpin) |
| 55 | (P09476) Insulin *Lepisosteus spatula* (alligator gar) |
| 56 | (P09477) Insulin *Platichthys flesus* (European flounder) |
| 57 | (P09536) Insulin *Hydrolagus colliei* (spotted ratfish) |
| 58 | (P12704) Insulin *Squalus acanthias* (spiny dogfish) |
| 59 | (P12705) Preproinsulin *Torpedo marmorata* (marbled electric ray) |
| 60 | (P13190) Proinsulin {Gene: U82395} *Callorhinchus milii* (elephant fish) |
| 61 | (P14806) Insulin *Petromyzon marinus* (sea lamprey) |
| 62 | (P23187) Insulin *Oncorhynchus gorbuscha* (pink salmon) |
| 63 | (P29335) Insulin *Amia calva* (bowfin) |
| 64 | (P42633) Insulin *Anguilla rostrata* (American eel) |
| 65 | (P81025) Preproinsulin {Gene: AF038123} *Oreochromis niloticus* (Nile tilapia) |
| 66 | (P81423) Insulin *Acipenser gueldenstaedtii* (Russian sturgeon) |
| 67 | (P81881) Insulin *Piaractus mesopotamicus* (Pacu) |
| 68 | (Q9W7R2) Preproinsulin {Gene AB029318} *Verasper moseri* (barfin flounder) |
| 69 | (1603264A) Insulin C Peptide *Anguilla anguilla* (European Eel) |
| | Amphibians |
| 70 | (P12706) Insulin 1 precursor {Gene: M24443} *Xenopus laevis* (Africa clawed frog) |
| 71 | (P12707) Insulin 2 precursor {Gene: M24442} *Xenopus laevis* (African clawed frog) |
| | Reptiles |
| 72 | (P31887) Insulin *Trachemys scripta* (red-eared slider turtle) |
| 73 | (P12703) Insulin *Alligator mississippiensis* (American alligator) |
| 74 | (P12708) Insulin *Zaocys dhumnades* (snake) |
| 75 | (P01334) Insulin *Crotalus atrox* (western diamondback rattlesnake) |
| | Engineered Insulin Human |
| 76 | (AAA72172) Synthetic preproinsulin {Gene: J02547} |
| 77 | (AAA72916) Synthetic insulin alpha chain 3' end {Genes: AH003171 or M38610} |
| 78 | (AAA72917) Synthetic insulin beta chain 3' end {Genes: AH003171 or M38611} |
| 79 | (CAA00712) Synthetic insulin {Gene: A07755} |
| 80 | (CAA00713) Synthetic insulin {Gene: A07758} |
| 81 | (CAA00714) Synthetic insulin {Gene: A07761} |
| 82 | (CAA00715) Unnamed protein product {Gene: A07764} |
| 83 | (CAA00736) Synthetic proinsulin {Gene: A08012} (EP 0367163-A) |
| 84 | (CAA00783) Synthetic insulin {Gene: A08468} (EP 0376156-A) |
| 85 | (CAA01581) Modified insulin precursor {Gene: A21951} (WO 9011299) |
| 86 | (CAA01254) Synthetic insulin {Gene: A15938} (EP 0214826-A) |
| 87 | (CAA01799) Asp(B1), Asp(B4), Asp(B10), Asp(B16), Glu(B27) insulin synthetic construct {Gene: A26317} |
| 88 | (CAA01798) Glu(B9), Glu(A12) insulin precursor synthetic construct {Gene: A26314} |
| 89 | (CAA23424) Synthetic proinsulin {Gene: V00082} |
| 90 | (CAA24707) Synthetic insulin C chain {Gene: V01461} |
| 91 | (CAA25151) Synthetic insulin B chain {Gene: X00462} |
| 92 | (CAD60056) Unnamed synthetic protein product {Gene: AX573757} (Pat. WO 02/079250) |
| 93 | (Gene: M31026) Synthetic human insulin B and mini-C chains using deactivated silica gel chromatography |
| 94 | (1BZVA) Chain A [d-Alab26]-Des(B27-B30)-Insulin-B26-Amide A Superpotent Single-Replacement Insulin Analogue |
| 95 | (1BZVB) Chain B [d-Alab26]-Des(B27-B30)-Insulin-B26-Amide A Superpotent Single-Replacement Insulin Analogue |
| 96 | (1HUIA) Chain A Insulin Mutant (B1, B10, B16, B27)glu, Des-B30, Nmr |
| 97 | (1HUIB) Chain B Insulin Mutant (B1, B10, B16, B27)glu, Des-B30, Nmr |
| 98 | (1HLSA) Chain A Human Insulin Mutant-His(B16) |
| 99 | (1HLSB) Chain B Human Insulin Mutant-His(B16) |
| 100 | (1JCAA) Chain A Non-Standard Design Of Unstable Insulin Analogues With Enhanced Activity |
| 101 | (1JCAB) Chain B Non-Standard Design Of Unstable Insulin Analogues With Enhanced Activity |

TABLE 1-continued

Examples of Known Insulin Sequences

| SEQ. ID NO. | Insulin Motif (Amino Acid Sequence Identifier) {Nucleic Acid Sequence Identifier} |
|---|---|
| 102 | (1JCAC) Chain C Non-Standard Design Of Unstable Insulin Analogues With Enhanced Activity |
| 103 | (1JCAD) Chain D Non-Standard Design Of Unstable Insulin Analogues With Enhanced Activity |
| 104 | (1J73A) Chain A Of An Unstable Insulin Analog With Native Activity |
| 105 | (1J73B) Chain B Of An Unstable Insulin Analog With Native Activity |
| 106 | (1J73C) Chain C Of An Unstable Insulin Analog With Native Activity |
| 107 | (1J73D) Chain D Of An Unstable Insulin Analog With Native Activity |
| 108 | (1KMFA) Chain A of Human Insulin Mutant Ile-A2-Allo-Ile, His-B10-Asp, Pro-B28-Lys, Lys-B29-Pro |
| 109 | (1KMFB) Chain B Of Human Insulin Mutant Ile-A2-Allo-Ile, His-B10-Asp, Pro-B28-Lys, Lys-B29-Pro |
| 110 | (1K3MA) Chain A Of Human Insulin Mutant Ile-A2-Ala, His-B10-Asp, Pro-B28-Lys, Lys-B29-Pro |
| 111 | (1K3MB) Chain B of Human Insulin Mutant Ile-A2-Ala, His-B10-Asp, Pro-B28-Lys, Lys-B29-Pro |
| 112 | (1LW8A) Chain A Allo-Ilea2-Insulin, An Inactive Chiral Analogue |
| 113 | (1LW8B) Chain B Allo-Ilea2-Insulin, An Inactive Chiral Analogue |
| 114 | (1LW8C) Chain C Allo-Ilea2-Insulin, An Inactive Chiral Analogue |
| 115 | (1LW8D) Chain D Allo-Ilea2-Insulin, An Inactive Chiral Analogue |
| 116 | (1LKQA) Chain A of Human Insulin Mutant Ile-A2-Gly, Val-A3-Gly, His-B10-Asp, Pro-B28-Lys, Lys-B29-Pro |
| 117 | (1LKQB) Chain B of Human Insulin Mutant Ile-A2-Gly, Val-A3-Gly, His-B10-Asp, Pro-B28-Lys, Lys-B29-Pro |
| 118 | (1MHIA) Chain A of B9(Asp) mutant |
| 119 | (1MHIB) Chain B of B9(Asp) mutant |
| 120 | (1MHJA) Chain A of B25(phe) mutant |
| 121 | (1MHJB) Chain B of B25(phe) mutant |
| 122 | (1VKTA) Chain A, Human Insulin Two Disulfide Model |
| 123 | (1VKTB) Chain B, Human Insulin Two Disulfide Model |
| | Non-Human |
| 124 | (AAG59607) Synthetic albebetin insulin {Gene: AY017185} |
| 125 | (AAG59606) Synthetic albeferon insulin {Gene: AY017184} |
| | Insulin Fusion Proteins<br>Human |
| 126 | (AAB27046) N-terminal of an interlekukin 2-insulin fusion protein |
| 127 | (AAB27047) Beta-galactosidase-insulin fusion protein N-terminal |
| 128 | (PC7082) Epidermal growth factor/Des-B30 single-chain human insulin precursor fusion protein |
| | Non-human |
| 129 | (AAA72177) *E. coli* penicillinase/rat insulin I fusion protein 5' end {G AH003149 or J02553} |
| 130 | (AAA72178) *E. coli* penicillinase/rat insulin I fusion protein 3' end {Genes: AH003149 or J02554} |
| 131 | (AAA72179) Rat insulin signal sequence/*E. coli* beta-galactosidase fusion protein {Gene: J02555} |
| 132 | (AAA72181) Simian virus 40 (SV40)/rat preproinsulin I fusion protein) {Gene: J02559} |
| | Mini Insulin<br>Human |
| 133 | (1EFEA) Chain A, An Active Mini-Proinsulin, M2pi |
| 134 | (1JCAA) Chain A, Non-Standard Design Of Unstable Insulin Analogues With Enhanced Activity |
| 135 | (1JCAB) Chain B, Non-Standard Design Of Unstable Insulin Analogues With Enhanced Activity |
| 136 | (1JCAC) Chain C, Non-Standard Design Of Unstable Insulin Analogues With Enhanced Activity |
| 137 | (1JCAD) Chain D, Non-Standard Design Of Unstable Insulin Analogues With Enhanced Activity |
| 138 | (1JK8C) Chain C, A Human Insulin Peptide-Hla-Dq8 Complex |
| 139 | (1J73A) Chain A, An Unstable Insulin Analog With Native Activity |
| 140 | (1J73B) Chain B, An Unstable Insulin Analog With Native Activity |
| 141 | (1J73C) Chain C, An Unstable Insulin Analog With Native Activity |
| 142 | (1J73D) Chain D, An Unstable Insulin Analog With Native Activity |
| 143 | (1SJTA) Chain A, Mini-Proinsulin, Two Chain Insulin Analog Mutant: Des B30,His(B 10)asp, Pro(B 28)asp |
| 144 | (1SJTB) Chain B, Mini-Proinsulin, Two Chain Insulin Analog Mutant: Des B30,His(B 10)asp, Pro(B 28)asp |

TABLE 1-continued

| Examples of Known Insulin Sequences | |
|---|---|
| SEQ. ID NO. | Insulin Motif (Amino Acid Sequence Identifier) {Nucleic Acid Sequence Identifier} |
| 145 | (1SJU) Mini-proinsulin, single chain insulin analog mutant: Des B30, His(B10)asp, Pro(B28)asp and peptide bond between Lys B29 And Gly A1 |

SUMMARY OF SEQUENCES

SEQ ID NO:1 and 2 set forth the nucleotide sequence and the deduced amino acid sequence, respectively, of the PRS-D9scFv-KLIP27-MI-KDEL fusion protein in the plasmid pSBS4404.

SEQ ID NO:3 and 4 set forth the nucleotide sequence and the deduced amino acid sequence, respectively, of the Oleo-KLIP8-KLIP27-MI fusion protein in plasmid pSBS4405.

SEQ ID NO:5 and 6 set forth the nucleotide sequence and the deduced amino acid sequence, respectively, of the PRS-MI-tetrabasic linker-D9Scfv-KDEL fusion protein in plasmid pSBS4414.

SEQ ID NO:7 to 145 set forth known insulin sequences which are described in Table 1.

SEQ ID NO:146 to 148 set forth the amino acid sequences of fragments of the insulin C-peptide.

SEQ ID NO:149 sets forth the amino acid sequence of the tetrabasic processing peptide.

SEQ ID NO:150 to 155 sets forth the amino acid sequence of the polypeptides capable of retaining the insulin polypeptide to the ER.

SEQ ID NO:156 to 160 sets forth the amino acid sequences of the polypeptides capable of retaining the insulin polypeptide to an ER derived storage organelle.

SEQ ID NO:161 sets forth the amino acid sequence of a PRS signal sequence.

SEQ ID NO:162 to 171 set forth the amino acid sequences of yeast leader sequences and sequences derived there from.

SEQ ID NO:172 to 173 set forth the amino acid sequences of spacer peptides.

SEQ ID NO:174 sets forth the amino acid sequence of the KLIP8 sequence SEQ ID NO:175 sets forth the nucleotide sequence of the forward primer 1325 which is complementary to the 5' region of the D9ScFv cDNA clone and is designed to add a SphI site to the 5' region facilitate subsequent ligation.

SEQ ID NO:176 sets forth the nucleotide sequence of the reverse primer 1326 which is complementary to the 3' region of the D9ScFv cDNA clone and is designed to add a XhoI site to the 3' region facilitate subsequent ligation.

SEQ ID NO:177 sets forth the nucleotide sequence of the forward primer 1324 which is complementary to a 20 nucleotide region of reverse primer 1323 and is designed to form the 5' end of the Klip27-MI fusion.

SEQ ID NO:178 sets forth the nucleotide sequence of the reverse primer 1323 which is complementary to a 20 nucleotide region of forward primer 1324 and is designed to form the 5' end of the Klip27-MI fusion.

SEQ ID NO:179 sets forth the nucleotide sequence of the forward primer 1322 which is complementary to a 19 nucleotide region of reverse primer 1321 and is designed to form the 3' end of the Klip27-MI fusion.

SEQ ID NO:180 sets forth the nucleotide sequence of the reverse primer 1321 which is complementary to a 19 nucleotide region of forward primer 1322 and is designed to form the 3' end of the Klip27-MI fusion.

SEQ ID NO:181 sets forth the nucleotide sequence of the forward primer 1364 which is complementary to the 5' region of the Klip27-MI sequence and is designed to add a XhoI site to the 5' region facilitate subsequent ligation.

SEQ ID NO:182 sets forth the nucleotide sequence of the reverse primer 1334 which is complementary to the 3' region of the Klip27-MI sequence and is designed to add a HindIII site to the 3' region facilitate subsequent ligation and a 3' KDEL sequence.

SEQ ID NO:183 sets forth the nucleotide sequence of the reverse primer 1329 which is complementary to the 3' region of the Klip27-MI sequence and is designed to add a HindIII site to the 3' region facilitate subsequent ligation.

SEQ ID NO:184 sets forth the nucleotide sequence of the forward primer 1363 which is complementary to the 5' region of the Klip27-MI sequence and is designed to add a SphI site to the 5' region facilitate subsequent ligation.

SEQ ID NO:185 sets forth the nucleotide sequence of the forward primer 1515 which is complementary to the 5' region of the insulin B chain sequence and is designed to insert the intervening tetrabasic site between the authentic A and B chains of human insulin in conjunction with reverse primer 1518.

SEQ ID NO:186 sets forth the nucleotide sequence of the reverse primer 1518 which is complementary to the 3' region of the insulin B chain and 5' region of the insulin A chain with the intervening tetrabasic mini-c-peptide sequence and is designed to insert the intervening tetrabasic site between the authentic A and B chains of human insulin.

SEQ ID NO:187 sets forth the nucleotide sequence of the reverse primer 1517 which is complementary to the 3' region of the_D9 scFV/KDEL sequence and is designed to amplify the entire MI-tetrabasic linker-D9Scfv-KDEL to create the pSBS4414 insert.

SEQ ID NO:188 and 189 set forth the nucleotide sequence and the deduced amino acid sequence, respectively, of the PRS-Klip27-MI fusion protein in plasmid pSBS4401.

SEQ ID NO:190 sets forth the nucleotide sequence of the forward primer 1457 which is complementary to the 5' region of the insulin B chain sequence and is designed to generate the human proinsulin (hRIN) fragment in conjunction with reverse primer 1591.

SEQ ID NO:191 sets forth the nucleotide sequence of the reverse primer 1458 which is complementary to the 3' region of human proinsulin (hPIN) is designed to generate the human pro(hPIN) and add a 3' HindIII cloning site.

SEQ ID NO:192 sets forth the nucleotide sequence of the forward primer 1455 which is complementary to the 5' region of the SphI site of pSBS4404 and is designed amplify the *Arabidopsis* oleosin gene in conjunction with reverse primer 1456.

SEQ ID NO:193 sets forth the nucleotide sequence of the reverse primer 1456 which is complementary to the 3' region of the *Arabidopsis* oleosin gene and is designed amplify the *Arabidopsis* oleosin gene in conjunction with forward primer 1455.

SEQ ID NO:194 sets forth the nucleotide sequence of the overlapping bridging PCR primer which is complementary to the 3' region of the *Arabidopsis* oleosin gene and the 5' end of the human proinsulin gene and is designed to create the pSBS4409 insert inconjunction with forward primer 1455 and reverse primer 1456.

SEQ ID NO:195 and 196 set forth the nucleotide sequence and the deduced amino acid sequence, respectively, of the OLEO-hPIN fusion protein in plasmid pSBS4409.

What we claim as our invention is:

1. A method for the expression of insulin in plant seeds comprising:

(a) providing a chimeric nucleic acid construct comprising in the 5' to 3' direction of transcription as operably linked components:

(i) a first nucleic acid sequence that comprises a seed-preferred promoter;

(ii) a second nucleic acid sequence encoding a signal peptide and an insulin polypeptide; and (iii) a third nucleic acid sequence that encodes a single chain antibody that has specificity for an oil body;

(b) introducing the chimeric nucleic acid construct into a plant cell;

(c) growing the plant cell into a mature plant capable of setting seed; and (d) obtaining substantially pure insulin from said seeds.

2. The method according to claim 1, wherein the insulin polypeptide accumulates within a membrane enclosed intracellular compartment within the plant cell.

3. The method according to claim 2, wherein said membrane enclosed intracellular compartment is the endoplasmic reticulum (ER) or an ER-derived storage vesicle.

4. The method according to claim 1, wherein said chimeric nucleic acid sequence additionally comprises a forth nucleic acid sequence that (a) encodes a polypeptide which is capable of retaining the insulin polypeptide in a membrane enclosed intracellular compartments and (b) is operably linked to said second nucleic acid sequence.

5. The method according to claim 4, wherein said membrane enclosed intracellular compartment is the endoplasmic reticulum (ER) or an ER-derived storage organelle.

6. The method according to claim 5, wherein said polypeptide retaining the insulin polypeptide in the ER is selected from the group consisting of SEQ ID NO:150, SEQ ID NO:151, SEQ ID NO:152, SEQ ID NO:153 and SEQ ID NO:154.

7. The method according to claim 1, wherein said signal peptide is a tobacco pathogenesis related protein (PR-S) signal sequence.

8. The method according to claim 1, wherein said signal peptide is SEQ ID NO:161.

9. The method according to any one of claims 1-5, 6, 7, and 8, wherein the seed-preferred promoter is a phaseolin promoter.

10. The method according to any one of claims 1-5, 6, 7, and 8, wherein said second nucleic acid sequence encodes a protein selected from the group consisting of human insulin, porcine insulin, and bovine insulin.

11. The method according to any one of claims 1-5, 6, 7, and 8, wherein said second nucleic acid encodes a mini-insulin.

12. The method according to any one of claims 1-5, 6, 7, and 8, wherein said second nucleic acid is optimized for plant codon usage.

13. A plant capable of setting seed, wherein seeds of said plant comprise a chimeric nucleic acid sequence that comprises in the 5' to 3' direction of transcription:

(a) a first nucleic acid sequence that comprises a seed-preferred promoter operatively linked to;

(b) a second nucleic acid sequence encoding a signal peptide and an insulin polypeptide; and (c) a third nucleic acid sequence that encodes a single chain antibody that has specificity for an oil body.

14. The plant according to claim 13, wherein the plant is an *Arabidopsis,* flax, or safflower plant.

15. A plant seed comprising a chimeric nucleic acid sequence that comprises in the 5' to 3' direction of transcription:

(a) a first nucleic acid sequence that comprises a seed-preferred promoter that is operatively linked to;

(b) a second nucleic acid sequence encoding a signal peptide and an insulin polypeptide; and (c) a third nucleic acid sequence that encodes a single chain antibody that has specificity for an oil body.

16. A polynucleotide comprised of (i) a first nucleic acid sequence that encodes insulin, and (ii) a second nucleic acid sequence that encodes a single chain antibody that has specificity for an oil body, and (iii) a third nucleic acid encoding a signal peptide operatively linked to (iv) a seed-preferred promoter.

17. The polynucleotide according to claim 16, wherein said seed-preferred promoter is a phaseolin promoter.

18. The polynucleotide according to claim 16, further comprising a nucleic acid sequence that encodes a sequence capable of retaining the insulin polypeptide in a membrane enclosed intracellular compartment.

19. The polynucleotide according to claim 16, further comprising a nucleic acid sequence that encodes a sequence capable of retaining the insulin polypeptide in the ER or an ER-derived storage organelle.

20. The method according to claim 1, wherein said plant is a dicotyledonous plant.

21. The plant according to claim 13, wherein said plant is a dicotyledonous plant.

22. The method according to claim 1, wherein seeds of said plant contain insulin in an amount between about 0.1% and 0.79% of total soluble seed protein.

23. The plant seed according to claim 15, wherein said seed comprises insulin in an amount between about 0.1% and 0.79% of total soluble seed protein.

24. A method for the commercial production of insulin, comprising (a) providing a plurality of seeds that comprise (i) a first polynucleotide coding for insulin operatively linked to (ii) a second polynucleotide that encodes a single chain antibody that has specificity for an oil body, and (iii) a third polynucleotide that encodes a signal peptide, wherein said seeds contain insulin; and (b) obtaining substantially pure insulin from said plurality.

25. The method according to claim 24, wherein said insulin is present in the seed in an amount between about 0.1% and 0.79% of total soluble seed protein.

26. A method for obtaining insulin-producing plants, comprising (a) providing a plurality of seeds that comprise (i) a first polynucleotide coding for insulin operatively linked to (ii) a second polynucleotide that encodes a single chain antibody that has specificity for an oil body, and (iii) a third polynucleotide that encodes a signal peptide, wherein said seeds contain insulin; and (b) using at least some seeds of said plurality to produce a population of plants, wherein plant of said population produce seeds that comprise insulin.

27. The method according to claim 26, wherein insulin is present in seed in an amount between about 0.1% and 0.79% of total soluble seed protein.

28. The method according to claim 3, wherein said membrane enclosed intracellular compartment is the ER.

29. The polynucleotide according to claim 19, wherein said nucleic acid sequence encodes a sequence capable of retaining the insulin polypeptide in the ER.

* * * * *

SEQUENCE LISTING

```
<160> NUMBER OF SEQ ID NOS: 196

<210> SEQ ID NO 1
<211> LENGTH: 1143
<212> TYPE: DNA
<213> ORGANISM: Artificial Sequence
<220> FEATURE:
<223> OTHER INFORMATION: Insulin fusion protein nucleic acid sequence

<400> SEQUENCE: 1

atgaacttcc ttaagtcttt ccctttctac gctttccttt gtttcggtca atacttcgtt      60

gctgttacgc atgctgacat tgtgatgaca cagtctccat cctccctggc tatgtcagtg     120

ggacagcggg tcactatgcg ctgcaagtcc agtcagagcc ttttaaaaag taccaatcaa     180

aagaactatt tggcctggta ccagcagaaa ccaggacagt ctcctaaact tctggtatac     240

tttgcatcca ctagggaatc tggggtccct gatcgcttca taggcagtgg atctgggaca     300

gatttcactc ttaccatcag cagtgtgcag gctgaagacc tggcagatta cttctgtcag     360

caacattata acactcctcc cacgttcggt gctgggacca agctggagct taagcggtct     420

ccgaacggtg cttctcatag cggttctgca ccaggcacta gctctgcatc tggatctcag     480

gtgcacctgc agcagtctgg agctgagctg atgaagcctg gggcctcaat gaagatatcc     540

tgcaaggcta ctggctacac attcagtagc tactggatag agtgggtaaa gcagaggcct     600

ggacatggcc ttgagtggat tggagagatt ttacctggca gtggtagtac tacctacaat     660

gagaagttca agggcaaggc cacattcact gcagatacat cctccaacac agcctacatg     720

caactcagca gcctgacatc tgaggactct gccgtctatt actgtgcaag attggatgtt     780

gactcctggg gccaaggcac cactctcaca gtctcgagtc aaccaattga tgacactgaa     840

tcccagacca cgtcagtgaa cctcatggcc gatgatactg agagcgcgtt tgctacacaa     900

acaaattcgg gaggtcttga cgttgtcgga ttgatctcca tggctaagag agaagaagga     960

gagcctaagt ttgttaatca acatctttgt ggatctcatc ttgttgaggc tctctacctt    1020

gtgtgtggag aaagaggatt tttctacact cctaaggctg ctaagggaat tgttgaacaa    1080

tgttgcactt ctatttgctc actttaccaa ttggagaact attgcaacaa ggatgaactt    1140

tga                                                                  1143


<210> SEQ ID NO 2
<211> LENGTH: 380
<212> TYPE: PRT
<213> ORGANISM: Artificial Sequence
<220> FEATURE:
<223> OTHER INFORMATION: Insulin fusion protein

<400> SEQUENCE: 2

Met Asn Phe Leu Lys Ser Phe Pro Phe Tyr Ala Phe Leu Cys Phe Gly
1               5                   10                  15

Gln Tyr Phe Val Ala Val Thr His Ala Asp Ile Val Met Thr Gln Ser
            20                  25                  30
```

-continued

```
Pro Ser Ser Leu Ala Met Ser Val Gly Gln Arg Val Thr Met Arg Cys
        35                  40                  45

Lys Ser Ser Gln Ser Leu Leu Lys Ser Thr Asn Gln Lys Asn Tyr Leu
    50                  55                  60

Ala Trp Tyr Gln Gln Lys Pro Gly Gln Ser Pro Lys Leu Leu Val Tyr
65                  70                  75                  80

Phe Ala Ser Thr Arg Glu Ser Gly Val Pro Asp Arg Phe Ile Gly Ser
                85                  90                  95

Gly Ser Gly Thr Asp Phe Thr Leu Thr Ile Ser Ser Val Gln Ala Glu
            100                 105                 110

Asp Leu Ala Asp Tyr Phe Cys Gln Gln His Tyr Asn Thr Pro Pro Thr
        115                 120                 125

Phe Gly Ala Gly Thr Lys Leu Glu Leu Lys Arg Ser Pro Asn Gly Ala
    130                 135                 140

Ser His Ser Gly Ser Ala Pro Gly Thr Ser Ser Ala Ser Gly Ser Gln
145                 150                 155                 160

Val His Leu Gln Gln Ser Gly Ala Glu Leu Met Lys Pro Gly Ala Ser
                165                 170                 175

Met Lys Ile Ser Cys Lys Ala Thr Gly Tyr Thr Phe Ser Ser Tyr Trp
            180                 185                 190

Ile Glu Trp Val Lys Gln Arg Pro Gly His Gly Leu Glu Trp Ile Gly
        195                 200                 205

Glu Ile Leu Pro Gly Ser Gly Ser Thr Thr Tyr Asn Glu Lys Phe Lys
    210                 215                 220

Gly Lys Ala Thr Phe Thr Ala Asp Thr Ser Ser Asn Thr Ala Tyr Met
225                 230                 235                 240

Gln Leu Ser Ser Leu Thr Ser Glu Asp Ser Ala Val Tyr Tyr Cys Ala
                245                 250                 255

Arg Leu Asp Val Asp Ser Trp Gly Gln Gly Thr Thr Leu Thr Val Ser
            260                 265                 270

Ser Gln Pro Ile Asp Asp Thr Glu Ser Gln Thr Thr Ser Val Asn Leu
        275                 280                 285

Met Ala Asp Asp Thr Glu Ser Ala Phe Ala Thr Gln Thr Asn Ser Gly
    290                 295                 300

Gly Leu Asp Val Val Gly Leu Ile Ser Met Ala Lys Arg Glu Glu Gly
305                 310                 315                 320

Glu Pro Lys Phe Val Asn Gln His Leu Cys Gly Ser His Leu Val Glu
                325                 330                 335

Ala Leu Tyr Leu Val Cys Gly Glu Arg Gly Phe Phe Tyr Thr Pro Lys
            340                 345                 350

Ala Ala Lys Gly Ile Val Glu Gln Cys Cys Thr Ser Ile Cys Ser Leu
        355                 360                 365

Tyr Gln Leu Glu Asn Tyr Cys Asn Lys Asp Glu Leu
    370                 375                 380
```

<210> SEQ ID NO 3
<211> LENGTH: 945
<212> TYPE: DNA
<213> ORGANISM: Artificial Sequence
<220> FEATURE:
<223> OTHER INFORMATION: Insulin fusion protein nucleic acid sequence

<400> SEQUENCE: 3

```
atggcggata cagctagagg aacccatcac gatatcatcg gcagagacca gtacccgatg      60

atgggccgag accgagacca gtaccagatg tccggacgag gatctgacta ctccaagtct     120
```

-continued

```
aggcagattg ctaaagctgc aactgctgtc acagctggtg gttccctcct tgttctctcc    180

agccttaccc ttgttggaac tgtcatagct ttgactgttg caacacctct gctcgttatc    240

ttcagcccaa tccttgtccc ggctctcatc acagttgcac tcctcatcac cggttttctt    300

tcctctggag ggtttggcat tgccgctata accgttttct cttggattta cgcaacggga    360

gagcacccac agggatcaga caagttggac agtgcaagga tgaagttggg aagcaaagct    420

caggatctga aagacagagc tcagtactac ggacagcaac atactggtgg ggaacatgac    480

cgtgaccgta ctcgtggtgg ccagcacact accatggctg agatcacccg cattcctctc    540

tacaaaggta agtctctccg taaggcgctg aaggaacatg gacttctaga agacttcttg    600

cagaaacaac agtatggcat ctcgagcaag ttccaaccaa ttgatgacac tgaatcccag    660

accacgtcag tgaacctcat ggccgatgat actgagagcg cgtttgctac acaaacaaat    720

tcgggaggtc ttgacgttgt cggattgatc tccatggcta agagagaaga aggagagcct    780

aagtttgtta atcaacatct ttgtggatct catcttgttg aggctctcta ccttgtgtgt    840

ggagaaagag gatttttcta cactcctaag gctgctaagg gaattgttga acaatgttgc    900

acttctattt gctcacttta ccaattggag aactattgca actga                    945
```

<210> SEQ ID NO 4
<211> LENGTH: 314
<212> TYPE: PRT
<213> ORGANISM: Artificial Sequence
<220> FEATURE:
<223> OTHER INFORMATION: Insulin fusion protein

<400> SEQUENCE: 4

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Ala Thr Gly Glu His Pro Gln Gly Ser Asp Lys
        115                 120                 125

Leu Asp Ser Ala Arg Met Lys Leu Gly Ser Lys Ala Gln Asp Leu Lys
    130                 135                 140

Asp Arg Ala Gln Tyr Tyr Gly Gln Gln His Thr Gly Gly Glu His Asp
145                 150                 155                 160

Arg Asp Arg Thr Arg Gly Gly Gln His Thr Thr Met Ala Glu Ile Thr
                165                 170                 175

Arg Ile Pro Leu Tyr Lys Gly Lys Ser Leu Arg Lys Ala Leu Lys Glu
            180                 185                 190

His Gly Leu Leu Glu Asp Phe Leu Gln Lys Gln Gln Tyr Gly Ile Ser
        195                 200                 205

Ser Lys Phe Gln Pro Ile Asp Asp Thr Glu Ser Gln Thr Thr Ser Val
```

-continued

```
    210                 215                 220

Asn Leu Met Ala Asp Asp Thr Glu Ser Ala Phe Ala Thr Gln Thr Asn
225                 230                 235                 240

Ser Gly Gly Leu Asp Val Val Gly Leu Ile Ser Met Ala Lys Arg Glu
                245                 250                 255

Glu Gly Glu Pro Lys Phe Val Asn Gln His Leu Cys Gly Ser His Leu
            260                 265                 270

Val Glu Ala Leu Tyr Leu Val Cys Gly Glu Arg Gly Phe Phe Tyr Thr
        275                 280                 285

Pro Lys Ala Ala Lys Gly Ile Val Glu Gln Cys Cys Thr Ser Ile Cys
    290                 295                 300

Ser Leu Tyr Gln Leu Glu Asn Tyr Cys Asn
305                 310


<210> SEQ ID NO 5
<211> LENGTH: 1011
<212> TYPE: DNA
<213> ORGANISM: Artificial Sequence
<220> FEATURE:
<223> OTHER INFORMATION: Insulin fusion protein nucleic acid sequence

<400> SEQUENCE: 5

atgaacttcc ttaagtcttt ccctttctac gctttccttt gtttcggtca atacttcgtt      60

gctgttacgc atgcctttgt taatcaacat ctttgtggat ctcatcttgt tgaggctctc     120

taccttgtgt gtggagaaag aggatttttc tacactccta agactagaag aaagagagga     180

attgttgaac aatgttgcac ttctatttgc tcactttacc aattggagaa ctattgcaac     240

agaagaaaga gagacattgt gatgacacag tctccatcct ccctggctat gtcagtggga     300

cagcgggtca ctatgcgctg caagtccagt cagagccttt taaaaagtac caatcaaaag     360

aactatttgg cctggtacca gcagaaacca ggacagtctc ctaaacttct ggtatacttt     420

gcatccacta gggaatctgg ggtccctgat cgcttcatag gcagtggatc tgggacagat     480

ttcactctta ccatcagcag tgtgcaggct gaagacctgg cagattactt ctgtcagcaa     540

cattataaca ctcctcccac gttcggtgct gggaccaagt tggagcttaa gcggtctccg     600

aacggtgctt ctcatagcgg ttctgcacca ggcactagct ctgcatctgg atctcaggtg     660

cacctgcagc agtctggagc tgagctgatg aagcctgggg cctcaatgaa gatatcctgc     720

aaggctactg gctacacatt cagtagctac tggatagagt gggtaaagca gaggcctgga     780

catggccttg agtggattgg agagatttta cctggcagtg gtagtactac ctacaatgag     840

aagttcaagg gcaaggccac attcactgca gatacatcct ccaacacagc ctacatgcaa     900

ctcagcagcc tgacatctga ggactctgcc gtctattact gtgcaagatt ggatgttgac     960

tcctggggcc aaggcaccac tctcacagtg agctcaaagg atgagctttg a             1011


<210> SEQ ID NO 6
<211> LENGTH: 336
<212> TYPE: PRT
<213> ORGANISM: Artificial Sequence
<220> FEATURE:
<223> OTHER INFORMATION: Insulin fusion protein

<400> SEQUENCE: 6

Met Asn Phe Leu Lys Ser Phe Pro Phe Tyr Ala Phe Leu Cys Phe Gly
1               5                   10                  15

Gln Tyr Phe Val Ala Val Thr His Ala Phe Val Asn Gln His Leu Cys
            20                  25                  30
```

-continued

Gly Ser His Leu Val Glu Ala Leu Tyr Leu Val Cys Gly Glu Arg Gly
35 40 45

Phe Phe Tyr Thr Pro Lys Thr Arg Arg Lys Arg Gly Ile Val Glu Gln
50 55 60

Cys Cys Thr Ser Ile Cys Ser Leu Tyr Gln Leu Glu Asn Tyr Cys Asn
65 70 75 80

Arg Arg Lys Arg Asp Ile Val Met Thr Gln Ser Pro Ser Ser Leu Ala
85 90 95

Met Ser Val Gly Gln Arg Val Thr Met Arg Cys Lys Ser Ser Gln Ser
100 105 110

Leu Leu Lys Ser Thr Asn Gln Lys Asn Tyr Leu Ala Trp Tyr Gln Gln
115 120 125

Lys Pro Gly Gln Ser Pro Lys Leu Leu Val Tyr Phe Ala Ser Thr Arg
130 135 140

Glu Ser Gly Val Pro Asp Arg Phe Ile Gly Ser Gly Ser Gly Thr Asp
145 150 155 160

Phe Thr Leu Thr Ile Ser Ser Val Gln Ala Glu Asp Leu Ala Asp Tyr
165 170 175

Phe Cys Gln Gln His Tyr Asn Thr Pro Pro Thr Phe Gly Ala Gly Thr
180 185 190

Lys Leu Glu Leu Lys Arg Ser Pro Asn Gly Ala Ser His Ser Gly Ser
195 200 205

Ala Pro Gly Thr Ser Ser Ala Ser Gly Ser Gln Val His Leu Gln Gln
210 215 220

Ser Gly Ala Glu Leu Met Lys Pro Gly Ala Ser Met Lys Ile Ser Cys
225 230 235 240

Lys Ala Thr Gly Tyr Thr Phe Ser Ser Tyr Trp Ile Glu Trp Val Lys
245 250 255

Gln Arg Pro Gly His Gly Leu Glu Trp Ile Gly Glu Ile Leu Pro Gly
260 265 270

Ser Gly Ser Thr Thr Tyr Asn Glu Lys Phe Lys Gly Lys Ala Thr Phe
275 280 285

Thr Ala Asp Thr Ser Ser Asn Thr Ala Tyr Met Gln Leu Ser Ser Leu
290 295 300

Thr Ser Glu Asp Ser Ala Val Tyr Tyr Cys Ala Arg Leu Asp Val Asp
305 310 315 320

Ser Trp Gly Gln Gly Thr Thr Leu Thr Val Ser Ser Lys Asp Glu Leu
325 330 335

<210> SEQ ID NO 7
<211> LENGTH: 110
<212> TYPE: PRT
<213> ORGANISM: Homo sapiens

<400> SEQUENCE: 7

Met Ala Leu Trp Met Arg Leu Leu Pro Leu Leu Ala Leu Leu Ala Leu
1 5 10 15

Trp Gly Pro Asp Pro Ala Ala Ala Phe Val Asn Gln His Leu Cys Gly
20 25 30

Ser His Leu Val Glu Ala Leu Tyr Leu Val Cys Gly Glu Arg Gly Phe
35 40 45

Phe Tyr Thr Pro Lys Thr Arg Arg Glu Ala Glu Asp Leu Gln Val Gly
50 55 60

Gln Val Glu Leu Gly Gly Gly Pro Gly Ala Gly Ser Leu Gln Pro Leu

-continued

```
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 8
<211> LENGTH: 31
<212> TYPE: PRT
<213> ORGANISM: Equus  przewalskii

<400> SEQUENCE: 8

Glu Ala Glu Asp Pro Gln Val Gly Glu Val Glu Leu Gly Gly Gly Pro
1               5                   10                  15

Gly Leu Gly Gly Leu Gln Pro Leu Ala Leu Ala Gly Pro Gln Gln
            20                  25                  30


<210> SEQ ID NO 9
<211> LENGTH: 86
<212> TYPE: PRT
<213> ORGANISM: Equus caballus
<220> FEATURE:
<221> NAME/KEY: MISC_FEATURE
<222> LOCATION: (31)..(32)
<223> OTHER INFORMATION: X = any amino acid
<220> FEATURE:
<221> NAME/KEY: MISC_FEATURE
<222> LOCATION: (64)..(65)
<223> OTHER INFORMATION: X = any amino acid

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Xaa Xaa
            20                  25                  30

Glu Ala Glu Asp Pro Gln Val Gly Glu Val Glu Leu Gly Gly Gly Pro
        35                  40                  45

Gly Leu Gly Gly Leu Gln Pro Leu Ala Leu Ala Gly Pro Gln Gln Xaa
    50                  55                  60

Xaa Gly Ile Val Glu Gln Cys Cys Thr Gly Ile Cys Ser Leu Tyr Gln
65                  70                  75                  80

Leu Glu Asn Tyr Cys Asn
                85


<210> SEQ ID NO 10
<211> LENGTH: 110
<212> TYPE: PRT
<213> ORGANISM: Oryctolagus cuniculus

<400> SEQUENCE: 10

Met Ala Ser Leu Ala Ala Leu Leu Pro Leu Leu Ala Leu Leu Val Leu
1               5                   10                  15

Cys Arg Leu Asp Pro Ala Gln Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Ser Arg Arg Glu Val Glu Glu Leu Gln Val Gly
    50                  55                  60

Gln Ala Glu Leu Gly Gly Gly Pro Gly Ala Gly Gly Leu Gln Pro Ser
65                  70                  75                  80
```

-continued

```
Ala Leu Glu Leu Ala Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 11
<211> LENGTH: 21
<212> TYPE: PRT
<213> ORGANISM: Balaenoptera physalus

<400> SEQUENCE: 11

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 12
<211> LENGTH: 21
<212> TYPE: PRT
<213> ORGANISM: Balaenoptera borealis

<400> SEQUENCE: 12

Gly Ile Val Glu Gln Cys Cys Ala Ser Thr Cys Ser Leu Tyr Gln Leu
1               5                   10                  15

Glu Asn Tyr Cys Asn
            20


<210> SEQ ID NO 13
<211> LENGTH: 108
<212> TYPE: PRT
<213> ORGANISM: Sus scrofa

<400> SEQUENCE: 13

Met Ala Leu Trp Thr Arg Leu Leu Pro Leu Leu Ala Leu Leu Ala Leu
1               5                   10                  15

Trp Ala Pro Ala Pro Ala Gln Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Ala Arg Arg Glu Ala Glu Asn Pro Gln Ala Gly
    50                  55                  60

Ala Val Glu Leu Gly Gly Gly Leu Gly Gly Leu Gln Ala Leu Ala Leu
65                  70                  75                  80

Glu Gly Pro Pro Gln Lys Arg Gly Ile Val Glu Gln Cys Cys Thr Ser
                85                  90                  95

Ile Cys Ser Leu Tyr Gln Leu Glu Asn Tyr Cys Asn
            100                 105


<210> SEQ ID NO 14
<211> LENGTH: 21
<212> TYPE: PRT
<213> ORGANISM: Elephas maximus

<400> SEQUENCE: 14

Gly Ile Val Glu Gln Cys Cys Thr Gly Val Cys Ser Leu Tyr Gln Leu
1               5                   10                  15

Glu Asn Tyr Cys Asn
            20


<210> SEQ ID NO 15
```

-continued

<211> LENGTH: 105
<212> TYPE: PRT
<213> ORGANISM: Bos taurus

<400> SEQUENCE: 15

Met Ala Leu Trp Thr Arg Leu Arg Pro Leu Leu Ala Leu Leu Ala Leu
1 5 10 15

Trp Pro Pro Pro Pro Ala Arg Ala Phe Val Asn Gln His Leu Cys Gly
20 25 30

Ser His Leu Val Glu Ala Leu Tyr Leu Val Cys Gly Glu Arg Gly Phe
35 40 45

Phe Tyr Thr Pro Lys Ala Arg Arg Glu Val Glu Gly Pro Gln Val Gly
50 55 60

Ala Leu Glu Leu Ala Gly Gly Pro Gly Ala Gly Gly Leu Glu Gly Pro
65 70 75 80

Pro Gln Lys Arg Gly Ile Val Glu Gln Cys Cys Ala Ser Val Cys Ser
85 90 95

Leu Tyr Gln Leu Glu Asn Tyr Cys Asn
100 105

<210> SEQ ID NO 16
<211> LENGTH: 105
<212> TYPE: PRT
<213> ORGANISM: Ovis aries

<400> SEQUENCE: 16

Met Ala Leu Trp Thr Arg Leu Val Pro Leu Leu Ala Leu Leu Ala Leu
1 5 10 15

Trp Ala Pro Ala Pro Ala His Ala Phe Val Asn Gln His Leu Cys Gly
20 25 30

Ser His Leu Val Glu Ala Leu Tyr Leu Val Cys Gly Glu Arg Gly Phe
35 40 45

Phe Tyr Thr Pro Lys Ala Arg Arg Glu Val Glu Gly Pro Gln Val Gly
50 55 60

Ala Leu Glu Leu Ala Gly Gly Pro Gly Ala Gly Gly Leu Glu Gly Pro
65 70 75 80

Pro Gln Lys Arg Gly Ile Val Glu Gln Cys Cys Ala Gly Val Cys Ser
85 90 95

Leu Tyr Gln Leu Glu Asn Tyr Cys Asn
100 105

<210> SEQ ID NO 17
<211> LENGTH: 21
<212> TYPE: PRT
<213> ORGANISM: Camelus dromedaries

<400> SEQUENCE: 17

Gly Ile Val Glu Gln Cys Cys Ala Ser Val Cys Ser Leu Tyr Gln Leu
1 5 10 15

Glu Asn Tyr Cys Asn
20

<210> SEQ ID NO 18
<211> LENGTH: 110
<212> TYPE: PRT
<213> ORGANISM: Canis sp.

<400> SEQUENCE: 18

Met Ala Leu Trp Met Arg Leu Leu Pro Leu Leu Ala Leu Leu Ala Leu

-continued

```
1               5                   10                  15

Trp Ala Pro Ala Pro Thr Arg Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Ala Arg Arg Glu Val Glu Asp Leu Gln Val Arg
    50                  55                  60

Asp Val Glu Leu Ala Gly Ala Pro Gly Glu Gly Gly Leu Gln Pro Leu
65                  70                  75                  80

Ala Leu Glu Gly Ala Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 19
<211> LENGTH: 21
<212> TYPE: PRT
<213> ORGANISM: Hystrix cristata

<400> SEQUENCE: 19

Gly Ile Val Asp Gln Cys Cys Thr Gly Val Cys Ser Leu Tyr Gln Leu
1               5                   10                  15

Gln Asn Tyr Cys Asn
            20


<210> SEQ ID NO 20
<211> LENGTH: 108
<212> TYPE: PRT
<213> ORGANISM: Aotus trivirgatus

<400> SEQUENCE: 20

Met Ala Leu Trp Met His Leu Leu Pro Leu Leu Ala Leu Leu Ala Leu
1               5                   10                  15

Trp Gly Pro Glu Pro Ala Pro Ala Phe Val Asn Gln His Leu Cys Gly
            20                  25                  30

Pro His Leu Val Glu Ala Leu Tyr Leu Val Cys Gly Glu Arg Gly Phe
        35                  40                  45

Phe Tyr Ala Pro Lys Thr Arg Arg Glu Ala Glu Asp Leu Gln Val Gly
    50                  55                  60

Gln Val Glu Leu Gly Gly Gly Ser Ile Thr Gly Ser Leu Pro Pro Leu
65                  70                  75                  80

Glu Gly Pro Met Gln Lys Arg Gly Val Val Asp Gln Cys Cys Thr Ser
                85                  90                  95

Ile Cys Ser Leu Tyr Gln Leu Gln Asn Tyr Cys Asn
            100                 105


<210> SEQ ID NO 21
<211> LENGTH: 110
<212> TYPE: PRT
<213> ORGANISM: Macaca fasicularis

<400> SEQUENCE: 21

Met Ala Leu Trp Met Arg Leu Leu Pro Leu Leu Ala Leu Leu Ala Leu
1               5                   10                  15

Trp Gly Pro Asp Pro Ala Pro Ala Phe Val Asn Gln His Leu Cys Gly
            20                  25                  30

Ser His Leu Val Glu Ala Leu Tyr Leu Val Cys Gly Glu Arg Gly Phe
        35                  40                  45
```

-continued

```
Phe Tyr Thr Pro Lys Thr Arg Arg Glu Ala Glu Asp Pro Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 22
<211> LENGTH: 110
<212> TYPE: PRT
<213> ORGANISM: Cercopithecus aethiops

<400> SEQUENCE: 22

Met Ala Leu Trp Met Arg Leu Leu Pro Leu Leu Ala Leu Leu Ala Leu
1               5                   10                  15

Trp Gly Pro Asp Pro Val Pro Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Pro Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 23
<211> LENGTH: 110
<212> TYPE: PRT
<213> ORGANISM: Pan troglodytes

<400> SEQUENCE: 23

Met Ala Leu Trp Met Arg Leu Leu Pro Leu Leu Val Leu Leu Ala Leu
1               5                   10                  15

Trp Gly Pro Asp Pro Ala Ser Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 24
<211> LENGTH: 21
<212> TYPE: PRT
<213> ORGANISM: Ornithorhynchus anatinus

<400> SEQUENCE: 24
```

-continued

Gly Ile Val Glu Glu Cys Cys Lys Gly Val Cys Ser Met Tyr Gln Leu
1               5                   10                  15

Glu Asn Tyr Cys Asn
            20

<210> SEQ ID NO 25
<211> LENGTH: 65
<212> TYPE: PRT
<213> ORGANISM: Pongo pygmaeus

<400> SEQUENCE: 25

Cys Gly Ser His Leu Val Glu Ala Leu Tyr Leu Val Cys Gly Glu Arg
1               5                   10                  15

Gly Phe Phe Tyr Thr Pro Lys Thr Arg Arg Glu Ala Glu Asp Leu Gln
            20                  25                  30

Val Gly Gln Val Glu Leu Gly Gly Gly Pro Gly Ala Gly Ser Leu Gln
        35                  40                  45

Pro Leu Ala Leu Glu Gly Ser Leu Gln Lys Arg Gly Ile Val Glu Gln
    50                  55                  60

Cys
65

<210> SEQ ID NO 26
<211> LENGTH: 110
<212> TYPE: PRT
<213> ORGANISM: Gorilla gorilla

<400> SEQUENCE: 26

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 27
<211> LENGTH: 51
<212> TYPE: PRT
<213> ORGANISM: Saimiri sciureus

<400> SEQUENCE: 27

Phe Val Asn Gln His Leu Cys Gly Pro His Leu Val Glu Ala Leu Tyr
1               5                   10                  15

Leu Val Cys Gly Glu Arg Gly Phe Phe Tyr Ala Pro Lys Thr Gly Val
            20                  25                  30

Val Asp Gln Cys Cys Thr Ser Ile Cys Ser Leu Tyr Gln Leu Gln Asn
        35                  40                  45

Tyr Cys Asn
    50

-continued

<210> SEQ ID NO 28
<211> LENGTH: 110
<212> TYPE: PRT
<213> ORGANISM: Cricetulus longicaudatus

<400> SEQUENCE: 28

```
Met Thr Leu Trp Met Arg Leu Leu Pro Leu Leu Thr Leu Leu Val Leu
1               5                   10                  15

Trp Glu Pro Asn Pro Ala Gln Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Ser Arg Arg Gly Val Glu Asp Pro Gln Val Ala
    50                  55                  60

Gln Leu Glu Leu Gly Gly Gly Pro Gly Ala Asp Asp Leu Gln Thr Leu
65                  70                  75                  80

Ala Leu Glu Val Ala Gln Gln Lys Arg Gly Ile Val Asp Gln Cys Cys
                85                  90                  95

Thr Ser Ile Cys Ser Leu Tyr Gln Leu Glu Asn Tyr Cys Asn
            100                 105                 110
```

<210> SEQ ID NO 29
<211> LENGTH: 110
<212> TYPE: PRT
<213> ORGANISM: Rattus norvegicus

<400> SEQUENCE: 29

```
Met Ala Leu Trp Met Arg Phe Leu Pro Leu Leu Ala Leu Leu Val Leu
1               5                   10                  15

Trp Glu Pro Lys Pro Ala Gln Ala Phe Val Lys Gln His Leu Cys Gly
            20                  25                  30

Pro His Leu Val Glu Ala Leu Tyr Leu Val Cys Gly Glu Arg Gly Phe
        35                  40                  45

Phe Tyr Thr Pro Lys Ser Arg Arg Glu Val Glu Asp Pro Gln Val Pro
    50                  55                  60

Gln Leu Glu Leu Gly Gly Gly Pro Glu Ala Gly Asp Leu Gln Thr Leu
65                  70                  75                  80

Ala Leu Glu Val Ala Arg Gln Lys Arg Gly Ile Val Asp Gln Cys Cys
                85                  90                  95

Thr Ser Ile Cys Ser Leu Tyr Gln Leu Glu Asn Tyr Cys Asn
            100                 105                 110
```

<210> SEQ ID NO 30
<211> LENGTH: 110
<212> TYPE: PRT
<213> ORGANISM: Rattus norvegicus

<400> SEQUENCE: 30

```
Met Ala Leu Trp Ile Arg Phe Leu Pro Leu Leu Ala Leu Leu Ile Leu
1               5                   10                  15

Trp Glu Pro Arg Pro Ala Gln Ala Phe Val Lys Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Met Ser Arg Arg Glu Val Glu Asp Pro Gln Val Ala
    50                  55                  60

Gln Leu Glu Leu Gly Gly Gly Pro Gly Ala Gly Asp Leu Gln Thr Leu
65                  70                  75                  80
```

-continued

```
Ala Leu Glu Val Ala Arg Gln Lys Arg Gly Ile Val Asp Gln Cys Cys
                85                  90                  95

Thr Ser Ile Cys Ser Leu Tyr Gln Leu Glu Asn Tyr Cys Asn
            100                 105                 110


<210> SEQ ID NO 31
<211> LENGTH: 21
<212> TYPE: PRT
<213> ORGANISM: Acomys cahirinus

<400> SEQUENCE: 31

Gly Ile Val Asp Gln Cys Cys Thr Ser Ile Cys Ser Leu Tyr Gln Leu
1               5                   10                  15

Glu Asn Tyr Cys Asn
            20


<210> SEQ ID NO 32
<211> LENGTH: 108
<212> TYPE: PRT
<213> ORGANISM: Mus musculus

<400> SEQUENCE: 32

Met Ala Leu Leu Val His Phe Leu Pro Leu Leu Ala Leu Leu Ala Leu
1               5                   10                  15

Trp Glu Pro Lys Pro Thr Gln Ala Phe Val Lys Gln His Leu Cys Gly
            20                  25                  30

Pro His Leu Val Glu Ala Leu Tyr Leu Val Cys Gly Glu Arg Gly Phe
        35                  40                  45

Phe Tyr Thr Pro Lys Ser Arg Arg Glu Val Glu Asp Pro Gln Val Glu
    50                  55                  60

Gln Leu Glu Leu Gly Gly Ser Pro Gly Asp Leu Gln Thr Leu Ala Leu
65                  70                  75                  80

Glu Val Ala Arg Gln Lys Arg Gly Ile Val Asp Gln Cys Cys Thr Ser
                85                  90                  95

Ile Cys Ser Leu Tyr Gln Leu Glu Asn Tyr Cys Asn
            100                 105


<210> SEQ ID NO 33
<211> LENGTH: 110
<212> TYPE: PRT
<213> ORGANISM: Mus musculus

<400> SEQUENCE: 33

Met Ala Leu Trp Met Arg Phe Leu Pro Leu Leu Ala Leu Leu Phe Leu
1               5                   10                  15

Trp Glu Ser His Pro Thr Gln Ala Phe Val Lys Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Met Ser Arg Arg Glu Val Glu Asp Pro Gln Val Ala
    50                  55                  60

Gln Leu Glu Leu Gly Gly Gly Pro Gly Ala Gly Asp Leu Gln Thr Leu
65                  70                  75                  80

Ala Leu Glu Val Ala Gln Gln Lys Arg Gly Ile Val Asp Gln Cys Cys
                85                  90                  95

Thr Ser Ile Cys Ser Leu Tyr Gln Leu Glu Asn Tyr Cys Asn
            100                 105                 110
```

-continued

<210> SEQ ID NO 34
<211> LENGTH: 21
<212> TYPE: PRT
<213> ORGANISM: Chinchilla brevicaudata

<400> SEQUENCE: 34

```
Gly Ile Val Asp Gln Cys Cys Thr Ser Ile Cys Thr Leu Tyr Gln Leu
1               5                   10                  15

Glu Asn Tyr Cys Asn
            20
```

<210> SEQ ID NO 35
<211> LENGTH: 110
<212> TYPE: PRT
<213> ORGANISM: Cavia porcellus

<400> SEQUENCE: 35

```
Met Ala Leu Trp Met His Leu Leu Thr Val Leu Ala Leu Leu Ala Leu
1               5                   10                  15

Trp Gly Pro Asn Thr Gly Gln Ala Phe Val Ser Arg His Leu Cys Gly
            20                  25                  30

Ser Asn Leu Val Glu Thr Leu Tyr Ser Val Cys Gln Asp Asp Gly Phe
        35                  40                  45

Phe Tyr Ile Pro Lys Asp Arg Arg Glu Leu Glu Asp Pro Gln Val Glu
    50                  55                  60

Gln Thr Glu Leu Gly Met Gly Leu Gly Ala Gly Gly Leu Gln Pro Leu
65                  70                  75                  80

Ala Leu Glu Met Ala Leu Gln Lys Arg Gly Ile Val Asp Gln Cys Cys
                85                  90                  95

Thr Gly Thr Cys Thr Arg His Gln Leu Gln Ser Tyr Cys Asn
            100                 105                 110
```

<210> SEQ ID NO 36
<211> LENGTH: 109
<212> TYPE: PRT
<213> ORGANISM: Octodon degus

<400> SEQUENCE: 36

```
Met Ala Pro Trp Met His Leu Leu Thr Val Leu Ala Leu Leu Ala Leu
1               5                   10                  15

Trp Gly Pro Asn Ser Val Gln Ala Tyr Ser Ser Gln His Leu Cys Gly
            20                  25                  30

Ser Asn Leu Val Glu Ala Leu Tyr Met Thr Cys Gly Arg Ser Gly Phe
        35                  40                  45

Tyr Arg Pro His Asp Arg Arg Glu Leu Glu Asp Leu Gln Val Glu Gln
    50                  55                  60

Ala Glu Leu Gly Leu Glu Ala Gly Gly Leu Gln Pro Ser Ala Leu Glu
65                  70                  75                  80

Met Ile Leu Gln Lys Arg Gly Ile Val Asp Gln Cys Cys Asn Asn Ile
                85                  90                  95

Cys Thr Phe Asn Gln Leu Gln Asn Tyr Cys Asn Val Pro
            100                 105
```

<210> SEQ ID NO 37
<211> LENGTH: 21
<212> TYPE: PRT
<213> ORGANISM: Didelphis virginiana

<400> SEQUENCE: 37

-continued

```
Gly Ile Val Glu Gln Cys Cys Asn Ser Ile Cys Ser Leu Tyr Gln Leu
1               5                   10                  15

Glu Thr Tyr Cys Asn
            20


<210> SEQ ID NO 38
<211> LENGTH: 108
<212> TYPE: PRT
<213> ORGANISM: Rodentia sp.

<400> SEQUENCE: 38

Met Ala Leu Trp Ile Leu Leu Pro Leu Leu Ala Leu Leu Ile Leu Trp
1               5                   10                  15

Gly Pro Asp Pro Ala Gln Ala Phe Val Asn Gln His Leu Cys Gly Ser
            20                  25                  30

His Leu Val Glu Ala Leu Tyr Ile Leu Val Cys Gly Glu Arg Gly Phe
        35                  40                  45

Phe Tyr Thr Pro Met Ser Arg Arg Glu Val Glu Asp Pro Gln Val Gly
    50                  55                  60

Gln Val Glu Leu Gly Ala Gly Pro Gly Ala Gly Ser Glu Gln Thr Leu
65                  70                  75                  80

Ala Leu Glu Val Ala Arg Gln Ala Arg Ile Val Gln Gln Cys Thr Ser
                85                  90                  95

Gly Ile Cys Ser Leu Tyr Gln Glu Asn Tyr Cys Asn
            100                 105


<210> SEQ ID NO 39
<211> LENGTH: 110
<212> TYPE: PRT
<213> ORGANISM: Psammomys obesus

<400> SEQUENCE: 39

Met Ala Leu Trp Met Arg Leu Leu Pro Leu Leu Ala Phe Leu Ile Leu
1               5                   10                  15

Trp Glu Pro Ser Pro Ala His Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Phe Arg Arg Gly Val Asp Asp Pro Gln Met Pro
    50                  55                  60

Gln Leu Glu Leu Gly Gly Ser Pro Gly Ala Gly Asp Leu Arg Ala Leu
65                  70                  75                  80

Ala Leu Glu Val Ala Arg Gln Lys Arg Gly Ile Val Glu Gln Cys Cys
                85                  90                  95

Thr Gly Ile Cys Ser Leu Tyr Gln Leu Glu Asn Tyr Cys Asn
            100                 105                 110


<210> SEQ ID NO 40
<211> LENGTH: 110
<212> TYPE: PRT
<213> ORGANISM: Spermophilus tridecemlineatus

<400> SEQUENCE: 40

Met Ala Leu Trp Thr Arg Leu Leu Pro Leu Leu Ala Leu Leu Ala Leu
1               5                   10                  15

Leu Gly Pro Asp Pro Ala Gln Ala Phe Val Asn Gln His Leu Cys Gly
            20                  25                  30
```

-continued

```
Ser His Leu Val Glu Ala Leu Tyr Leu Val Cys Gly Glu Arg Gly Phe
        35                  40                  45

Phe Tyr Thr Pro Lys Ser Arg Arg Glu Val Glu Glu Gln Gln Gly Gly
    50                  55                  60

Gln Val Glu Leu Gly Gly Gly Pro Gly Ala Gly Leu Pro Gln Pro Leu
65                  70                  75                  80

Ala Leu Glu Met Ala Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 41
<211> LENGTH: 29
<212> TYPE: PRT
<213> ORGANISM: Cavia porcellus

<400> SEQUENCE: 41

Glu Leu Glu Asp Pro Gln Val Glu Gln Thr Glu Leu Gly Met Gly Leu
1               5                   10                  15

Gly Ala Gly Gly Leu Gln Pro Leu Gln Gly Ala Leu Gln
            20                  25


<210> SEQ ID NO 42
<211> LENGTH: 107
<212> TYPE: PRT
<213> ORGANISM: Ballus gallus

<400> SEQUENCE: 42

Met Ala Leu Trp Ile Arg Ser Leu Pro Leu Leu Ala Leu Leu Val Phe
1               5                   10                  15

Ser Gly Pro Gly Thr Ser Tyr Ala Ala Ala Asn Gln His Leu Cys Gly
            20                  25                  30

Ser His Leu Val Glu Ala Leu Tyr Leu Val Cys Gly Glu Arg Gly Phe
        35                  40                  45

Phe Tyr Ser Pro Lys Ala Arg Arg Asp Val Glu Gln Pro Leu Val Ser
    50                  55                  60

Ser Pro Leu Arg Gly Glu Ala Gly Val Leu Pro Phe Gln Gln Glu Glu
65                  70                  75                  80

Tyr Glu Lys Val Lys Arg Gly Ile Val Glu Gln Cys Cys His Asn Thr
                85                  90                  95

Cys Ser Leu Tyr Gln Leu Glu Asn Tyr Cys Asn
            100                 105


<210> SEQ ID NO 43
<211> LENGTH: 81
<212> TYPE: PRT
<213> ORGANISM: Anas platyrhynchos
<220> FEATURE:
<221> NAME/KEY: MISC_FEATURE
<222> LOCATION: (31)..(32)
<223> OTHER INFORMATION: X = any amino acid
<220> FEATURE:
<221> NAME/KEY: MISC_FEATURE
<222> LOCATION: (59)..(60)
<223> OTHER INFORMATION: X = any amino acid

<400> SEQUENCE: 43

Ala Ala Asn Gln His Leu Cys Gly Ser His Leu Val Glu Ala Leu Tyr
1               5                   10                  15

Leu Val Cys Gly Glu Arg Gly Phe Phe Tyr Ser Pro Lys Thr Xaa Xaa
            20                  25                  30
```

```
Asp Val Glu Gln Pro Leu Val Asn Gly Pro Leu His Gly Glu Val Gly
        35                  40                  45

Glu Leu Pro Phe Gln His Glu Glu Tyr Gln Xaa Xaa Gly Ile Val Glu
    50                  55                  60

Gln Cys Cys Glu Asn Pro Cys Ser Leu Tyr Gln Leu Glu Asn Tyr Cys
65                  70                  75                  80

Asn


<210> SEQ ID NO 44
<211> LENGTH: 21
<212> TYPE: PRT
<213> ORGANISM: Anser anser

<400> SEQUENCE: 44

Gly Ile Val Glu Gln Cys Cys Glu Asn Pro Cys Ser Leu Tyr Gln Leu
1               5                   10                  15

Glu Asn Tyr Cys Asn
            20


<210> SEQ ID NO 45
<211> LENGTH: 103
<212> TYPE: PRT
<213> ORGANISM: Selasphorus rufus

<400> SEQUENCE: 45

Ile Gln Ser Leu Pro Leu Leu Ala Leu Leu Ala Leu Ser Gly Pro Gly
1               5                   10                  15

Thr Ser His Ala Ala Val Asn Gln His Leu Cys Gly Ser His Leu Val
            20                  25                  30

Glu Ala Leu Tyr Leu Val Cys Gly Glu Arg Gly Phe Phe Tyr Ser Pro
        35                  40                  45

Lys Ala Arg Arg Asp Ala Glu His Pro Leu Val Asn Gly Pro Leu His
    50                  55                  60

Gly Glu Val Gly Asp Leu Pro Phe Gln Gln Glu Glu Phe Glu Lys Val
65                  70                  75                  80

Lys Arg Gly Ile Val Glu Gln Cys Cys His Asn Thr Cys Ser Leu Tyr
                85                  90                  95

Gln Leu Glu Asn Tyr Cys Asn
            100


<210> SEQ ID NO 46
<211> LENGTH: 108
<212> TYPE: PRT
<213> ORGANISM: Danio rerio

<400> SEQUENCE: 46

Met Ala Val Trp Leu Gln Ala Gly Ala Leu Leu Val Leu Leu Val Val
1               5                   10                  15

Ser Ser Val Ser Thr Asn Pro Gly Thr Pro Gln His Leu Cys Gly Ser
            20                  25                  30

His Leu Val Asp Ala Leu Tyr Leu Val Cys Gly Pro Thr Gly Phe Phe
        35                  40                  45

Tyr Asn Pro Lys Arg Asp Val Glu Pro Leu Leu Gly Phe Leu Pro Pro
    50                  55                  60

Lys Ser Ala Gln Glu Thr Glu Val Ala Asp Phe Ala Phe Lys Asp His
65                  70                  75                  80

Ala Glu Leu Ile Arg Lys Arg Gly Ile Val Glu Gln Cys Cys His Lys
```

-continued

```
                85                  90                  95

Pro Cys Ser Ile Phe Glu Leu Gln Asn Tyr Cys Asn
            100                 105


<210> SEQ ID NO 47
<211> LENGTH: 108
<212> TYPE: PRT
<213> ORGANISM: Cyprinus carpio

<400> SEQUENCE: 47

Met Ala Val Trp Ile Gln Ala Gly Ala Leu Leu Phe Leu Leu Ala Val
1               5                   10                  15

Ser Ser Val Asn Ala Asn Ala Gly Ala Pro Gln His Leu Cys Gly Ser
            20                  25                  30

His Leu Val Asp Ala Leu Tyr Leu Val Cys Gly Pro Thr Gly Phe Phe
        35                  40                  45

Tyr Asn Pro Lys Arg Asp Val Asp Pro Pro Leu Gly Phe Leu Pro Pro
    50                  55                  60

Lys Ser Ala Gln Glu Thr Glu Val Ala Asp Phe Ala Phe Lys Asp His
65                  70                  75                  80

Ala Glu Val Ile Arg Lys Arg Gly Ile Val Glu Gln Cys Cys His Lys
                85                  90                  95

Pro Cys Ser Ile Phe Glu Leu Gln Asn Tyr Cys Asn
            100                 105


<210> SEQ ID NO 48
<211> LENGTH: 21
<212> TYPE: PRT
<213> ORGANISM: Batrachoididae gen. sp.

<400> SEQUENCE: 48

Gly Ile Val Glu Gln Cys Cys His Arg Pro Cys Asp Ile Phe Asp Leu
1               5                   10                  15

Gln Ser Tyr Cys Asn
            20


<210> SEQ ID NO 49
<211> LENGTH: 21
<212> TYPE: PRT
<213> ORGANISM: Thunnus thynnus

<400> SEQUENCE: 49

Gly Ile Val Glu Gln Cys Cys His Lys Pro Cys Asn Ile Phe Asp Leu
1               5                   10                  15

Gln Asn Tyr Cys Asn
            20


<210> SEQ ID NO 50
<211> LENGTH: 21
<212> TYPE: PRT
<213> ORGANISM: Katsuwonus pelamis

<400> SEQUENCE: 50

Gly Ile His Glx Glx Cys Cys His Lys Pro Cys Asx Ile Phe Glx Leu
1               5                   10                  15

Glx Asx Tyr Cys Asn
            20


<210> SEQ ID NO 51
<211> LENGTH: 116
```

-continued

<212> TYPE: PRT
<213> ORGANISM: Lophius piscatorius

<400> SEQUENCE: 51

Met Ala Ala Leu Trp Leu Gln Ser Phe Ser Leu Leu Val Leu Leu Val
1 5 10 15

Val Ser Trp Pro Gly Ser Gln Ala Val Ala Pro Ala Gln His Leu Cys
20 25 30

Gly Ser His Leu Val Asp Ala Leu Tyr Leu Val Cys Gly Asp Arg Gly
35 40 45

Phe Phe Tyr Asn Pro Lys Arg Asp Val Asp Gln Leu Leu Gly Phe Leu
50 55 60

Pro Pro Lys Ser Gly Gly Ala Ala Ala Ala Gly Ala Asp Asn Glu Val
65 70 75 80

Ala Glu Phe Ala Phe Lys Asp Gln Met Glu Met Met Val Lys Arg Gly
85 90 95

Ile Val Glu Gln Cys Cys His Arg Pro Cys Asn Ile Phe Asp Leu Gln
100 105 110

Asn Tyr Cys Asn
115

<210> SEQ ID NO 52
<211> LENGTH: 115
<212> TYPE: PRT
<213> ORGANISM: Myxine glutinosa

<400> SEQUENCE: 52

Met Ala Leu Ser Pro Phe Leu Ala Ala Val Ile Pro Leu Val Leu Leu
1 5 10 15

Leu Ser Arg Ala Pro Pro Ser Ala Asp Thr Arg Thr Thr Gly His Leu
20 25 30

Cys Gly Lys Asp Leu Val Asn Ala Leu Tyr Ile Ala Cys Gly Val Arg
35 40 45

Gly Phe Phe Tyr Asp Pro Thr Lys Met Lys Arg Asp Thr Gly Ala Leu
50 55 60

Ala Ala Phe Leu Pro Leu Ala Tyr Ala Glu Asp Asn Glu Ser Gln Asp
65 70 75 80

Asp Glu Ser Ile Gly Ile Asn Glu Val Leu Lys Ser Lys Arg Gly Ile
85 90 95

Val Glu Gln Cys Cys His Lys Arg Cys Ser Ile Tyr Asp Leu Glu Asn
100 105 110

Tyr Cys Asn
115

<210> SEQ ID NO 53
<211> LENGTH: 105
<212> TYPE: PRT
<213> ORGANISM: Oncorhynchus keta

<400> SEQUENCE: 53

Met Ala Phe Trp Leu Gln Ala Ala Ser Leu Leu Val Leu Leu Ala Leu
1 5 10 15

Ser Pro Gly Val Asp Ala Ala Ala Ala Gln His Leu Cys Gly Ser His
20 25 30

Leu Val Asp Ala Leu Tyr Leu Val Cys Gly Glu Lys Gly Phe Phe Tyr
35 40 45

Thr Pro Lys Arg Asp Val Asp Pro Leu Ile Gly Phe Leu Ser Pro Lys

-continued

```
    50                  55                  60

Ser Ala Lys Glu Asn Glu Glu Tyr Pro Phe Lys Asp Gln Thr Glu Met
65                  70                  75                  80

Met Val Lys Arg Gly Ile Val Glu Gln Cys Cys His Lys Pro Cys Asn
                85                  90                  95

Ile Phe Asp Leu Gln Asn Tyr Cys Asn
            100                 105


<210> SEQ ID NO 54
<211> LENGTH: 21
<212> TYPE: PRT
<213> ORGANISM: Myoxocephalus scorpius

<400> SEQUENCE: 54

Gly Ile Val Glu Gln Cys Cys His Arg Pro Cys Asn Ile Arg Val Leu
1               5                   10                  15

Glu Asn Tyr Cys Asn
            20


<210> SEQ ID NO 55
<211> LENGTH: 21
<212> TYPE: PRT
<213> ORGANISM: Lepisosteus spatula

<400> SEQUENCE: 55

Gly Ile Val Glu Gln Cys Cys His Lys Pro Cys Thr Ile Tyr Glu Leu
1               5                   10                  15

Glu Asn Tyr Cys Asn
            20


<210> SEQ ID NO 56
<211> LENGTH: 21
<212> TYPE: PRT
<213> ORGANISM: Platichthys flesus

<400> SEQUENCE: 56

Gly Ile Val Glu Gln Cys Cys His Lys Pro Cys Asn Ile Phe Asp Leu
1               5                   10                  15

Gln Asn Tyr Cys Asn
            20


<210> SEQ ID NO 57
<211> LENGTH: 21
<212> TYPE: PRT
<213> ORGANISM: Hydrolagus colliei

<400> SEQUENCE: 57

Gly Ile Val Glu Gln Cys Cys His Asn Thr Cys Ser Leu Ala Asn Leu
1               5                   10                  15

Glu Gly Tyr Cys Asn
            20


<210> SEQ ID NO 58
<211> LENGTH: 22
<212> TYPE: PRT
<213> ORGANISM: Squalus acanthias

<400> SEQUENCE: 58

Gly Ile Val Glu His Cys Cys His Asn Thr Cys Ser Leu Tyr Asp Leu
1               5                   10                  15

Glu Gly Tyr Cys Asn Gln
```

-continued

```
            20


<210> SEQ ID NO 59
<211> LENGTH: 21
<212> TYPE: PRT
<213> ORGANISM: Torpedo marmorata

<400> SEQUENCE: 59

Gly Ile Val Glu His Cys Cys His Asn Thr Cys Ser Leu Phe Asp Leu
1               5                   10                  15

Glu Gly Tyr Cys Asn
            20


<210> SEQ ID NO 60
<211> LENGTH: 89
<212> TYPE: PRT
<213> ORGANISM: Callorhinchus milii

<400> SEQUENCE: 60

Val Pro Thr Gln Arg Leu Cys Gly Ser His Leu Val Asp Ala Leu Tyr
1               5                   10                  15

Phe Val Cys Gly Glu Arg Gly Phe Phe Tyr Ser Pro Lys Gln Ile Arg
            20                  25                  30

Asp Val Gly Pro Leu Ser Ala Phe Arg Asp Leu Glu Pro Pro Leu Asp
        35                  40                  45

Thr Glu Met Glu Asp Arg Phe Pro Tyr Arg Gln Gln Leu Ala Gly Ser
    50                  55                  60

Lys Met Lys Arg Gly Ile Val Glu Gln Cys Cys His Asn Thr Cys Ser
65                  70                  75                  80

Leu Val Asn Leu Glu Gly Tyr Cys Asn
                85


<210> SEQ ID NO 61
<211> LENGTH: 21
<212> TYPE: PRT
<213> ORGANISM: Petromyzon marinus

<400> SEQUENCE: 61

Gly Ile Val Glu Gln Cys Cys His Arg Lys Cys Ser Ile Tyr Asp Met
1               5                   10                  15

Glu Asn Tyr Cys Asn
            20


<210> SEQ ID NO 62
<211> LENGTH: 21
<212> TYPE: PRT
<213> ORGANISM: Oncorhynchus gorbuscha

<400> SEQUENCE: 62

Gly Ile Val Glu Gln Cys Cys His Lys Pro Cys Asn Ile Phe Asp Leu
1               5                   10                  15

Gln Asn Tyr Cys Asn
            20


<210> SEQ ID NO 63
<211> LENGTH: 21
<212> TYPE: PRT
<213> ORGANISM: Amia calva

<400> SEQUENCE: 63

Gly Ile Val Glu Gln Cys Cys Leu Lys Pro Cys Thr Ile Tyr Glu Met
```

-continued

```
1               5                   10                  15

Glu Lys Tyr Cys Asn
            20


<210> SEQ ID NO 64
<211> LENGTH: 21
<212> TYPE: PRT
<213> ORGANISM: Anguilla rostrata

<400> SEQUENCE: 64

Gly Ile Val Glu Gln Cys Cys His Lys Pro Cys Ser Ile Phe Asp Leu
1               5                   10                  15

Gln Asn Tyr Cys Asn
            20


<210> SEQ ID NO 65
<211> LENGTH: 113
<212> TYPE: PRT
<213> ORGANISM: Oreochromis niloticus

<400> SEQUENCE: 65

Met Ala Ala Leu Trp Leu Gln Ala Phe Ser Leu Leu Val Leu Met Met
1               5                   10                  15

Val Ser Trp Pro Gly Ser Gln Ala Val Gly Gly Pro Gln His Leu Cys
            20                  25                  30

Gly Ser His Leu Val Asp Ala Leu Tyr Leu Val Cys Gly Asp Arg Gly
        35                  40                  45

Phe Phe Tyr Asn Pro Arg Arg Asp Val Asp Pro Leu Leu Gly Phe Leu
    50                  55                  60

Pro Pro Lys Ala Gly Gly Ala Val Val Gln Gly Gly Glu Asn Glu Val
65                  70                  75                  80

Thr Phe Lys Asp Gln Met Glu Met Met Val Lys Arg Gly Ile Val Glu
                85                  90                  95

Glu Cys Cys His Lys Pro Cys Thr Ile Phe Asp Leu Gln Asn Tyr Cys
            100                 105                 110

Asn


<210> SEQ ID NO 66
<211> LENGTH: 21
<212> TYPE: PRT
<213> ORGANISM: Acipenser gueldenstaedti

<400> SEQUENCE: 66

Gly Ile Val Glu Gln Cys Cys His Ser Pro Cys Ser Leu Tyr Asp Leu
1               5                   10                  15

Glu Asn Tyr Cys Asn
            20


<210> SEQ ID NO 67
<211> LENGTH: 21
<212> TYPE: PRT
<213> ORGANISM: Piaractus mesopotamicus

<400> SEQUENCE: 67

Gly Ile Val Glu Gln Cys Cys His Lys Pro Cys Ser Ile Phe Asp Leu
1               5                   10                  15

Gln Asn Tyr Cys Asn
            20
```

-continued

<210> SEQ ID NO 68
<211> LENGTH: 115
<212> TYPE: PRT
<213> ORGANISM: Verasper moseri

<400> SEQUENCE: 68

```
Met Ala Ala Leu Trp Leu Gln Ser Val Ser Leu Leu Val Leu Met Leu
1               5                   10                  15

Val Ser Trp Ser Gly Ser Gln Ala Val Leu Pro Pro Gln His Leu Cys
            20                  25                  30

Gly Ala His Leu Val Asp Ala Leu Tyr Leu Val Cys Gly Glu Arg Gly
        35                  40                  45

Phe Phe Tyr Thr Pro Lys Arg Asp Val Asp Pro Leu Leu Gly Phe Leu
    50                  55                  60

Pro Ala Lys Ser Gly Gly Ala Ala Ala Gly Gly Glu Asn Glu Val Ala
65                  70                  75                  80

Glu Phe Ala Phe Lys Asp Gln Met Glu Met Met Val Lys Arg Gly Ile
                85                  90                  95

Val Glu Gln Cys Cys His Lys Pro Cys Asn Ile Phe Asp Leu Gln Asn
            100                 105                 110

Tyr Cys Asn
        115
```

<210> SEQ ID NO 69
<211> LENGTH: 30
<212> TYPE: PRT
<213> ORGANISM: Anquilla anguilla

<400> SEQUENCE: 69

```
Asp Val Glu Pro Leu Leu Gly Phe Leu Ser Pro Lys Ser Gly Gln Glu
1               5                   10                  15

Asn Glu Val Asp Asp Phe Pro Tyr Lys Gly Gln Gly Glu Leu
            20                  25                  30
```

<210> SEQ ID NO 70
<211> LENGTH: 106
<212> TYPE: PRT
<213> ORGANISM: Xenopus laevis

<400> SEQUENCE: 70

```
Met Ala Leu Trp Met Gln Cys Leu Pro Leu Val Leu Val Leu Phe Phe
1               5                   10                  15

Ser Thr Pro Asn Thr Glu Ala Leu Val Asn Gln His Leu Cys Gly Ser
            20                  25                  30

His Leu Val Glu Ala Leu Tyr Leu Val Cys Gly Asp Arg Gly Phe Phe
        35                  40                  45

Tyr Tyr Pro Lys Val Lys Arg Asp Met Glu Gln Ala Leu Val Ser Gly
    50                  55                  60

Pro Gln Asp Asn Glu Leu Asp Gly Met Gln Leu Gln Pro Gln Glu Tyr
65                  70                  75                  80

Gln Lys Met Lys Arg Gly Ile Val Glu Gln Cys Cys His Ser Thr Cys
                85                  90                  95

Ser Leu Phe Gln Leu Glu Ser Tyr Cys Asn
            100                 105
```

<210> SEQ ID NO 71
<211> LENGTH: 106
<212> TYPE: PRT
<213> ORGANISM: Xenopus laevis -continued

<400> SEQUENCE: 71

```
Met Ala Leu Trp Met Gln Cys Leu Pro Leu Val Leu Val Leu Leu Phe
1               5                   10                  15

Ser Thr Pro Asn Thr Glu Ala Leu Ala Asn Gln His Leu Cys Gly Ser
            20                  25                  30

His Leu Val Glu Ala Leu Tyr Leu Val Cys Gly Asp Arg Gly Phe Phe
        35                  40                  45

Tyr Tyr Pro Lys Ile Lys Arg Asp Ile Glu Gln Ala Gln Val Asn Gly
    50                  55                  60

Pro Gln Asp Asn Glu Leu Asp Gly Met Gln Phe Gln Pro Gln Glu Tyr
65                  70                  75                  80

Gln Lys Met Lys Arg Gly Ile Val Glu Gln Cys Cys His Ser Thr Cys
                85                  90                  95

Ser Leu Phe Gln Leu Glu Asn Tyr Cys Asn
            100                 105
```

<210> SEQ ID NO 72
<211> LENGTH: 21
<212> TYPE: PRT
<213> ORGANISM: Trachemys scripta

<400> SEQUENCE: 72

```
Gly Ile Val Glu Gln Cys Cys His Asn Thr Cys Ser Leu Tyr Gln Leu
1               5                   10                  15

Glu Asn Tyr Cys Asn
            20
```

<210> SEQ ID NO 73
<211> LENGTH: 21
<212> TYPE: PRT
<213> ORGANISM: Alligator mississippiensis

<400> SEQUENCE: 73

```
Gly Ile Val Glu Gln Cys Cys His Asn Thr Cys Ser Leu Tyr Gln Leu
1               5                   10                  15

Glu Asn Tyr Cys Asn
            20
```

<210> SEQ ID NO 74
<211> LENGTH: 21
<212> TYPE: PRT
<213> ORGANISM: Zaocys dhumnades

<400> SEQUENCE: 74

```
Gly Ile Val Glu Gln Cys Cys Glu Asn Thr Cys Ser Leu Tyr Glu Leu
1               5                   10                  15

Glu Asn Tyr Cys Asn
            20
```

<210> SEQ ID NO 75
<211> LENGTH: 21
<212> TYPE: PRT
<213> ORGANISM: Crotalus atrox

<400> SEQUENCE: 75

```
Gly Ile Val Glu Gln Cys Cys Glu Asn Thr Cys Ser Leu Tyr Gln Leu
1               5                   10                  15

Glu Asn Tyr Cys Asn
            20
```

-continued

<210> SEQ ID NO 76
<211> LENGTH: 114
<212> TYPE: PRT
<213> ORGANISM: Artificial Sequence
<220> FEATURE:
<223> OTHER INFORMATION: Preproinsulin

<400> SEQUENCE: 76

```
Met Gly Leu Trp Ile Arg Leu Leu Pro Leu Ile Ala Leu Leu Ile Leu
1               5                   10                  15

Trp Gly Pro Asp Pro Ala Ala Ala Glu Phe Arg Met Phe Val Asn Gln
            20                  25                  30

His Leu Cys Gly Ser His Leu Val Glu Ala Leu Tyr Leu Val Cys Gly
        35                  40                  45

Glu Arg Gly Phe Phe Tyr Thr Pro Lys Thr Arg Arg Glu Ala Glu Asp
    50                  55                  60

Leu Gln Val Gly Gln Val Glu Leu Gly Gly Gly Pro Gly Ala Gly Ser
65                  70                  75                  80

Leu Gln Pro Leu Ala Leu Glu Gly Ser Leu Gln Lys Arg Gly Ile Val
                85                  90                  95

Glu Gln Cys Cys Thr Ser Ile Cys Ser Leu Tyr Gln Leu Glu Asn Tyr
            100                 105                 110

Cys Asn
```

<210> SEQ ID NO 77
<211> LENGTH: 21
<212> TYPE: PRT
<213> ORGANISM: Artificial Sequence
<220> FEATURE:
<223> OTHER INFORMATION: Insulin

<400> SEQUENCE: 77

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 78
<211> LENGTH: 30
<212> TYPE: PRT
<213> ORGANISM: Artificial Sequence
<220> FEATURE:
<223> OTHER INFORMATION: Insulin

<400> SEQUENCE: 78

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 79
<211> LENGTH: 53
<212> TYPE: PRT
<213> ORGANISM: Artificial Sequence
<220> FEATURE:
<223> OTHER INFORMATION: Insulin

<400> SEQUENCE: 79

```
Phe Val Asp Gln His Leu Cys Gly Ser His Leu Val Glu Ala Leu Tyr
1               5                   10                  15
```

-continued

```
Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Glu Leu
        35                  40                  45

Glu Asp Tyr Cys Asn
    50


<210> SEQ ID NO 80
<211> LENGTH: 53
<212> TYPE: PRT
<213> ORGANISM: Artificial Sequence
<220> FEATURE:
<223> OTHER INFORMATION: Insulin

<400> SEQUENCE: 80

Phe Val Glu Gln His Leu Cys Gly Ser Asp Leu Val Glu Ala Leu Tyr
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Glu Tyr Cys Asn
    50


<210> SEQ ID NO 81
<211> LENGTH: 53
<212> TYPE: PRT
<213> ORGANISM: Artificial Sequence
<220> FEATURE:
<223> OTHER INFORMATION: Insulin

<400> SEQUENCE: 81

Phe Val Gln Gln His Leu Cys Gly Ser His Leu Val Glu Ala Leu Tyr
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Gly
    50


<210> SEQ ID NO 82
<211> LENGTH: 53
<212> TYPE: PRT
<213> ORGANISM: Artificial Sequence
<220> FEATURE:
<223> OTHER INFORMATION: Unnamed protein product with insulin homology

<400> SEQUENCE: 82

Phe Val Thr Gln His Leu Cys Gly Ser His Leu Val Glu Ala Leu Tyr
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu His Tyr Cys Ser
    50


<210> SEQ ID NO 83
<211> LENGTH: 57
<212> TYPE: PRT
```

-continued

<213> ORGANISM: Artificial Sequence
<220> FEATURE:
<223> OTHER INFORMATION: Proinsulin

<400> SEQUENCE: 83

```
Asn Ser Asn Gly Lys Phe Val Asn Gln His Leu Cys Gly Ser His Leu
1               5                   10                  15

Val Glu Ala Leu Tyr Leu Val Cys Gly Glu Arg Gly Phe Phe Tyr Thr
            20                  25                  30

Pro Lys Thr Lys Gly Ile Val Glu Gln Cys Cys Thr Ser Ile Cys Ser
        35                  40                  45

Leu Tyr Gln Leu Glu Asn Tyr Cys Asn
    50                  55
```

<210> SEQ ID NO 84
<211> LENGTH: 58
<212> TYPE: PRT
<213> ORGANISM: Artificial Sequence
<220> FEATURE:
<223> OTHER INFORMATION: Insulin

<400> SEQUENCE: 84

```
Asn Ser Asn Gly Lys Phe Val Asn Gln His Leu Cys Gly Ser His Leu
1               5                   10                  15

Val Glu Ala Leu Tyr Leu Val Cys Gly Glu Arg Gly Phe Phe Tyr Thr
            20                  25                  30

Pro Lys Thr Lys Arg Gly Ile Val Glu Gln Cys Cys Thr Ser Ile Cys
        35                  40                  45

Ser Leu Tyr Gln Leu Glu Asn Tyr Cys Asn
    50                  55
```

<210> SEQ ID NO 85
<211> LENGTH: 50
<212> TYPE: PRT
<213> ORGANISM: Artificial Sequence
<220> FEATURE:
<223> OTHER INFORMATION: Insulin

<400> SEQUENCE: 85

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Gly Ile Val
            20                  25                  30

Glu Gln Cys Cys Thr Ser Ile Cys Ser Leu Tyr Gln Leu Glu Asn Tyr
        35                  40                  45

Cys Asn
    50
```

<210> SEQ ID NO 86
<211> LENGTH: 54
<212> TYPE: PRT
<213> ORGANISM: Artificial Sequence
<220> FEATURE:
<223> OTHER INFORMATION: Insulin

<400> SEQUENCE: 86

```
Arg Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Ala Ala
            20                  25                  30

Lys Gly Ile Val Glu Gln Cys Cys Thr Ser Ile Cys Ser Leu Tyr Gln
```

-continued 35 40 45

Leu Glu Asn Tyr Cys Asn
50

<210> SEQ ID NO 87
<211> LENGTH: 61
<212> TYPE: PRT
<213> ORGANISM: Artificial Sequence
<220> FEATURE:
<223> OTHER INFORMATION: Insulin

<400> SEQUENCE: 87

Lys Glu Thr Leu Thr Ile Thr Cys Ala Val Pro Thr Trp Leu Lys Leu
1 5 10 15

Trp Thr Trp Phe Ala Val Lys Glu Val Ser Ser Thr Asn Leu Arg Leu
20 25 30

Leu Arg Val Leu Ser Asn Asn Ala Val Pro Pro Ser Ala Pro Cys Thr
35 40 45

Asn Trp Lys Thr Thr Ala Thr Arg Arg Ser Pro Gln Ala
50 55 60

<210> SEQ ID NO 88
<211> LENGTH: 61
<212> TYPE: PRT
<213> ORGANISM: Artificial Sequence
<220> FEATURE:
<223> OTHER INFORMATION: Preproinsulin

<400> SEQUENCE: 88

Lys Asp Ser Leu Thr Asn Thr Cys Ala Val Ser Thr Trp Leu Lys Leu
1 5 10 15

Cys Thr Trp Phe Ala Val Lys Glu Val Ser Ser Thr Leu Leu Arg Leu
20 25 30

Leu Arg Val Leu Ser Asn Asn Ala Val Pro Pro Ser Ala Asn Tyr Thr
35 40 45

Asn Trp Lys Thr Thr Ala Thr Arg Arg Ser Pro Gln Ala
50 55 60

<210> SEQ ID NO 89
<211> LENGTH: 87
<212> TYPE: PRT
<213> ORGANISM: Artificial Sequence
<220> FEATURE:
<223> OTHER INFORMATION: Proinsulin

<400> SEQUENCE: 89

Met Phe Val Asn Gln His Leu Cys Gly Ser His Leu Val Glu Ala Leu
1 5 10 15

Tyr Leu Val Cys Gly Glu Arg Gly Phe Phe Tyr Thr Pro Lys Thr Arg
20 25 30

Arg Glu Ala Glu Asp Leu Gln Val Gly Gln Val Glu Leu Gly Gly Gly
35 40 45

Pro Gly Ala Gly Ser Leu Gln Pro Leu Ala Leu Glu Gly Ser Leu Gln
50 55 60

Lys Arg Gly Ile Val Glu Gln Cys Cys Thr Ser Ile Cys Ser Leu Tyr
65 70 75 80

Gln Leu Glu Asn Tyr Cys Asn
85

<210> SEQ ID NO 90

-continued

<211> LENGTH: 35
<212> TYPE: PRT
<213> ORGANISM: Artificial Sequence
<220> FEATURE:
<223> OTHER INFORMATION: Insulin

<400> SEQUENCE: 90

```
Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35
```

<210> SEQ ID NO 91
<211> LENGTH: 23
<212> TYPE: PRT
<213> ORGANISM: Artificial Sequence
<220> FEATURE:
<223> OTHER INFORMATION: Insulin

<400> SEQUENCE: 91

```
Gly Pro Glu Thr Leu Cys Gly Ala Glu Leu Val Asp Ala Leu Gln Phe
1               5                   10                  15

Val Cys Gly Asp Arg Gly Phe
            20
```

<210> SEQ ID NO 92
<211> LENGTH: 124
<212> TYPE: PRT
<213> ORGANISM: Artificial Sequence
<220> FEATURE:
<223> OTHER INFORMATION: Insulin

<400> SEQUENCE: 92

```
Met Lys Leu Lys Thr Val Arg Ser Ala Val Leu Ser Ser Leu Phe Ala
1               5                   10                  15

Ser Gln Val Leu Gly Gln Pro Ile Asp Asp Thr Glu Ser Gln Thr Thr
            20                  25                  30

Ser Val Asn Leu Met Ala Asp Asp Thr Glu Ser Ala Phe Ala Thr Gln
        35                  40                  45

Thr Asn Ser Gly Gly Leu Asp Val Val Gly Leu Ile Ser Met Ala Lys
    50                  55                  60

Arg Glu Glu Gly Glu Pro Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Ala Ala Lys Gly Ile Val Glu Gln Cys Cys Thr Ser
            100                 105                 110

Ile Cys Ser Leu Tyr Gln Leu Glu Asn Tyr Cys Asn
        115                 120
```

<210> SEQ ID NO 93
<211> LENGTH: 171
<212> TYPE: DNA
<213> ORGANISM: Artificial Sequence
<220> FEATURE:
<223> OTHER INFORMATION: Insulin

<400> SEQUENCE: 93

```
tttgtcaatc agcacctttg tggttctcac ctggtggagg ctctgtacct ggtgtgtggg     60
```

-continued gaacgtggtt tcttctacac acccaagacc cgtcgtaagc ttaagcgtgg cattgtggag 120
cagtgctgca ccagcatctg ctccctctac caactggaga actactgcaa c 171

<210> SEQ ID NO 94
<211> LENGTH: 21
<212> TYPE: PRT
<213> ORGANISM: Artificial Sequence
<220> FEATURE:
<223> OTHER INFORMATION: Insulin analogue

<400> SEQUENCE: 94

Gly Ile Val Glu Gln Cys Cys Thr Ser Ile Cys Ser Leu Tyr Gln Leu
1 5 10 15

Glu Asn Tyr Cys Asn
20

<210> SEQ ID NO 95
<211> LENGTH: 26
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (26)..(26)
<223> OTHER INFORMATION: X = any amino acid

<400> SEQUENCE: 95

Phe Val Asn Gln His Leu Cys Gly Ser His Leu Val Glu Ala Leu Tyr
1 5 10 15

Leu Val Cys Gly Glu Arg Gly Phe Phe Xaa
20 25

<210> SEQ ID NO 96
<211> LENGTH: 21
<212> TYPE: PRT
<213> ORGANISM: Homo sapiens

<400> SEQUENCE: 96

Gly Ile Val Glu Gln Cys Cys Thr Ser Ile Cys Ser Leu Tyr Gln Leu
1 5 10 15

Glu Asn Tyr Cys Asn
20

<210> SEQ ID NO 97
<211> LENGTH: 29
<212> TYPE: PRT
<213> ORGANISM: Homo sapiens

<400> SEQUENCE: 97

Glu Val Asn Gln His Leu Cys Gly Ser Glu Leu Val Glu Ala Leu Glu
1 5 10 15

Leu Val Cys Gly Glu Arg Gly Phe Phe Tyr Glu Pro Lys
20 25

<210> SEQ ID NO 98
<211> LENGTH: 21
<212> TYPE: PRT
<213> ORGANISM: Homo sapiens

<400> SEQUENCE: 98

Gly Ile Val Glu Gln Cys Cys Thr Ser Ile Cys Ser Leu Tyr Gln Leu
1 5 10 15

-continued

```
Glu Asn Tyr Cys Asn
            20


<210> SEQ ID NO 99
<211> LENGTH: 30
<212> TYPE: PRT
<213> ORGANISM: Homo sapiens

<400> SEQUENCE: 99

Phe Val Asn Gln His Leu Cys Gly Ser His Leu Val Glu Ala Leu His
1               5                   10                  15

Leu Val Cys Gly Glu Arg Gly Phe Phe Tyr Thr Pro Lys Thr
            20                  25                  30


<210> SEQ ID NO 100
<211> LENGTH: 21
<212> TYPE: PRT
<213> ORGANISM: Homo sapiens

<400> SEQUENCE: 100

Gly Ile Val Glu Gln Cys Cys Lys Ser Ile Cys Ser Leu Tyr Gln Leu
1               5                   10                  15

Glu Asn Tyr Cys Asn
            20


<210> SEQ ID NO 101
<211> LENGTH: 30
<212> TYPE: PRT
<213> ORGANISM: Homo sapiens

<400> SEQUENCE: 101

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 102
<211> LENGTH: 21
<212> TYPE: PRT
<213> ORGANISM: Homo sapiens

<400> SEQUENCE: 102

Gly Ile Val Glu Gln Cys Cys Lys Ser Ile Cys Ser Leu Tyr Gln Leu
1               5                   10                  15

Glu Asn Tyr Cys Asn
            20


<210> SEQ ID NO 103
<211> LENGTH: 30
<212> TYPE: PRT
<213> ORGANISM: Homo sapiens

<400> SEQUENCE: 103

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 104
<211> LENGTH: 21
<212> TYPE: PRT
<213> ORGANISM: Homo sapiens
<220> FEATURE:
```

-continued

<221> NAME/KEY: MISC_FEATURE
<222> LOCATION: (8)..(8)
<223> OTHER INFORMATION: X = any amino acid

<400> SEQUENCE: 104

```
Gly Ile Val Glu Gln Cys Cys Xaa Ser Ile Cys Ser Leu Tyr Gln Leu
1               5                   10                  15

Glu Asn Tyr Cys Asn
            20
```

<210> SEQ ID NO 105
<211> LENGTH: 30
<212> TYPE: PRT
<213> ORGANISM: Homo sapiens

<400> SEQUENCE: 105

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 106
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X = any amino acid

<400> SEQUENCE: 106

```
Gly Ile Val Glu Gln Cys Cys Xaa Ser Ile Cys Ser Leu Tyr Gln Leu
1               5                   10                  15

Glu Asn Tyr Cys Asn
            20
```

<210> SEQ ID NO 107
<211> LENGTH: 30
<212> TYPE: PRT
<213> ORGANISM: Homo sapiens

<400> SEQUENCE: 107

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 108
<211> LENGTH: 21
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X = any amino acids

<400> SEQUENCE: 108

```
Gly Xaa Val Glu Gln Cys Cys Thr Ser Ile Cys Ser Leu Tyr Gln Leu
1               5                   10                  15

Glu Asn Tyr Cys Asn
            20
```

<210> SEQ ID NO 109
<211> LENGTH: 30

-continued

<212> TYPE: PRT
<213> ORGANISM: Homo sapiens

<400> SEQUENCE: 109

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 110
<211> LENGTH: 21
<212> TYPE: PRT
<213> ORGANISM: Homo sapiens

<400> SEQUENCE: 110

Gly Ala Val Glu Gln Cys Cys Thr Ser Ile Cys Ser Leu Tyr Gln Leu
1               5                   10                  15

Glu Asn Tyr Cys Asn
            20

<210> SEQ ID NO 111
<211> LENGTH: 30
<212> TYPE: PRT
<213> ORGANISM: Homo sapiens

<400> SEQUENCE: 111

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 112
<211> LENGTH: 21
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (2)..(2)
<223> OTHER INFORMATION: X = any amino acid

<400> SEQUENCE: 112

Gly Xaa Val Glu Gln Cys Cys Thr Ser Ile Cys Ser Leu Tyr Gln Leu
1               5                   10                  15

Glu Asn Tyr Cys Asn
            20

<210> SEQ ID NO 113
<211> LENGTH: 30
<212> TYPE: PRT
<213> ORGANISM: Artificial Sequence
<220> FEATURE:
<223> OTHER INFORMATION: Insulin analogue

<400> SEQUENCE: 113

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 114
<211> LENGTH: 21
<212> TYPE: PRT

-continued

<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (2)..(2)
<223> OTHER INFORMATION: X = any amino acid

<400> SEQUENCE: 114

```
Gly Xaa Val Glu Gln Cys Cys Thr Ser Ile Cys Ser Leu Tyr Gln Leu
1               5                   10                  15

Glu Asn Tyr Cys Asn
            20
```

<210> SEQ ID NO 115
<211> LENGTH: 30
<212> TYPE: PRT
<213> ORGANISM: Artificial Sequence
<220> FEATURE:
<223> OTHER INFORMATION: Insulin analogue

<400> SEQUENCE: 115

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 116
<211> LENGTH: 21
<212> TYPE: PRT
<213> ORGANISM: Homo sapiens

<400> SEQUENCE: 116

```
Gly Gly Gly Glu Gln Cys Cys Thr Ser Ile Cys Ser Leu Tyr Gln Leu
1               5                   10                  15

Glu Asn Tyr Cys Asn
            20
```

<210> SEQ ID NO 117
<211> LENGTH: 30
<212> TYPE: PRT
<213> ORGANISM: Homo sapiens

<400> SEQUENCE: 117

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 118
<211> LENGTH: 21
<212> TYPE: PRT
<213> ORGANISM: Artificial Sequence
<220> FEATURE:
<223> OTHER INFORMATION: Homo sapiens insulin mutant
<220> FEATURE:
<221> NAME/KEY: MISC_FEATURE
<222> LOCATION: (1)..(1)
<223> OTHER INFORMATION: X = any amino acid

<400> SEQUENCE: 118

```
Xaa Ile Val Glu Gln Cys Cys Thr Ser Ile Cys Ser Leu Tyr Gln Leu
1               5                   10                  15

Glu Asn Tyr Cys Asn
            20
```

-continued

<210> SEQ ID NO 119
<211> LENGTH: 30
<212> TYPE: PRT
<213> ORGANISM: Artificial Sequence
<220> FEATURE:
<223> OTHER INFORMATION: Homo sapiens insulin mutant
<220> FEATURE:
<221> NAME/KEY: MISC_FEATURE
<222> LOCATION: (1)..(1)
<223> OTHER INFORMATION: X = any amino acid

<400> SEQUENCE: 119

```
Xaa Val Asn Gln His Leu Cys Gly Asp His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 120
<211> LENGTH: 21
<212> TYPE: PRT
<213> ORGANISM: Artificial Sequence
<220> FEATURE:
<223> OTHER INFORMATION: Homo sapiens insulin mutant

<400> SEQUENCE: 120

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 121
<211> LENGTH: 29
<212> TYPE: PRT
<213> ORGANISM: Artificial Sequence
<220> FEATURE:
<223> OTHER INFORMATION: Homo sapiens insulin mutant

<400> SEQUENCE: 121

```
Phe Val Asn Gln His Leu Cys Gly Ser His Leu Val Glu Ala Leu Tyr
1               5                   10                  15

Leu Val Cys Gly Glu Arg Gly Phe Tyr Thr Pro Lys Thr
            20                  25
```

<210> SEQ ID NO 122
<211> LENGTH: 21
<212> TYPE: PRT
<213> ORGANISM: Artificial Sequence
<220> FEATURE:
<223> OTHER INFORMATION: Homo sapiens insulin

<400> SEQUENCE: 122

```
Gly Ile Val Glu Gln Ser Cys Thr Ser Ile Ser Ser Leu Tyr Gln Leu
1               5                   10                  15

Glu Asn Tyr Cys Asn
            20
```

<210> SEQ ID NO 123
<211> LENGTH: 30
<212> TYPE: PRT
<213> ORGANISM: Artificial Sequence
<220> FEATURE:
<223> OTHER INFORMATION: Homo sapiens insulin

<400> SEQUENCE: 123

-continued

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30


<210> SEQ ID NO 124
<211> LENGTH: 79
<212> TYPE: PRT
<213> ORGANISM: Artificial Sequence
<220> FEATURE:
<223> OTHER INFORMATION: Insulin

<400> SEQUENCE: 124

Met Asp Pro Gly Asp Pro Glu Cys Leu Glu Gln Leu Leu Arg Arg Leu
1               5                   10                  15

Gly Gly Ser Val Glu Val Glu Val Thr Gly Gly Thr Val His Val Glu
            20                  25                  30

Val Ser Pro Glu Asp Pro Gly Asp Pro Glu Cys Leu Glu Gln Leu Leu
        35                  40                  45

Arg Arg Leu Gly Gly Ser Val Glu Val Glu Val Thr Gly Gly Thr Val
    50                  55                  60

His Val Glu Val Ser Pro Gly Glu Arg Gly Phe Phe Tyr Cys Asn
65                  70                  75


<210> SEQ ID NO 125
<211> LENGTH: 87
<212> TYPE: PRT
<213> ORGANISM: Artificial Sequence
<220> FEATURE:
<223> OTHER INFORMATION: Insulin

<400> SEQUENCE: 125

Met Leu Lys Glu Lys Lys Tyr Ser Pro Asp Pro Gly Asp Pro Glu Cys
1               5                   10                  15

Leu Glu Gln Leu Leu Arg Arg Leu Gly Gly Ser Val Glu Val Glu Val
            20                  25                  30

Thr Gly Gly Thr Val His Val Glu Val Ser Pro Glu Asp Pro Gly Asp
        35                  40                  45

Pro Glu Cys Leu Glu Gln Leu Leu Arg Arg Leu Gly Gly Ser Val Glu
    50                  55                  60

Val Glu Val Thr Gly Gly Thr Val His Val Glu Val Ser Pro Gly Glu
65                  70                  75                  80

Arg Gly Phe Phe Tyr Cys Asn
                85


<210> SEQ ID NO 126
<211> LENGTH: 23
<212> TYPE: PRT
<213> ORGANISM: Artificial Sequence
<220> FEATURE:
<223> OTHER INFORMATION: Insulin fusion protein
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (18)..(18)
<223> OTHER INFORMATION: X = any amino acid

<400> SEQUENCE: 126

Met Ala Thr Ser Xaa Ser Thr Lys Lys Thr Gln Leu Gln Leu Glu His
1               5                   10                  15
```

Leu Xaa Leu Asp Leu Gln Met
            20

<210> SEQ ID NO 127
<211> LENGTH: 23
<212> TYPE: PRT
<213> ORGANISM: Escherichia coli
<220> FEATURE:
<221> NAME/KEY: MISC_FEATURE
<222> LOCATION: (14)..(14)
<223> OTHER INFORMATION: X = any amino acid
<220> FEATURE:
<221> NAME/KEY: MISC_FEATURE
<222> LOCATION: (17)..(17)
<223> OTHER INFORMATION: X = any amino acid

<400> SEQUENCE: 127

Thr Met Ile Thr Asp Ser Leu Ala Val Val Leu Gln Arg Xaa Asp Trp
1               5                   10                  15

Xaa Pro Gly Val Thr Gln Leu
            20

<210> SEQ ID NO 128
<211> LENGTH: 96
<212> TYPE: PRT
<213> ORGANISM: Brevibacillus brevis

<400> SEQUENCE: 128

Asn Ser Val Leu Ala Ser Ala Leu Ala Leu Thr Val Ala Pro Met Ala
1               5                   10                  15

Phe Ala Asn Ser Asp Ser Glu Ser Pro Leu Ser His Asp Gly Tyr Ser
            20                  25                  30

Leu His Asp Gly Val Ser Met Tyr Ile Glu Ala Leu Asp Lys Phe Val
        35                  40                  45

Asn Gln His Leu Cys Gly Ser His Leu Val Glu Ala Leu Tyr Leu Val
    50                  55                  60

Cys Gly Glu Arg Gly Phe Phe Tyr Thr Pro Lys Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 129
<211> LENGTH: 25
<212> TYPE: PRT
<213> ORGANISM: Artificial Sequence
<220> FEATURE:
<223> OTHER INFORMATION: Insulin fusion protein

<400> SEQUENCE: 129

Asp Thr Thr Met Pro Ala Gly Gly Gly Gly Gly Gly Gln His Leu Cys
1               5                   10                  15

Gly Pro His Leu Val Glu Ala Leu Tyr
            20                  25

<210> SEQ ID NO 130
<211> LENGTH: 6
<212> TYPE: PRT
<213> ORGANISM: Artificial Sequence
<220> FEATURE:
<223> OTHER INFORMATION: Insulin fusion protein

<400> SEQUENCE: 130

Leu Glu Asn Tyr Cys Asn

-continued

```
1               5


<210> SEQ ID NO 131
<211> LENGTH: 22
<212> TYPE: PRT
<213> ORGANISM: Artificial Sequence
<220> FEATURE:
<223> OTHER INFORMATION: Insulin fusion protein

<400> SEQUENCE: 131

Met Thr Met Ile Thr Asp Ser Leu Glu Phe Gln Ala Trp Gly Gly Gly
1               5                   10                  15

Gly Gly Trp Met Arg Phe
            20


<210> SEQ ID NO 132
<211> LENGTH: 22
<212> TYPE: PRT
<213> ORGANISM: Artificial Sequence
<220> FEATURE:
<223> OTHER INFORMATION: Insulin fusion protein

<400> SEQUENCE: 132

Met Val Leu Arg Phe Leu Pro Leu Leu Ala Leu Leu Val Leu Trp Glu
1               5                   10                  15

Pro Lys Pro Ala Gln Ala
            20


<210> SEQ ID NO 133
<211> LENGTH: 60
<212> TYPE: PRT
<213> ORGANISM: Artificial Sequence
<220> FEATURE:
<223> OTHER INFORMATION: Mini-proinsulin

<400> SEQUENCE: 133

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Tyr Pro Gly Asp Val Lys Arg Gly Ile Val Glu Gln Cys Cys Thr Ser
        35                  40                  45

Ile Cys Ser Leu Tyr Gln Leu Glu Asn Tyr Cys Asn
    50                  55                  60


<210> SEQ ID NO 134
<211> LENGTH: 21
<212> TYPE: PRT
<213> ORGANISM: Homo sapiens

<400> SEQUENCE: 134

Gly Ile Val Glu Gln Cys Cys Lys Ser Ile Cys Ser Leu Tyr Gln Leu
1               5                   10                  15

Glu Asn Tyr Cys Asn
            20


<210> SEQ ID NO 135
<211> LENGTH: 30
<212> TYPE: PRT
<213> ORGANISM: Homo sapiens

<400> SEQUENCE: 135

Phe Val Asn Gln His Leu Cys Gly Ser His Leu Val Glu Ala Leu Tyr
```

-continued

```
1               5                   10                  15

Leu Val Cys Gly Glu Arg Gly Phe Phe Tyr Thr Pro Lys Thr
            20                  25                  30


<210> SEQ ID NO 136
<211> LENGTH: 21
<212> TYPE: PRT
<213> ORGANISM: Homo sapiens

<400> SEQUENCE: 136

Gly Ile Val Glu Gln Cys Cys Lys Ser Ile Cys Ser Leu Tyr Gln Leu
1               5                   10                  15

Glu Asn Tyr Cys Asn
            20


<210> SEQ ID NO 137
<211> LENGTH: 30
<212> TYPE: PRT
<213> ORGANISM: Homo sapiens

<400> SEQUENCE: 137

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 138
<211> LENGTH: 14
<212> TYPE: PRT
<213> ORGANISM: Artificial Sequence
<220> FEATURE:
<223> OTHER INFORMATION: Homo sapiens insulin

<400> SEQUENCE: 138

Leu Val Glu Ala Leu Tyr Leu Val Cys Gly Glu Arg Gly Gly
1               5                   10


<210> SEQ ID NO 139
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X = any amino acid

<400> SEQUENCE: 139

Gly Ile Val Glu Gln Cys Cys Xaa Ser Ile Cys Ser Leu Tyr Gln Leu
1               5                   10                  15

Glu Asn Tyr Cys Asn
            20


<210> SEQ ID NO 140
<211> LENGTH: 30
<212> TYPE: PRT
<213> ORGANISM: Artificial Sequence
<220> FEATURE:
<223> OTHER INFORMATION: Homo sapiens insulin

<400> SEQUENCE: 140

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

-continued

<210> SEQ ID NO 141
<211> LENGTH: 21
<212> TYPE: PRT
<213> ORGANISM: Artificial Sequence
<220> FEATURE:
<223> OTHER INFORMATION: Homo sapiens insulin
<220> FEATURE:
<221> NAME/KEY: MISC_FEATURE
<222> LOCATION: (8)..(8)
<223> OTHER INFORMATION: X = any amino acid

<400> SEQUENCE: 141

Gly Ile Val Glu Gln Cys Cys Xaa Ser Ile Cys Ser Leu Tyr Gln Leu
1 5 10 15

Glu Asn Tyr Cys Asn
20

<210> SEQ ID NO 142
<211> LENGTH: 30
<212> TYPE: PRT
<213> ORGANISM: Artificial Sequence
<220> FEATURE:
<223> OTHER INFORMATION: Homo sapiens insulin

<400> SEQUENCE: 142

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> SEQ ID NO 143
<211> LENGTH: 21
<212> TYPE: PRT
<213> ORGANISM: Artificial Sequence
<220> FEATURE:
<223> OTHER INFORMATION: Mini-proinsulin mutant

<400> SEQUENCE: 143

Gly Ile Val Glu Gln Cys Cys Thr Ser Ile Cys Ser Leu Tyr Gln Leu
1 5 10 15

Glu Asn Tyr Cys Asn
20

<210> SEQ ID NO 144
<211> LENGTH: 29
<212> TYPE: PRT
<213> ORGANISM: Artificial Sequence
<220> FEATURE:
<223> OTHER INFORMATION: Mini-proinsulin mutant

<400> SEQUENCE: 144

Phe Val Asn Gln His Leu Cys Gly Ser Asp Leu Val Glu Ala Leu Tyr
1 5 10 15

Leu Val Cys Gly Glu Arg Gly Phe Phe Tyr Thr Asp Lys
20 25

<210> SEQ ID NO 145
<211> LENGTH: 50
<212> TYPE: PRT
<213> ORGANISM: Artificial Sequence
<220> FEATURE:
<223> OTHER INFORMATION: Mini-proinsulin mutant

<400> SEQUENCE: 145

-continued

Phe Val Asn Gln His Leu Cys Gly Ser Asp Leu Val Glu Ala Leu Tyr
1 5 10 15

Leu Val Cys Gly Glu Arg Gly Phe Phe Tyr Thr Asp Lys Gly Ile Val
20 25 30

Glu Gln Cys Cys Thr Ser Ile Cys Ser Leu Tyr Gln Leu Glu Asn Tyr
35 40 45

Cys Asn
50

<210> SEQ ID NO 146
<211> LENGTH: 3
<212> TYPE: PRT
<213> ORGANISM: Artificial Sequence
<220> FEATURE:
<223> OTHER INFORMATION: Insulin C-peptide

<400> SEQUENCE: 146

Ala Ala Lys
1

<210> SEQ ID NO 147
<211> LENGTH: 3
<212> TYPE: PRT
<213> ORGANISM: Artificial Sequence
<220> FEATURE:
<223> OTHER INFORMATION: Insulin C-peptide

<400> SEQUENCE: 147

Asn Lys Arg
1

<210> SEQ ID NO 148
<211> LENGTH: 6
<212> TYPE: PRT
<213> ORGANISM: Artificial Sequence
<220> FEATURE:
<223> OTHER INFORMATION: Insulin C-peptide

<400> SEQUENCE: 148

Arg Arg Lys Gln Lys Arg
1 5

<210> SEQ ID NO 149
<211> LENGTH: 4
<212> TYPE: PRT
<213> ORGANISM: Artificial Sequence
<220> FEATURE:
<223> OTHER INFORMATION: Cleavage site

<400> SEQUENCE: 149

Arg Arg Lys Arg
1

<210> SEQ ID NO 150
<211> LENGTH: 4
<212> TYPE: PRT
<213> ORGANISM: Artificial Sequence
<220> FEATURE:
<223> OTHER INFORMATION: ER retention sequence

<400> SEQUENCE: 150

Lys Asp Glu Leu
1

<210> SEQ ID NO 151

-continued

<211> LENGTH: 4
<212> TYPE: PRT
<213> ORGANISM: Artificial Sequence
<220> FEATURE:
<223> OTHER INFORMATION: ER retention sequence

<400> SEQUENCE: 151

His Asp Glu Leu
1

<210> SEQ ID NO 152
<211> LENGTH: 4
<212> TYPE: PRT
<213> ORGANISM: Artificial Sequence
<220> FEATURE:
<223> OTHER INFORMATION: ER retention sequence

<400> SEQUENCE: 152

Asp Asp Glu Leu
1

<210> SEQ ID NO 153
<211> LENGTH: 4
<212> TYPE: PRT
<213> ORGANISM: Artificial Sequence
<220> FEATURE:
<223> OTHER INFORMATION: ER retention sequence

<400> SEQUENCE: 153

Ala Asp Glu Leu
1

<210> SEQ ID NO 154
<211> LENGTH: 4
<212> TYPE: PRT
<213> ORGANISM: Artificial Sequence
<220> FEATURE:
<223> OTHER INFORMATION: ER retention sequence

<400> SEQUENCE: 154

Ser Asp Glu Leu
1

<210> SEQ ID NO 155
<211> LENGTH: 4
<212> TYPE: PRT
<213> ORGANISM: Lycopersicon esculentum Mill.

<400> SEQUENCE: 155

His Asp Glu Phe
1

<210> SEQ ID NO 156
<211> LENGTH: 118
<212> TYPE: PRT
<213> ORGANISM: Arabidopsis thaliana

<400> SEQUENCE: 156

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
```

-continued

```
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys
        115


<210> SEQ ID NO 157
<211> LENGTH: 187
<212> TYPE: PRT
<213> ORGANISM: Brassica napus

<400> SEQUENCE: 157

Met Ala Asp Thr Ala Arg Thr His His Asp Val Thr Ser Arg Asp Gln
1               5                   10                  15

Tyr Pro Arg Asp Arg Asp Gln Tyr Ser Met Ile Gly Arg Asp Arg Asp
            20                  25                  30

Gln Tyr Ser Met Met Gly Arg Asp Arg Asp Gln Tyr Asn Met Tyr Gly
        35                  40                  45

Arg Asp Tyr Ser Lys Ser Arg Gln Ile Ala Lys Ala Val Thr Ala Val
    50                  55                  60

Thr Ala Gly Gly Ser Leu Leu Val Leu Ser Ser Leu Thr Leu Val Gly
65                  70                  75                  80

Thr Val Ile Ala Leu Thr Val Ala Thr Pro Leu Leu Val Ile Phe Ser
                85                  90                  95

Pro Ile Leu Val Pro Ala Leu Ile Thr Val Ala Leu Leu Ile Thr Gly
            100                 105                 110

Phe Leu Ser Ser Gly Gly Phe Ala Ile Ala Ala Ile Thr Val Phe Ser
        115                 120                 125

Trp Ile Tyr Lys Tyr Ala Thr Gly Glu His Pro Gln Gly Ser Asp Lys
    130                 135                 140

Leu Asp Ser Ala Arg Met Lys Leu Gly Thr Lys Ala Gln Asp Ile Lys
145                 150                 155                 160

Asp Arg Ala Gln Tyr Tyr Gly Gln Gln His Thr Gly Gly Glu His Asp
                165                 170                 175

Arg Asp Arg Thr Arg Gly Gly Gln His Thr Thr
            180                 185


<210> SEQ ID NO 158
<211> LENGTH: 748
<212> TYPE: DNA
<213> ORGANISM: Arabidopsis thaliana

<400> SEQUENCE: 158

taccatgggg tcaaagacgg agatgatgga gagagacgca atggctacgg tggctcccta     60

tgcgccggtc acttaccatc gccgtgctcg tgttgacttg gatgatagac ttcctaaacc    120

ttatatgcca agagcattgc aagcaccaga cagagaacac ccgtacggaa ctccaggcca    180

taagaattac ggacttagtg ttcttcaaca gcatgtctcc ttcttcgata tcgatgataa    240

tggcatcatt tacccttggg agacctactc tggactgcga atgcttggtt tcaatatcat    300

tgggtcgctt ataatagccg ctgttatcaa cctgaccctt agctatgcca ctcttccggg    360

gtggttacct tcacctttct tccctatata catacacaac atacacaagt caaagcatgg    420
```

-continued

```
aagtgattca aaaacatatg acaatgaagg aaggtttatg ccggtgaatc ttgagttgat    480

atttagcaaa tatgcgaaaa ccttgccaga caagttgagt cttggagaac tatgggagat    540

gacagaagga aaccgtgacg cttgggacat ttttggatgg atcgcaggca aaatagagtg    600

gggactgttg tacttgctag caagggatga agaagggttt ttgtcaaaag aagctattag    660

gcggtgtttc gatggaagct tgttcgagta ctgtgccaaa atctacgctg gtatcagtga    720

agacaagaca gcatactacg ccatggat                                        748
```

<210> SEQ ID NO 159
<211> LENGTH: 738
<212> TYPE: DNA
<213> ORGANISM: Arabidopsis thaliana

<400> SEQUENCE: 159

```
atggggtcaa agacggagat gatggagaga gacgcaatgg ctacggtggc tccctatgcg     60

ccggtcactt accaccgccg tgctcgtgtt gacttggatg atagacttcc taaaccttat    120

atgccaagag cattgcaagc accagacaga gaacacccgt acggaactcc aggccataag    180

aattacggac ttagtgttct tcaacagcat gtctccttct tcgatatcga tgataatggc    240

atcatttacc cttgggagac ctactctgga ctgcgaatgc ttggtttcaa tatcattggg    300

tcgcttataa tagccgctgt tatcaacctg acccttagct atgccactct tccggggtgg    360

ttaccttcac ctttcttccc tatatacata cacaacatac acaagtcaaa gcatggaagt    420

gattcaaaaa catatgacaa tgaaggaagg tttatgccgg tgaatcttga gttgatattt    480

agcaaatatg cgaaaacctt gccagacaag ttgagtcttg gagaactatg ggagatgaca    540

gaaggaaacc gtgacgcttg ggacattttt ggatggatcg caggcaaaat agagtgggga    600

ctgttgtact tgctagcaag ggatgaagaa gggtttttgt caaaagaagc tattaggcgg    660

tgtttcgatg gaagcttgtt cgagtactgt gccaaaatct acgctggtat cagtgaagac    720

aagacagcat actactaa                                                   738
```

<210> SEQ ID NO 160
<211> LENGTH: 1047
<212> TYPE: DNA
<213> ORGANISM: Sesamum indicum

<400> SEQUENCE: 160

```
atggatctaa tccacacttt cctcaactta atagctcccc ctttcacctt cttcttcctt     60

ctctttttct tgccaccctt ccagattttc aagttcttcc tttcaatctt gggcaccctt    120

ttcagcgagg atgtcgctgg aaaagtcgtc gtcatcaccg gcgcctcctc cggcatcggc    180

gaaagtcttg cttacgagta tgctaagaga ggggcgtgct tggtgcttgc tgcaagaagg    240

gaaaggagtc ttcaagaagt ggccgaaagg gcgcgcgatt tggggtcgcc ggacgtcgtg    300

gtggtccggg ccgatgtttc gaaggcggag gactgcagga aggttgttga tcagactatg    360

aatcgctttg gaagattgga tcacctggtc aataacgctg gaattatgtc agtttcaatg    420

ctggaagaag ttgaagatat tactggttac agagaaacta tggatatcaa cttctggggc    480

tatgtgtata tgacccgatt tgccgcccca taccttagga atagcagagg ccgaattgtt    540

gtactttctt catccagttc ttggatgcct actccgagga tgagttttta caatgcaagc    600

aaagcggcga tttcacaatt ttttgagaca ctgcgggtgg aattcggccc cgatataggc    660

ataacccttg tgactccagg attcatagaa tctgaactta cccaaggcaa attctacaat    720
```

-continued

```
gctggcgaac gtgtaattga tcaggacatg agagatgtac aagtgagcac gactccaatc    780

ctgagggtgg aaagtgcggc aaggtcaatc gtgaggagcg cgatccgtgg agaaagatac    840

gtgacagagc cggcctggtt tagggttact tattggtgga agctattctg ccctgaggtg    900

atggagtggg tatttagact gatgtacttg gccagcccgg gtgagccgga gaaggaaacg    960

tttggcaaga aggttttgga ttacacagga gtgaagtcct tgctttaccc ggaaaccgtg   1020

caagttccgg agcccaagaa tgattaa                                       1047


<210> SEQ ID NO 161
<211> LENGTH: 25
<212> TYPE: PRT
<213> ORGANISM: Tobacco, pathogensis related protein (PR-S) signal
      sequence

<400> SEQUENCE: 161

Met Asn Phe Leu Lys Ser Phe Pro Phe Tyr Ala Phe Leu Cys Phe Gly
1               5                   10                  15

Gln Tyr Phe Val Ala Val Thr His Ala
            20                  25


<210> SEQ ID NO 162
<211> LENGTH: 64
<212> TYPE: PRT
<213> ORGANISM: Artificial Sequence
<220> FEATURE:
<223> OTHER INFORMATION: Alpha factor leader seqence

<400> SEQUENCE: 162

Ala Pro Val Asn Thr Thr Glu Asp Glu Thr Ala Gln Ala Glu Ala Val
1               5                   10                  15

Ile Gly Tyr Ser Asp Leu Glu Gly Asp Phe Asp Val Ala Val Leu Pro
            20                  25                  30

Phe Ser Asn Ser Thr Asn Asn Gly Leu Leu Phe Ile Asx Thr Thr Ile
        35                  40                  45

Ala Ser Ile Ala Ala Lys Glu Glu Gly Val Ser Leu Met Ala Lys Arg
    50                  55                  60


<210> SEQ ID NO 163
<211> LENGTH: 63
<212> TYPE: PRT
<213> ORGANISM: Artificial Sequence
<220> FEATURE:
<223> OTHER INFORMATION: Alpha factor leader sequence

<400> SEQUENCE: 163

Ala Pro Val Asn Thr Thr Glu Asp Glu Thr Ala Gln Ala Glu Ala Val
1               5                   10                  15

Ile Gly Tyr Ser Asp Leu Glu Gly Asp Phe Asp Val Ala Val Leu Pro
            20                  25                  30

Phe Ser Asn Ser Thr Asn Asn Gly Leu Leu Phe Ile Asx Thr Thr Ile
        35                  40                  45

Ala Ser Ile Ala Ala Lys Glu Glu Gly Val Ser Met Ala Lys Arg
    50                  55                  60


<210> SEQ ID NO 164
<211> LENGTH: 15
<212> TYPE: PRT
<213> ORGANISM: Artificial Sequence
<220> FEATURE:
<223> OTHER INFORMATION: Alpha factor leader sequence
```

-continued

<400> SEQUENCE: 164

Gln Pro Ile Asp Glu Asp Asn Asp Thr Ser Ser Met Ala Lys Arg
1 5 10 15

<210> SEQ ID NO 165
<211> LENGTH: 43
<212> TYPE: PRT
<213> ORGANISM: Artificial Sequence
<220> FEATURE:
<223> OTHER INFORMATION: Alpha factor leader sequence

<400> SEQUENCE: 165

Gln Pro Ile Asp Asp Thr Glu Ser Asn Thr Thr Ser Val Asn Leu Met
1 5 10 15

Ala Asp Asp Thr Glu Asp Arg Phe Ala Thr Asn Thr Thr Leu Ala Leu
20 25 30

Asp Val Val Asn Leu Ile Ser Met Ala Lys Arg
35 40

<210> SEQ ID NO 166
<211> LENGTH: 43
<212> TYPE: PRT
<213> ORGANISM: Artificial Sequence
<220> FEATURE:
<223> OTHER INFORMATION: Alpha factor leader sequence

<400> SEQUENCE: 166

Gln Pro Ile Asp Asp Thr Glu Ser Gln Thr Thr Ser Val Asn Leu Met
1 5 10 15

Ala Asp Asp Thr Glu Asp Arg Phe Ala Thr Gln Thr Thr Leu Ala Leu
20 25 30

Asp Val Val Asn Leu Ile Ser Met Ala Lys Arg
35 40

<210> SEQ ID NO 167
<211> LENGTH: 43
<212> TYPE: PRT
<213> ORGANISM: Artificial Sequence
<220> FEATURE:
<223> OTHER INFORMATION: Alpha factor leader sequence

<400> SEQUENCE: 167

Gln Pro Ile Asp Asp Thr Glu Ser Gln Thr Thr Ser Val Asn Leu Met
1 5 10 15

Ala Asp Asp Thr Glu Asp Arg Phe Ala Thr Gln Thr Thr Leu Ala Leu
20 25 30

Asp Val Val Asn Leu Ile Ser Met Ala Ala Ala
35 40

<210> SEQ ID NO 168
<211> LENGTH: 43
<212> TYPE: PRT
<213> ORGANISM: Artificial Sequence
<220> FEATURE:
<223> OTHER INFORMATION: Alpha factor leader sequence

<400> SEQUENCE: 168

Gln Pro Ile Asp Asp Thr Glu Ser Asn Thr Thr Ser Val Asn Leu Met
1 5 10 15

Ala Asp Asp Thr Glu Asp Arg Phe Ala Thr Asn Thr Thr Leu Ala Leu
20 25 30

Asp Val Val Asn Leu Ile Ser Met Ala Ala Ala

-continued 35 40

<210> SEQ ID NO 169
<211> LENGTH: 45
<212> TYPE: PRT
<213> ORGANISM: Artificial Sequence
<220> FEATURE:
<223> OTHER INFORMATION: Alpha factor leader sequence

<400> SEQUENCE: 169

Gln Pro Ile Asp Asp Thr Glu Ser Asn Thr Thr Ser Val Asn Leu Met
1 5 10 15

Ala Asp Asp Thr Glu Asp Arg Phe Ala Thr Asn Thr Thr Leu Ala Gly
20 25 30

Gly Leu Asp Val Val Asn Leu Ile Ser Met Ala Lys Arg
35 40 45

<210> SEQ ID NO 170
<211> LENGTH: 44
<212> TYPE: PRT
<213> ORGANISM: Artificial Sequence
<220> FEATURE:
<223> OTHER INFORMATION: Alpha factor leader sequence

<400> SEQUENCE: 170

Gln Pro Ile Asp Asp Thr Glu Ser Gln Thr Thr Ser Val Asn Leu Met
1 5 10 15

Ala Asp Asp Thr Glu Ser Ala Phe Ala Thr Gln Thr Asn Ser Gly Gly
20 25 30

Leu Asp Val Val Gly Leu Ile Ser Met Ala Lys Arg
35 40

<210> SEQ ID NO 171
<211> LENGTH: 44
<212> TYPE: PRT
<213> ORGANISM: Artificial Sequence
<220> FEATURE:
<223> OTHER INFORMATION: Alpha factor leader sequence

<400> SEQUENCE: 171

Gln Pro Ile Asp Asp Thr Glu Ser Gln Thr Thr Ser Val Asn Leu Met
1 5 10 15

Ala Asp Asp Thr Glu Ser Ala Phe Ala Thr Gln Thr Asn Ser Gly Gly
20 25 30

Leu Asp Val Val Gly Leu Ile Ser Met Ala Ala Ala
35 40

<210> SEQ ID NO 172
<211> LENGTH: 10
<212> TYPE: PRT
<213> ORGANISM: Spacer peptide

<400> SEQUENCE: 172

Glu Glu Ala Glu Ala Glu Ala Glu Pro Lys
1 5 10

<210> SEQ ID NO 173
<211> LENGTH: 6
<212> TYPE: PRT
<213> ORGANISM: Artificial Sequence
<220> FEATURE:
<223> OTHER INFORMATION: Spacer peptide

<400> SEQUENCE: 173

-continued

Glu Glu Gly Glu Pro Lys
1 5

<210> SEQ ID NO 174
<211> LENGTH: 40
<212> TYPE: PRT
<213> ORGANISM: Artificial Sequence
<220> FEATURE:
<223> OTHER INFORMATION: Cleavage site

<400> SEQUENCE: 174

Met Ala Glu Ile Thr Arg Ile Pro Leu Tyr Lys Gly Lys Ser Leu Arg
1 5 10 15

Lys Ala Leu Lys Glu His Gly Leu Leu Glu Asp Phe Leu Gln Lys Gln
20 25 30

Gln Tyr Gly Ile Ser Ser Lys Phe
35 40

<210> SEQ ID NO 175
<211> LENGTH: 27
<212> TYPE: DNA
<213> ORGANISM: Artificial Sequence
<220> FEATURE:
<223> OTHER INFORMATION: Primer

<400> SEQUENCE: 175
gcatgctgac attgtgatga cacagtc 27

<210> SEQ ID NO 176
<211> LENGTH: 43
<212> TYPE: DNA
<213> ORGANISM: Artificial Sequence
<220> FEATURE:
<223> OTHER INFORMATION: Primer

<400> SEQUENCE: 176
aagcttgcat ttaaatactc gagactgtga gagtggtgcc ttg 43

<210> SEQ ID NO 177
<211> LENGTH: 70
<212> TYPE: DNA
<213> ORGANISM: Artificial Sequence
<220> FEATURE:
<223> OTHER INFORMATION: Primer

<400> SEQUENCE: 177
gaagaaggag agcctaagtt tgttaatcaa catctttgtg gatctcatct tgttgaggct 60
ctctaccttg 70

<210> SEQ ID NO 178
<211> LENGTH: 56
<212> TYPE: DNA
<213> ORGANISM: Artificial Sequence
<220> FEATURE:
<223> OTHER INFORMATION: Primer

<400> SEQUENCE: 178
ccttaggagt gtagaaaaat cctctttctc cacacacaag gtagagagcc tcaaca 56

<210> SEQ ID NO 179
<211> LENGTH: 21
<212> TYPE: DNA
<213> ORGANISM: Artificial Sequence
<220> FEATURE:

-continued

<223> OTHER INFORMATION: Primer

<400> SEQUENCE: 179
ctaaggctgc taagggaatt g 21

<210> SEQ ID NO 180
<211> LENGTH: 83
<212> TYPE: DNA
<213> ORGANISM: Artificial Sequence
<220> FEATURE:
<223> OTHER INFORMATION: Primer

<400> SEQUENCE: 180
aagcttcagt tgcaatagtt ctccaattgg taaagtgagc aaatagaagt gcaacattgt 60
tcaacaattc ccttagcagc ctt 83

<210> SEQ ID NO 181
<211> LENGTH: 30
<212> TYPE: DNA
<213> ORGANISM: Artificial Sequence
<220> FEATURE:
<223> OTHER INFORMATION: Primer

<400> SEQUENCE: 181
ctcgagtcaa ccaattgatg acactgaatc 30

<210> SEQ ID NO 182
<211> LENGTH: 41
<212> TYPE: DNA
<213> ORGANISM: Artificial Sequence
<220> FEATURE:
<223> OTHER INFORMATION: Primer

<400> SEQUENCE: 182
aagcttcaaa gttcatcctt gttgcaatag ttctccaatt g 41

<210> SEQ ID NO 183
<211> LENGTH: 21
<212> TYPE: DNA
<213> ORGANISM: Artificial Sequence
<220> FEATURE:
<223> OTHER INFORMATION: Primer

<400> SEQUENCE: 183
aagcttcagt tgcaatagtt c 21

<210> SEQ ID NO 184
<211> LENGTH: 26
<212> TYPE: DNA
<213> ORGANISM: Artificial Sequence
<220> FEATURE:
<223> OTHER INFORMATION: Primer

<400> SEQUENCE: 184
gcatgcccaa ccaattgatg acactg 26

<210> SEQ ID NO 185
<211> LENGTH: 34
<212> TYPE: DNA
<213> ORGANISM: Artificial Sequence
<220> FEATURE:
<223> OTHER INFORMATION: Primer

<400> SEQUENCE: 185
gcatgcatgc ctttgttaat caacatcttt gtgg 34

-continued

<210> SEQ ID NO 186
<211> LENGTH: 54
<212> TYPE: DNA
<213> ORGANISM: Artificial Sequence
<220> FEATURE:
<223> OTHER INFORMATION: Primer

<400> SEQUENCE: 186
acattgttca acaattcctc tctttcttct agtcttagga gtgtagaaaa atcc 54

<210> SEQ ID NO 187
<211> LENGTH: 29
<212> TYPE: DNA
<213> ORGANISM: Artificial Sequence
<220> FEATURE:
<223> OTHER INFORMATION: Primer

<400> SEQUENCE: 187
gcataagctt caaagctcat cctttgagc 29

<210> SEQ ID NO 188
<211> LENGTH: 387
<212> TYPE: DNA
<213> ORGANISM: Artificial Sequence
<220> FEATURE:
<223> OTHER INFORMATION: Insulin fusion protein nucleic acid sequence

<400> SEQUENCE: 188
atgaacttcc ttaagtcttt ccctttctac gctttccttt gtttcggtca atacttcgtt 60
gctgttacgc atgcccaacc aattgatgac actgaatccc agaccacgtc agtgaacctc 120
atggccgatg atactgagag cgcgtttgct acacaaacaa attcgggagg tcttgacgtt 180
gtcggattga tctccatggc taagagagaa gaaggagagc ctaagtttgt taatcaacat 240
ctttgtggat ctcatcttgt tgaggctctc taccttgtgt gtggagaaag aggatttttc 300
tacactccta aggctgctaa gggaattgtt gaacaatgtt gcacttctat ttgctcactt 360
taccaattgg agaactattg caactga 387

<210> SEQ ID NO 189
<211> LENGTH: 128
<212> TYPE: PRT
<213> ORGANISM: Artificial Sequence
<220> FEATURE:
<223> OTHER INFORMATION: Insulin factor protein

<400> SEQUENCE: 189

Met Asn Phe Leu Lys Ser Phe Pro Phe Tyr Ala Phe Leu Cys Phe Gly
1 5 10 15

Gln Tyr Phe Val Ala Val Thr His Ala Gln Pro Ile Asp Asp Thr Glu
20 25 30

Ser Gln Thr Thr Ser Val Asn Leu Met Ala Asp Asp Thr Glu Ser Ala
35 40 45

Phe Ala Thr Gln Thr Asn Ser Gly Gly Leu Asp Val Val Gly Leu Ile
50 55 60

Ser Met Ala Lys Arg Glu Glu Gly Glu Pro Lys Phe Val Asn Gln His
65 70 75 80

Leu Cys Gly Ser His Leu Val Glu Ala Leu Tyr Leu Val Cys Gly Glu
85 90 95

Arg Gly Phe Phe Tyr Thr Pro Lys Ala Ala Lys Gly Ile Val Glu Gln
100 105 110

-continued

Cys Cys Thr Ser Ile Cys Ser Leu Tyr Gln Leu Glu Asn Tyr Cys Asn
115 120 125

<210> SEQ ID NO 190
<211> LENGTH: 18
<212> TYPE: DNA
<213> ORGANISM: Artificial Sequence
<220> FEATURE:
<223> OTHER INFORMATION: Primer

<400> SEQUENCE: 190
ttcgtgaacc aacacttg 18

<210> SEQ ID NO 191
<211> LENGTH: 20
<212> TYPE: DNA
<213> ORGANISM: Artificial Sequence
<220> FEATURE:
<223> OTHER INFORMATION: Primer

<400> SEQUENCE: 191
aagctttcag ttacagtagt 20

<210> SEQ ID NO 192
<211> LENGTH: 17
<212> TYPE: DNA
<213> ORGANISM: Artificial Sequence
<220> FEATURE:
<223> OTHER INFORMATION: Primer

<400> SEQUENCE: 192
gcatgcatgt gttgagc 17

<210> SEQ ID NO 193
<211> LENGTH: 16
<212> TYPE: DNA
<213> ORGANISM: Artificial Sequence
<220> FEATURE:
<223> OTHER INFORMATION: Primer

<400> SEQUENCE: 193
ggtagtgtgc tggcca 16

<210> SEQ ID NO 194
<211> LENGTH: 38
<212> TYPE: DNA
<213> ORGANISM: Artificial Sequence
<220> FEATURE:
<223> OTHER INFORMATION: Primer

<400> SEQUENCE: 194
ggtggccagc acactacctt cgtgaaccaa cacttgtg 38

<210> SEQ ID NO 195
<211> LENGTH: 1020
<212> TYPE: DNA
<213> ORGANISM: Artificial Sequence
<220> FEATURE:
<223> OTHER INFORMATION: Insulin fusion protein nucleic acid sequence

<400> SEQUENCE: 195
atggcggata cagctagagg aacccatcac gatatcatcg gcagagacca gtacccgatg 60
atgggccgag accgagacca gtaccagatg tccggacgag gatctgacta ctccaagtct 120
aggcagattg ctaaagctgc aactgctgtc acagctggtg gttccctcct tgttctctcc 180

-continued

```
agccttaccc ttgttggaac tgtcatagct ttgactgttg caacacctct gctcgttatc    240

ttcagcccaa tccttgtccc ggctctcatc acagttgcac tcctcatcac cggttttctt    300

tcctctggag ggtttggcat tgccgctata accgttttct cttggattta caagtaagca    360

cacatttatc atcttacttc ataattttgt gcaatatgtg catgcatgtg ttgagccagt    420

agctttggat caattttttt ggtagaataa caaatgtaac aataagaaat tgcaaattct    480

agggaacatt tggttaacta aatacgaaat ttgacctagc tagcttgaat gtgtctgtgt    540

atatcatcta tataggtaaa atgcttggta tgatacctat tgattgtgaa taggtacgca    600

acgggagagc acccacaggg atcagacaag ttggacagtg caaggatgaa gttgggaagc    660

aaagctcagg atctgaaaga cagagctcag tactacggac agcaacatac tggtggggaa    720

catgaccgtg accgtactcg tggtggccag cacactacct tcgtgaacca acacttgtgt    780

ggatctcatc tcgttgaagc tctctacttg gtttgtggtg agagaggatt cttctacact    840

cctaagacca gaagggaagc tgaggacttg caggtgggac aagttgagtt gggtggaggt    900

cctggagcag gatctttgca acctctcgct ttggaaggtt ctttgcagaa gagaggaatc    960

gttgaacaat gttgcacttc aatctgttct ttgtatcagt tggagaacta ctgtaactga   1020
```

<210> SEQ ID NO 196
<211> LENGTH: 257
<212> TYPE: PRT
<213> ORGANISM: Artificial Sequence
<220> FEATURE:
<223> OTHER INFORMATION: Insulin fusion protein

<400> SEQUENCE: 196

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Ala Thr Gly Glu His Pro Gln Gly Ser Asp Lys
        115                 120                 125

Leu Asp Ser Ala Arg Met Lys Leu Gly Ser Lys Ala Gln Asp Leu Lys
    130                 135                 140

Asp Arg Ala Gln Tyr Tyr Gly Gln Gln His Thr Gly Gly Glu His Asp
145                 150                 155                 160

Arg Asp Arg Thr Arg Gly Gly Gln His Thr Thr Phe Val Asn Gln His
                165                 170                 175

Leu Cys Gly Ser His Leu Val Glu Ala Leu Tyr Leu Val Cys Gly Glu
            180                 185                 190

Arg Gly Phe Phe Tyr Thr Pro Lys Thr Arg Arg Glu Ala Glu Asp Leu
        195                 200                 205

Gln Val Gly Gln Val Glu Leu Gly Gly Gly Pro Gly Ala Gly Ser Leu
```

-continued

```
    210                 215                 220

Gln Pro Leu Ala Leu Glu Gly Ser Leu Gln Lys Arg Gly Ile Val Glu
225                 230                 235                 240

Gln Cys Cys Thr Ser Ile Cys Ser Leu Tyr Gln Leu Glu Asn Tyr Cys
                245                 250                 255

Asn
```